US011111264B2

(12) United States Patent
Ware et al.

(10) Patent No.: US 11,111,264 B2
(45) Date of Patent: Sep. 7, 2021

(54) MORPHIC FORMS OF 4-AMINO-7-(3,4-DIHYDROXY-5-(HYDROXYMETHYL) TETRAHYDROFURAN-2-YL)-2-METHYL-7H-PYRROLO[2,3-D]PYRIMIDINE-5-CARBOXAMIDE AND USES THEREOF

(71) Applicant: Chimerix, Inc., Durham, NC (US)

(72) Inventors: Roy W. Ware, Raleigh, NC (US); Venkat Lakshmanan, Durham, NC (US); Aaron Leigh Downey, Durham, NC (US)

(73) Assignee: Chimerix, Inc., Durham, NC (US)

( * ) Notice: Subject to any disclaimer, the term of this patent is extended or adjusted under 35 U.S.C. 154(b) by 0 days.

(21) Appl. No.: 16/645,876

(22) PCT Filed: Sep. 21, 2018

(86) PCT No.: PCT/US2018/052180
§ 371 (c)(1),
(2) Date: Mar. 10, 2020

(87) PCT Pub. No.: WO2019/060692
PCT Pub. Date: Mar. 28, 2019

(65) Prior Publication Data
US 2020/0277323 A1    Sep. 3, 2020

Related U.S. Application Data

(60) Provisional application No. 62/561,355, filed on Sep. 21, 2017.

(51) Int. Cl.
*C07H 19/14*    (2006.01)

(52) U.S. Cl.
CPC .......... *C07H 19/14* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,423,398 A | 1/1969 | Rao et al. |
| 4,140,851 A | 2/1979 | Townsend |
| 4,892,865 A | 1/1990 | Townsend et al. |
| 5,177,064 A | 1/1993 | Bodor |
| 5,403,843 A | 4/1995 | Akimoto et al. |
| 5,502,187 A | 3/1996 | Ayer et al. |
| 5,506,347 A | 4/1996 | Erion et al. |
| 5,554,608 A | 9/1996 | Ahluwalia et al. |
| 5,646,128 A | 7/1997 | Firestein et al. |
| 5,656,745 A | 8/1997 | Bischofberger et al. |
| 5,674,998 A | 10/1997 | Boyer et al. |
| 5,721,356 A | 2/1998 | Ugarkar et al. |
| 5,726,302 A | 3/1998 | Ugarkar et al. |
| 5,763,167 A | 6/1998 | Conrad |
| 5,763,596 A | 6/1998 | Boyer et al. |
| 5,789,394 A | 8/1998 | Nguyen-ba et al. |
| 5,798,340 A | 8/1998 | Bischofberger et al. |
| 5,834,469 A | 11/1998 | Elliott et al. |
| 5,955,446 A | 9/1999 | Budowsky |
| 6,051,578 A | 4/2000 | Chen |
| 6,419,934 B1 | 7/2002 | Tobinick |
| 6,455,508 B1 | 9/2002 | Ramasamy |
| 6,468,991 B1 | 10/2002 | Budowsky et al. |
| 6,664,266 B2 | 12/2003 | He et al. |
| 6,670,468 B1 | 12/2003 | Cuenoud et al. |
| 6,777,395 B2 | 8/2004 | Bhat et al. |
| 6,777,404 B2 | 8/2004 | Hamanaka et al. |
| 6,831,069 B2 | 12/2004 | Tam et al. |
| 7,115,741 B2 | 10/2006 | Levy |
| 7,230,007 B2 | 6/2007 | Carry et al. |
| 7,323,453 B2 | 1/2008 | Olsen et al. |
| 7,358,262 B2 | 4/2008 | Stockwell |
| 7,361,671 B2 | 4/2008 | Van Zandt et al. |
| 7,553,826 B2 | 6/2009 | Boyer et al. |
| 7,608,600 B2 | 10/2009 | Storer et al. |
| 7,615,554 B2 | 11/2009 | Becklin et al. |
| 7,629,328 B2 | 12/2009 | Roberts et al. |
| 7,648,987 B2 | 1/2010 | Crew et al. |
| 7,687,500 B2 | 3/2010 | Howell et al. |
| 7,964,580 B2 | 6/2011 | Sofia et al. |
| 8,124,602 B2 | 2/2012 | Breault et al. |
| 8,124,745 B2 | 2/2012 | Allerson et al. |
| 8,173,621 B2 | 5/2012 | Du et al. |
| 8,207,136 B2 | 6/2012 | Gartel et al. |
| 8,278,282 B2 | 10/2012 | Yin et al. |
| 8,404,683 B2 | 3/2013 | Lacrampe et al. |
| 8,415,095 B2 | 4/2013 | Cupo et al. |
| 8,475,804 B2 | 7/2013 | Johansen et al. |

(Continued)

FOREIGN PATENT DOCUMENTS

| | | |
|---|---|---|
| CN | 1923171 | 3/2007 |
| CN | 1923173 | 3/2007 |

(Continued)

OTHER PUBLICATIONS

Morissette, Advanced Drug Delivery Reviews 56 (2004) 275-300. (Year: 2004).*
Berge, S. M. et al. "Pharmaceutical Salts", *Journal of Pharmaceutical Sciences*, 1977, vol. 66, No. 1, p. 1-19.
Cuellar. "HIV-Infection-Associated Inflammatory Musculoskeletal Disorders," *Disease Clinics of North America*, 1998, vol. 24, No. 2, p. 403-421.
Gould, P. L. "Salt selection for basic drugs", *International Journal of Pharmaceutics*, 1986, vol. 33, p. 201-217.

(Continued)

*Primary Examiner* — Layla D Berry
(74) *Attorney, Agent, or Firm* — Cooley LLP; Heidi A. Erlacher; Gabriel Magallanes

(57) ABSTRACT

The present disclosure relates to crystalline morphic forms of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide. The morphic form can be a stable hemihydrate crystalline form.

16 Claims, 35 Drawing Sheets

(56) References Cited

U.S. PATENT DOCUMENTS

| | | |
|---|---|---|
| 8,487,004 B2 | 7/2013 | Chen et al. |
| 8,575,119 B2 | 11/2013 | Wang et al. |
| 8,609,627 B2 | 12/2013 | Cho et al. |
| 8,642,602 B2 | 2/2014 | Mann et al. |
| 8,642,660 B2 | 2/2014 | Goldfarb |
| 8,674,085 B2 | 3/2014 | Sommadossi et al. |
| 8,697,713 B2 | 4/2014 | Jaekel et al. |
| 8,748,601 B2 | 6/2014 | Taunton et al. |
| 8,815,879 B2 | 8/2014 | Kasina et al. |
| 9,085,599 B2 | 7/2015 | Or et al. |
| 9,701,706 B2 | 7/2017 | Bougher, III et al. |
| 9,708,359 B2 | 7/2017 | Bougher, III et al. |
| 1,040,745 A1 | 9/2019 | Bougher, III et al. |
| 2001/0041673 A1 | 11/2001 | Fossa |
| 2002/0127593 A1 | 9/2002 | Reich et al. |
| 2002/0169140 A1 | 11/2002 | Prendergast |
| 2004/0006002 A1 | 1/2004 | Sommadosi et al. |
| 2004/0014108 A1 | 1/2004 | Eldrup et al. |
| 2004/0175384 A1 | 9/2004 | Mohapatra et al. |
| 2004/0259934 A1 | 12/2004 | Johansson et al. |
| 2005/0158741 A1 | 7/2005 | Mulligan et al. |
| 2005/0203151 A1 | 9/2005 | Malecha et al. |
| 2005/0282769 A1 | 12/2005 | Klimko et al. |
| 2006/0234962 A1 | 10/2006 | Olsen et al. |
| 2006/0264389 A1 | 11/2006 | Bhat et al. |
| 2007/0015771 A1 | 1/2007 | Matteucci |
| 2007/0161644 A1 | 7/2007 | Stockwell |
| 2007/0265222 A1 | 11/2007 | Maccoss et al. |
| 2007/0299091 A1 | 12/2007 | Gmeiner et al. |
| 2008/0153903 A1 | 6/2008 | Fleenor et al. |
| 2008/0255038 A1 | 10/2008 | Hopkins et al. |
| 2009/0318380 A1 | 12/2009 | Sofia et al. |
| 2010/0144655 A1 | 6/2010 | Chen et al. |
| 2010/0184650 A1 | 7/2010 | Jensen et al. |
| 2010/0297079 A1 | 11/2010 | Almond et al. |
| 2011/0218210 A1 | 9/2011 | Refaeli et al. |
| 2012/0010164 A1 | 1/2012 | Surnma et al. |
| 2012/0014911 A1 | 1/2012 | Fuchs et al. |
| 2012/0190680 A1 | 7/2012 | Bakthavatchalam et al. |
| 2012/0208750 A1 | 8/2012 | Kahn et al. |
| 2012/0238600 A1 | 9/2012 | Choi-Sledeski et al. |
| 2012/0245186 A1 | 9/2012 | Blackman et al. |
| 2013/0011393 A1 | 1/2013 | Lancaster et al. |
| 2013/0018010 A1 | 1/2013 | Zhao et al. |
| 2013/0137708 A1 | 5/2013 | Garske et al. |
| 2013/0281686 A1 | 10/2013 | Cho et al. |
| 2014/0213779 A1 | 7/2014 | Dixon et al. |
| 2015/0018301 A1 | 1/2015 | Lee et al. |
| 2015/0057243 A1 | 2/2015 | Zhou et al. |
| 2015/0087627 A1 | 3/2015 | Ren et al. |

FOREIGN PATENT DOCUMENTS

| | | |
|---|---|---|
| CN | 102286048 | 12/2011 |
| JP | S 61189225 | 8/1986 |
| JP | 2003321472 | 11/2003 |
| JP | 2007124252 | 5/2007 |
| KR | 2001086627 | 9/2001 |
| WO | WO 9205200 | 4/1992 |
| WO | WO 9217185 | 10/1992 |
| WO | WO 9418215 | 8/1994 |
| WO | WO 2003/020222 | 3/2003 |
| WO | WO 2003/051899 | 6/2003 |
| WO | WO 2003/061576 | 7/2003 |
| WO | WO 2003/075010 | 9/2003 |
| WO | WO 2004/028481 | 4/2004 |
| WO | WO 2005/020885 | 3/2005 |
| WO | WO 2007/024944 | 3/2007 |
| WO | WO 2008/021981 | 2/2008 |
| WO | WO 2008/132155 | 11/2008 |
| WO | WO 2009/067409 | 5/2009 |
| WO | WO 2009/105234 | 8/2009 |
| WO | WO 2009/108551 | 9/2009 |
| WO | WO 2010/015637 | 2/2010 |
| WO | WO 2011/079103 | 6/2011 |
| WO | WO 2011/106997 | 9/2011 |
| WO | WO 2012/041965 | 4/2012 |
| WO | WO 2012/153142 | 11/2012 |
| WO | WO 2013/071415 | 5/2013 |
| WO | WO 2014/060431 | 4/2014 |
| WO | WO 2014/177585 | 11/2014 |

OTHER PUBLICATIONS

Hall et al. "Norovirus Disease in the United States", *Emerging Infectious Disease*, 2013, vol. 19, No. 8, p. 1198-1205.

Naus, P. et al., "Synthesis, Cytostatic, Antimicrobial, and Anti-HCV Activity of 6-Substituted 7-(Het)aryl-7-deazapurine Ribonucleosides", *Journal of Medicinal Chemistry*, 2014, vol. 57, No. 3, p. 1097-1110.

Miller J. et al. "Solvent Systems for Crystallization and Polymorph Selection", Chapter 3, *Solvent Systems and Their Selection in Pharmaceutics and Biopharmaceutics*, 2007, pp. 53-109.

Phan et al. "Genetic Heterogeneity, Evolution, and Recombination in Noroviruses", *Journal of Medical Virology*, 2007, vol. 79, No. 9, p. 1388-1400.

Porcari et al. "Synthesis and Antiviral Activity of 2-Substituted Analogs of Triciribine", *Nucleosides, Nucleotides and Nucleic Acids*, 2003, vol. 22, No. 12, p. 2171-2193.

Variankaval, N., et al. "Water Activity-Mediated Control of Crystalline Phases of an Active Pharmaceutical Ingredient", *Organic Process Research & Development*, 2007, vol. 11, Issue 2, p. 229-236.

Zhu and Grant. "Influence of water activity in organic solvent + water mixtures on the nature of the crystallizing drug phase. 2. Ampicillin", *International Journal of Pharmaceutics*, 1996, vol. 139, Issue 1-2, p. 33-43.

\* cited by examiner

MORPHIC FORMS OF 4-AMINO-7-(3,4-DIHYDROXY-5-(HYDROXYMETHYL) TETRAHYDROFURAN-2-YL)-2-METHYL-7H-PYRROLO[2,3-D]PYRIMIDINE-5-CARBOXAMIDE AND USES THEREOF

RELATED APPLICATIONS

This application is a U.S. National Phase application, filed under 35 U.S.C. § 371, of International Application No. PCT/US2018/052180, filed Sep. 21, 2018, which claims priority to, and the benefit of, U.S. Provisional Patent Application No. 62/561,355, filed Sep. 21, 2017, the contents of each of which are incorporated by reference in their entireties.

FIELD OF THE INVENTION

The present disclosure relates to crystalline morphic forms of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide. The morphic form can be a stable hemihydrate crystalline form (e.g., Form A).

BACKGROUND OF THE INVENTION

Viral infections can have serious adverse effects on individuals and society as a whole. In addition to fatal viral infections such as Ebola, even non-fatal infections can have serious societal and economic consequences. For example, human noroviruses (NV) are the most common cause of epidemic acute gastroenteritis worldwide with an estimated 19-21 million cases each year in the United States including 56,000-71,000 hospitalizations and 570-800 deaths (Hall et al., *Emerg. Infect. Dis.* 2013 August; 19(8):1198-205).

4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide (Compound 1) is an antiviral drug.

SUMMARY OF THE INVENTION

The present disclosure provides morphic forms of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide (Compound 1). In some embodiments, the present disclosure provides stable crystalline hemihydrate morphic forms of Compound 1. In some embodiments, the hemihydrate form is the most stable form of Compound 1.

In one aspect, the present disclosure provides crystalline 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide hemihydrate.

In another aspect, the present disclosure provides crystalline 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide hemihydrate in substantially pure form.

In another aspect, the present disclosure provides a crystalline hemihydrate form ("Form A") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 26.2 (e.g., at 26.2±0.20 °2θ; at 26.2±0.15 °2θ; at 26.2±0.10 °2θ; at 26.2±0.05 °2θ; at 26.2±0.01 °2θ; or at 26.2 °2θ). In some embodiments, said powder X-ray diffraction pattern is obtained using Cu Kα1 X-rays at a wavelength of 1.5406 Å.

In another aspect, the present disclosure provides a method of preparing a crystalline hemihydrate form (e.g., "Form A") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide comprising: recrystallizing the 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide from a solvent having a water activity of at least about 0.18 (e.g., about 0.1, about 0.15, about 0.20, about 0.21, about 0.22, about 0.23, about 0.24, about 0.25, about 0.26, about 0.27, about 0.28, about 0.29, or about 0.30).

In another aspect, the present disclosure provides a crystalline Form (i.e., "Form B") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 22.9 (e.g., at 22.9±0.20 °2θ; at 22.9±0.15 °2θ; at 22.9±0.10 °2θ; at 22.9±0.05 °2θ; at 22.9±0.01 °2θ; or at 22.9 °2θ). In some embodiments, said powder X-ray diffraction pattern is obtained using Cu Kα1 X-rays at a wavelength of 1.5406 Å.

In another aspect, the present disclosure provides a crystalline Form (i.e., "Form C") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 22.4 (e.g., at 22.4±0.20 °2θ; at 22.4±0.15 °2θ; at 22.4±0.10 °2θ; at 22.4±0.05 °2θ; at 22.4±0.01 °2θ; or at 22.4 °2θ). In some embodiments, said powder X-ray diffraction pattern is obtained using Cu Kα1 X-rays at a wavelength of 1.5406 Å.

In another aspect, the present disclosure provides a crystalline Form (i.e., "Form D") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 26.6 (e.g., at 26.6±0.20 °2θ; at 26.6±0.15 °2θ; at 26.6±0.10 °2θ; at 26.6±0.05 °2θ; at 26.6±0.01 °2θ; or at 26.6 °2θ). In some embodiments, said powder X-ray diffraction pattern is obtained using Cu Kα1 X-rays at a wavelength of 1.5406 Å.

In another aspect, the present disclosure provides a crystalline Form (i.e., "Form E") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 10.9 (e.g., at 10.9±0.20 °2θ; at 10.9±0.15 °2θ; at 10.9±0.10 °2θ; at 10.9±0.05 °2θ; at 10.9±0.01 °2θ; or at 10.9 °2θ) and/or about 26.5 (e.g., at 26.5±0.20 °2θ; at 26.5±0.15 °2θ; at 26.5±0.10 °2θ; at 26.5±0.05 °2θ; at 26.5±0.01 °2θ; or at 26.5 °2θ). In some embodiments, said powder X-ray diffraction pattern is obtained using Cu Kα1 X-rays at a wavelength of 1.5406 Å.

In another aspect, the present disclosure provides a crystalline Form (i.e., "Form F") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 15.0 (e.g., at 15.0±0.20 °2θ; at 15.0±0.15 °2θ; at 15.0±0.10 °2θ; at 15.0±0.05 °2θ; at 15.0±0.01 °2θ; or at 15.0 °2θ) and/or about 22.8 (e.g., at 22.8±0.20 °2θ; at 22.8±0.15 °2θ; at 22.8±0.10 °2θ; at 22.8±0.05 °2θ; at 22.8±0.01 °2θ; or at 22.8

°2θ). In some embodiments, said powder X-ray diffraction pattern is obtained using Cu Kα1 X-rays at a wavelength of 1.5406 Å.

In another aspect, the present disclosure provides a crystalline Form (i.e., "Form G") of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide wherein said form has an X-ray diffraction pattern comprising a peak at a diffraction angle (2θ) of about 22.8 (e.g., at 22.8±0.20 °2θ; at 22.8±0.15 °2θ; at 22.8±0.10 °2θ; at 22.8±0.05 °2θ; at 22.8±0.01 °2θ; or at 22.8 °2θ). In some embodiments, said powder X-ray diffraction pattern is obtained using Cu Kα1 X-rays at a wavelength of 1.5406 Å.

In some embodiments, the present disclosure provides a mixture comprising a crystalline form (e.g., Form A) and further comprising one or more additional morphic forms. In some embodiments, the mixture comprises Form A and Form B; in some embodiments, the mixture comprises Form A and Form C; in some embodiments, the mixture comprises Form A and Form D; in some embodiments, the mixture comprises Form A and Form E; in some embodiments, the mixture comprises Form A and Form F; in some embodiments, the mixture comprises Form A and Form G. In some embodiments, the mixture comprises Form A and more than one additional morphic form selected from Form B, C, D, E, F and G.

In another aspect, the present disclosure provides a pharmaceutical composition comprising a crystalline form (e.g., Form A) of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide and a pharmaceutically acceptable carrier. In some embodiments, the pharmaceutical composition further comprises Form B. In some embodiments, the pharmaceutical composition further comprises Form C. In some embodiments, the pharmaceutical composition further comprises Form D. In some embodiments, the pharmaceutical composition further comprises Form E. In some embodiments, the pharmaceutical composition further comprises Form F. In some embodiments, the pharmaceutical composition further comprises Form G.

In another aspect, the present disclosure provides a method of treating a viral infection in a subject in need thereof, comprising administering to the subject a therapeutically effective amount of a crystalline form (e.g., Form A) of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide. In some embodiments, the method comprises administering Form A, B, C, D, E, F and/or G.

In another aspect, the present disclosure provides the use of crystalline form (e.g., Form A) of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide in the manufacture of a medicament for the treatment of a viral infection. In some embodiments, Form A, B, C, D, E, F and/or G is used.

In another aspect, the present disclosure provides the use of crystalline form (e.g., Form A) of 4-amino-7-((2R,3R,4S, 5R)-3,4-dihydroxy-5-(hydroxymethyl) tetrahydrofuran-2-yl)-2-methyl-7H-pyrrolo[2,3-d]pyrimidine-5-carboxamide for the treatment of a viral infection. In some embodiments, Form A, B, C, D, E, F and/or G is used.

In some embodiments, the crystalline Form A has X-ray diffraction pattern comprising peaks at a diffraction angle (2θ) of about 23.2 and/or 26.5. In some embodiments, the crystalline Form A has an X-ray diffraction pattern comprising X-peaks at a diffraction angle (2θ) of about 10.7, 11.6, 12.2, 15.3, and/or 18.6.

In some embodiments, the crystalline Form A is further characterized by an endothermic peak at about 231° C. as measured by differential scanning calorimetry. In some embodiments, the endothermic peak represents an energy input of about 173 J/g.

In some embodiments, the crystalline Form A is further characterized by a mass loss of about 2.4% between a temperature of about 110° C. and 220° C. as measured by thermogravimetric analysis.

In some embodiments, the crystalline Form A is further characterized by a PXRD pattern substantially similar to that set forth in FIG. 1A. In some embodiments, the crystalline Form A is further characterized by a PXRD pattern substantially similar to that set forth in FIG. 1B.

In some embodiments, the crystalline Form A is further characterized by a TG-FTIR profile substantially similar to that set forth in FIG. 8. In some embodiments, the crystalline Form A is further characterized by a DSC profile substantially similar to that set forth in FIG. 15.

In some embodiments, the crystalline Form A is further characterized by a DVS profile substantially similar to that set forth in FIG. 20A. In some embodiments, the crystalline Form A is characterized by a DVS profile substantially similar to that set forth in FIG. 20B.

In some embodiments, the crystalline Form A is substantially non-hygroscopic.

In some embodiments, the crystalline Form A is recrystallized from a solvent having a water activity of at least about 0.2.

In some embodiments, the crystalline 4-amino-7-((2R,3R, 4S,5R)-3,4-dihydroxy-5-(hydroxymethyl) tetrahydrofuran-2-yl)-2-methyl-7H-pyrrolo[2,3-d]pyrimidine-5-carboxamide (e.g., Form A) is used to treat a viral infection selected from norovirus, human cytomegalovirus, BK virus, Epstein-Barr virus, adenovirus, JC virus, SV40, MC virus, KI virus, WU virus, vaccinia, herpes simplex virus 1, herpes simplex virus 2, human herpes virus 6, human herpes virus 8, hepatitis B virus, hepatitis C virus, varicella zoster virus, variola major, variola minor, smallpox, cowpox, camelpox, monkeypox, poliovirus, picornaviridae, paramyxoviridae, ebola virus, Marburg virus, influenza, enterovirus, papilloma virus, West Nile virus, yellow fever virus, foot-and-mouth disease virus, Rift Valley fever virus, and other flavivirus, arenavirus, bunyavirus, alphavirus, human immunodeficiency virus, and any combination thereof. In some embodiments, the viral infection is norovirus. In some embodiments, a compound and/or morphic form (e.g., Form A) is used in the manufacture of a medicament for the treatment of one of the above-viral infections. In some embodiments, a compound and/or morphic form (e.g., Form A) is used for the treatment of one of the above-viral infections. In some embodiments, the present disclosure teaches a compound and/or morphic Form (e.g., Form A) for use in treating any one of the above-viral infections.

In another aspect, the present disclosure provides a method of preparing a crystalline hemihydrate form of 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide comprising: recrystallizing the 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide from a solvent system comprising 1-propanol and 0.01 M aqueous NaOH. In some embodiments, the solvent system comprises 1-propanol and 0.01 M aqueous NaOH at a volume ratio of 1:2.

In some embodiments, the 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide is dissolved in the solvent system comprising 1-propanol and 0.01 M aqueous NaOH at a temperature of about 90° C. to produce a solution. In some embodiments, the solution is cooled to about 80° C. and stirred (e.g., for about an hour).

In some embodiments, the solution is seeded with Compound 1, Form A, for example at a temperature of about 80° C. In some cases, the solution can be seeded before the solution is cooled (e.g., to about 80° C.). In some cases, the solution can be seeded after the solution is cooled (e.g., to about 80° C.). In some cases, the solution is not seeded. In some embodiments, the seed comprises about 1% of the amount of Compound 1 in the solution.

In some embodiments, the solution is further cooled to a temperature of about 5° C. In some embodiments, the solution is stirred at about 5° C. for about 4 hours. In some embodiments, the cooling rate is about 5K/hour. In some embodiments, cooling the solution can result in a suspension (e.g., comprising solid crystalline Compound 1 (e.g., Form A)). In some embodiments, the suspension is filtered to isolate the crystalline Compound 1 (e.g., Form A).

In some embodiments, the crystallized 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide is further washed with water. In some embodiments, the crystallized 4-amino-7-((2R,3R,4S,5R)-3,4-dihydroxy-5-(hydroxymethyl) tetrahydrofuran-2-yl)-2-methyl-7H-pyrrolo[2,3-d]pyrimidine-5-carboxamide is over 99% pure.

DETAILED DESCRIPTION OF THE INVENTION

Figure 1A:
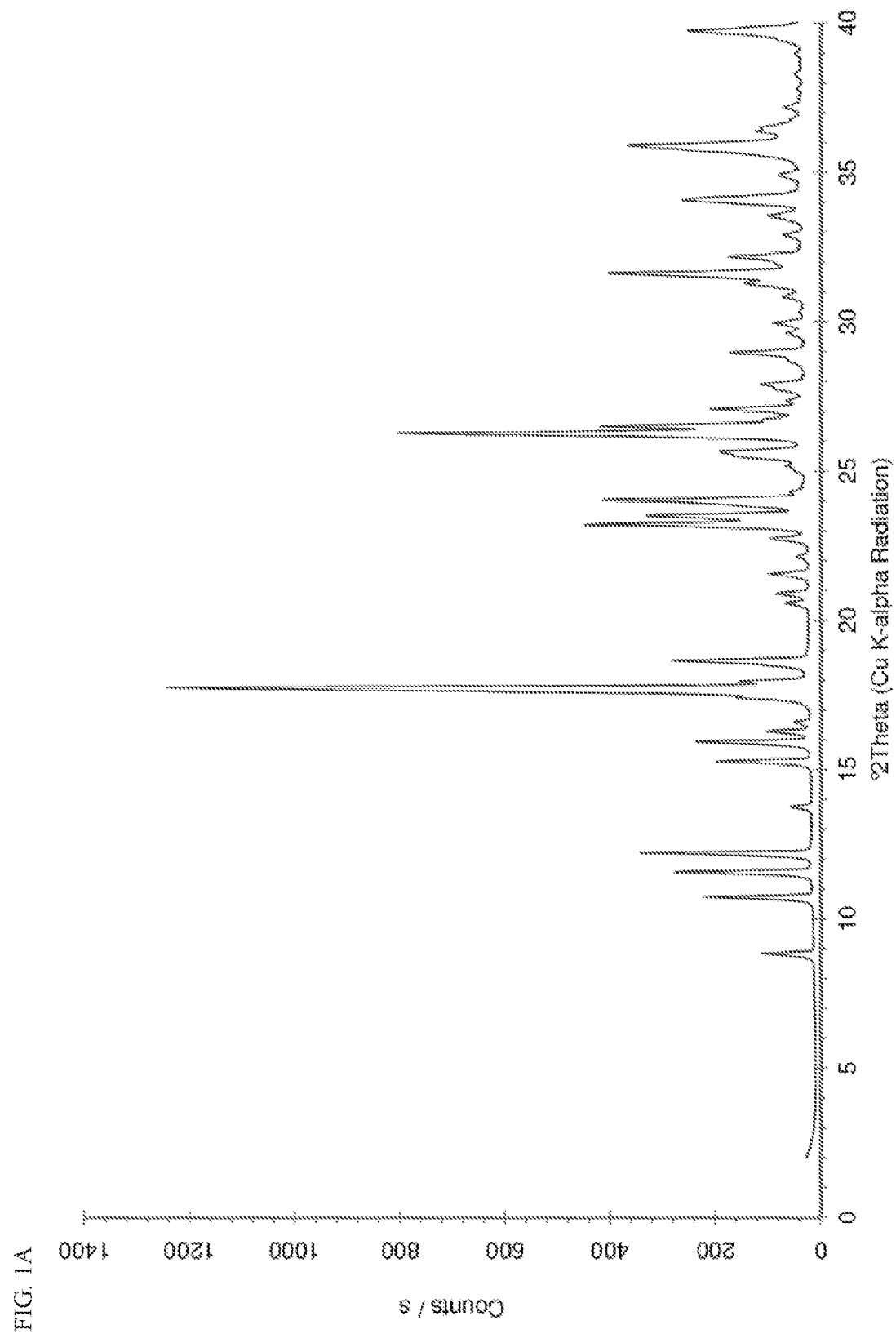
FIG. 1A is a PXRD pattern of a sample of Compound 1, Form A taken in reflection geometry.

As set forth herein, Compound 1 is an antiviral agent that is effective against a number of viral indications. This disclosure provides stable morphic forms of Compound 1 that can be used as pharmaceutical agents. In some embodiments, one or more morphic forms (e.g., Form A) can be formulated into a pharmaceutical composition.

Definitions

"ORTEP" is understood to mean Oak Ridge Thermal Ellipsoid Plot.

"PXRD" is understood to mean powder X-ray diffraction. Unless otherwise specified, all PXRD peaks and patterns are given in °2θ using Cu Kα1 radiation at a wavelength of 1.5406 Å.

"Preferred orientation effects" refer to variable peak intensities or relative intensity differences between different PXRD measurements of the same samples that can be due to the orientation of the particles. Without wishing to be bound by theory, in PXRD it can be desirable to have a sample in which particles are oriented randomly (e.g., a powder). However, it can be difficult or in some cases impossible to achieve truly random particle orientations in practice. As particle size increases, the randomness of particle orientation can decrease, leading to increased challenges with achieving a preferred orientation. Without wishing to be bound by theory, a smaller particle size can reduce technical challenges associated with preferred orientation and allow for more accurate representation of peaks. However, one of skill in the art will understand how to reduce or mitigate preferred orientation effects, and will recognize preferred orientation effects that can exist even between two different measurements of the same sample. For instance, in some embodiments, differences in resolution or relative peak intensities can be attributed to preferred orientation effects.

As used herein, the term "treat," "treating," or "treatment" herein, is meant decreasing the symptoms, markers, and/or any negative effects of a condition in any appreciable degree in a patient who currently has the condition. In some embodiments, treatment can be administered to a subject who exhibits only early signs of the condition for the purpose of decreasing the risk of developing the disease, disorder, and/or condition (e.g., a viral indication).

As used herein, the term "prevent," "prevention," or "preventing" refers to any method to partially or completely preclude or delay the onset of one or more symptoms or features of a disease, disorder, and/or condition. Prevention treatment can be administered to a subject who does not exhibit signs of a disease, disorder, and/or condition. Prevention can apply to subjects who are at risk of developing or acquiring a certain disease. For instance, a subject can be at risk of developing or acquiring a certain disease when they are in close proximity to others who suffer from (e.g., exhibit symptoms of) the disease. That is, one can be exposed to a disease by being in close proximity to another individual who suffers from a disease and thus increase one's risk of acquiring the disease. For example, hospital workers can be at risk of developing or acquiring a certain disease when treating others who suffer from the disease. Hospital patients can also be at risk of developing or acquiring a disease from other patients who suffer from the disease. Accordingly, a compound and/or form disclosed herein can be used for the prevention of a disease in subjects who are spending extended periods of time in close contact with others. For example, norovirus can be spread when individuals are in close contact to one or more persons suffering from norovirus, such as aboard a cruise ship, at an amusement park, on a college campus, or at the Olympic village. Likewise, for instance, influenza can be spread when individuals are in close contact to one or more persons suffering from influenza (e.g., aboard an airplane).

The term "therapeutically effective amount", as used herein, refers to an amount of a pharmaceutical agent to treat or ameliorate an identified disease or condition, or to exhibit a detectable therapeutic effect. The effect can be detected by any assay method known in the art. The precise therapeutically effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

The term "prophylactically effective amount", as used herein, refers to an amount of a pharmaceutical agent to prevent or delay onset of an identified disease or condition, or to exhibit a detectable inhibitory effect. A prophylactically effective amount can provide prophylaxis for an identified disease or condition. The effect can be detected by any assay method known in the art. The precise prophylactically effective amount for a subject will depend upon the subject's body weight, size, and health; the nature and extent of the condition; and the therapeutic or combination of therapeutics selected for administration. Prophylactically effective amounts for a given situation can be determined by routine experimentation that is within the skill and judgment of the clinician.

As used herein, "subject" means a human or animal (in the case of an animal, the subject can be a mammal). In one aspect, the subject is a human. In one aspect, the subject is a male. In one aspect, the subject is a female.

The term "about" is used herein to mean approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 20%. When used in the context of XRPD peak values, the term "about" can indicate a peak value±0.20; ±0.15; ±0.10; ±0.05; or ±0.01 °2θ. In some embodiments, when used in the context of XRPD peak values "about" can indicate a peak value at substantially exactly the disclosed peak value.

Compounds of the Disclosure

Formula 1

As used herein, "Formula I" is understood to encompass all diastereomers of 4-amino-7-(3,4-dihydroxy-5-(hydroxymethyl)tetrahydrofuran-2-yl)-2-methyl-7H-pyrrolo[2,3-d]pyrimidine-5-carboxamide, and pharmaceutically acceptable salts and solvates thereof. The structure of Formula I is shown below:

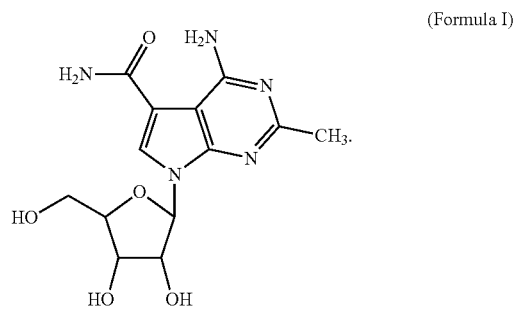 [SMILES: Cc1nc(N)c2c(C(N)=O)cn(C3OC(CO)C(O)C3O)c2n1]

(Formula I)

In some embodiments, a compound of Formula I can be 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide ("Compound 1"), or a pharmaceutically acceptable salt solvate, or isomers (e.g., enantiomers and diastereomers) thereof. The structure of Compound 1 is shown below:

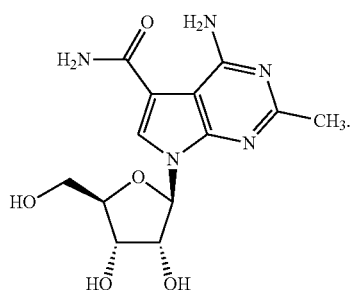

(Compound 1)

As set forth below, an investigation of the polymorphic forms of Compound 1 identified seven unique morphic forms, identified as Form A, Form B, Form C, Form D, Form E, Form F, and Form G. Characterization data for each of the morphic forms is given below. Without wishing to be bound by theory, Form A was found to be the most stable and least hygroscopic of the forms identified.

Exemplary acid addition salts for incorporation with Compound 1 (e.g., Compound 1 Form A) include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto. In some embodiments, Formula I encompasses a hydrochloride salt of Compound 1.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention.

Form A

Form A of Compound 1 was characterized as a hemihydrate morphic form of Compound 1. Morphic Form A of compound 1 can be prepared by crystallization from a number of organic solvent/water mixtures. The solvent/water mixtures can have various water activities. For example, morphic Form A was recovered from solvent systems that had a water activity of at least 0.2. In some embodiments, morphic Form A was recovered from solvent systems that had a water activity of 0.18. Accordingly, the present disclosure presents a method of preparing morphic Form A of Compound 1 comprising recrystallizing from a solvent system with a water activity of at least 0.18 (e.g., 0.19, 0.20, 0.21, 0.22, 0.23, 0.24, 0.25, or above 0.25). For instance, recrystallization from water; THF:water 1:1; acetone:water 4:1; DMA:water 1:1; DMF:water 1:1; DMSO:water 1:1; methanol:water 9:1; and methanol:water 95:5 were all found to yield morphic Form A. The final temperature of the recrystallization solvents can be room temperature (e.g., about 25° C.).

Other morphic Forms described herein (e.g., Form B and Form E) were found to convert to morphic Form A under appropriate conditions (e.g., at room temperature, about 25° C.). For example, Forms B and E transformed into Form A at about 25° C. and above about 50% relative humidity (e.g., during water vapor sorption experiments).

Figure 1B:
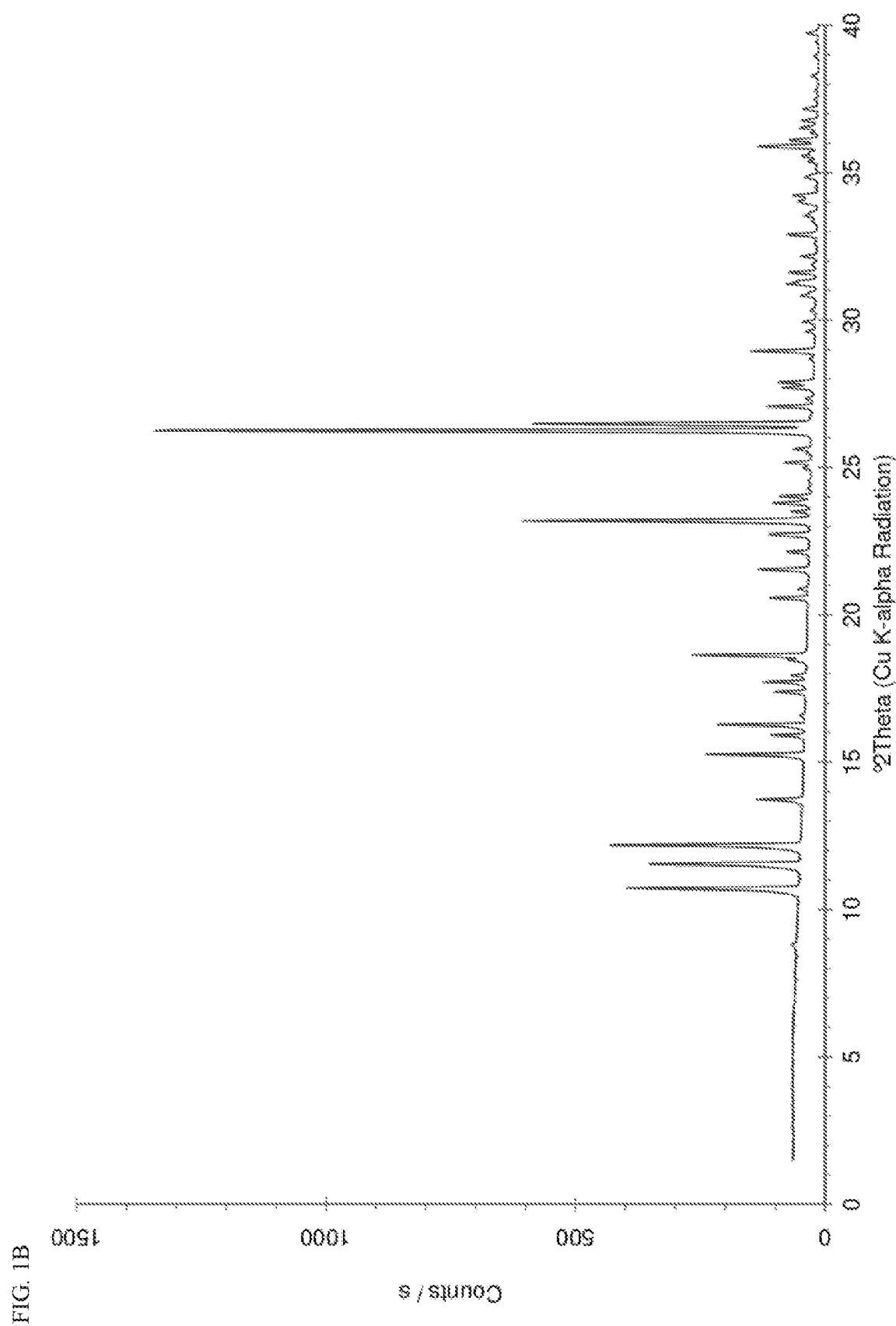
FIG. 1B is a PXRD pattern of a sample of Compound 1, Form A taken in transmission geometry.

Two unique PXRD patterns are shown in FIG. 1A and FIG. 1B, respectively. FIG. 1A is a PXRD pattern of a sample of Compound 1, Form A taken in reflection mode. FIG. 1A was obtained using a Bruker D8 Advance powder X-ray diffractometer using Cu Kα radiation and Bragg-Brentano reflection geometry. FIG. 1B is a PXRD pattern of a sample of Compound 1, Form A taken in transmission mode. FIG. 1B was obtained using a Stoe Stadi P powder X-ray diffractometer using Cu Kα1 radiation and transmission geometry. As shown in FIG. 1A and FIG. 1B, the main differences between the two patterns are the relative intensities of the peaks. Without wishing to be bound by theory, the differences in the relative intensities can be due to preferred orientation effects (i.e., different particle shapes and/or sizes).

In some embodiments, morphic Form A can be characterized by the PXRD peaks set forth below in Table 1. For example, morphic Form A can be characterized by a PXRD peak at about 26.2 °2θ (e.g., 26.2±0.2 °2θ; 26.2±0.1 °2θ; or 26.2±0.0 °2θ; Cu Kα1 radiation). Form A can further be characterized by PXRD peaks at about 23.2 °2θ and/or 26.5 °2θ (e.g., ±0.2 °2θ, ±0.1 °2θ, or ±0.0 °2θ; Cu Kα1 radiation). Form A can be further characterized by PXRD peaks at about 10.7 °2θ, 11.6 °2θ, 12.2 °2θ, 15.3 °2θ, and/or 18.6 °2θ (e.g., ±0.2 °2θ, ±0.1 °2θ, or ±0.0 °2θ; Cu Kα1 radiation).

In some embodiments, Form A can be characterized by PXRD peaks at about 26.2 °2θ and about 23.2 °2θ (e.g., ±0.2 °2θ, ±0.1 °2θ, or ±0.0 °2θ; Cu Kα1 radiation). In some embodiments, Form A can be characterized by PXRD peaks at about 26.2 °2θ and about 26.5 °2θ (e.g., ±0.2 °2θ, ±0.1 °2θ, or ±0.0 °2θ; Cu Kα1 radiation). In some embodiments, Form A can be characterized by PXRD peaks at about 26.2 °2θ, 23.2 °2θ, and about 26.5 °2θ (e.g., ±0.2 °2θ, ±0.1 °2θ, or ±0.0 °2θ; Cu Kα1 radiation).

In some embodiments, Form A can be characterized by PXRD peaks at about 10.7 °2θ, about 26.2 °2θ, about 23.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 11.6 °2θ, about 26.2 °2θ, about 23.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 12.2 °2θ, about 26.2 °2θ, about 23.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 15.3 °2θ, about 26.2 °2θ, about 23.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 18.6 °2θ, about 26.2 °2θ, about 23.2 °2θ, and about 26.5 °2θ (e.g., ±0.2 °2θ, ±0.1 °2θ, or ±0.0 °2θ; Cu Kα1 radiation).

In some embodiments, Form A is characterized by PXRD peaks at about 15.9 °2θ and about 23.8 °2θ (e.g., ±0.2 °2θ, ±0.1 °2θ, or ±0.0 °2θ; Cu Kα1 radiation).

In some embodiments, Form A is characterized by PXRD peaks at about 10.7 °2θ, about 11.6 °2θ, and about 12.2 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, and about 15.3 °2θ (e.g., ±0.2 °2θ, ±0.1 °2θ, or ±0.0 °2θ; Cu Kα1 radiation). In some embodiments, Form A is characterized by a single peak at about 11.6 °2θ (e.g., ±0.2 °2θ, ±0.1 °2θ, or ±0.0 °2θ; Cu Kα1 radiation).

In some embodiments, Form A is characterized by PXRD peaks at about 10.7 °2θ, about 11.6 °2θ, about 12.2 °2θ, about 15.3 °2θ, and about 15.9 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, and about 16.3 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, about 15.9 °2θ and about 16.3 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, and about 18.6 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, about 15.9 °2θ, about 16.3 °2θ and about 18.6 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, about 15.9 °2θ, and about 18.6 °2θ (e.g., ±0.2 °2θ, ±0.1 °2θ, or ±0.0 °2θ; Cu Kα1 radiation). In some embodiments, Form A is characterized by PXRD peaks at about 10.7 °2θ, about 11.6 °2θ, about 12.2 °2θ, about 15.3 °2θ, about 16.3 °2θ and about 18.6 °2θ (e.g., ±0.2 °2θ, ±0.1 °2θ, or ±0.0 °2θ; Cu Kα1 radiation).

In some embodiments, Form A can be characterized by PXRD peaks at about 10.7 °2θ, about 23.2 °2θ, about 26.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 10.7 °2θ, about 11.6 °2θ, about 23.2 °2θ, about 26.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 10.7 °2θ, about 11.6 °2θ, about 12.2 °2θ, about 23.2 °2θ, about 26.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 10.7 °2θ, about 11.6 °2θ, about 12.2 °2θ, about 15.3 °2θ, about 23.2 °2θ, about 26.2 °2θ, and about 26.5 °2θ (e.g., ±0.2 °2θ, ±0.1 °2θ, or ±0.0 °2θ; Cu Kα1 radiation). In some embodiments, Form A can be characterized by PXRD peaks at about 10.7 °2θ, about 11.6 °2θ, about 12.2 °2θ, about 15.3 °2θ, about 18.6 °2θ, about 23.2 °2θ, about 26.2 °2θ, and about 26.5 °2θ (e.g., ±0.2 °2θ, ±0.1 °2θ, or ±0.0 °2θ; Cu Kα1 radiation).

Accordingly, in some embodiments, morphic Form A is characterized by one, two, three, four, five, six, seven or eight peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by one peak selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by two peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by three peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by four peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by five peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by six peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by seven peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation). In some embodiments, morphic Form A is characterized by eight peaks selected from about 10.7, 11.6, 12.2, 15.3, 18.6, 23.2, 26.2, and 26.5 °2θ (e.g., ±0.2 °2θ, ±0.1 °2θ, or ±0.0 °2θ; Cu Kα1 radiation).

TABLE 1

Representative PXRD Peaks for Morphic Form A (Cu Kα1 radiation)

| Angle (°2θ) | d value (Å) | Intensity |
|---|---|---|
| 8.8 | 10.02 | vw |
| 10.7 | 8.26 | m |
| 11.6 | 7.66 | m |
| 12.2 | 7.26 | m |
| 13.7 | 6.44 | w |
| 15.3 | 5.80 | m |
| 15.9 | 5.57 | w |
| 16.3 | 5.44 | w |
| 16.6 | 5.35 | vw |
| 17.4 | 5.10 | vw |
| 17.7 | 5.00 | w |
| 17.9 | 4.94 | vw |
| 18.5 | 4.80 | vw |
| 18.6 | 4.76 | m |
| 20.6 | 4.31 | w |
| 20.9 | 4.25 | vw |
| 21.5 | 4.12 | w |
| 22.1 | 4.01 | vw |
| 22.7 | 3.91 | w |
| 23.2 | 3.83 | s |
| 23.5 | 3.78 | vw |
| 23.8 | 3.74 | w |
| 24.0 | 3.70 | vw |
| 24.3 | 3.66 | vw |
| 25.0 | 3.56 | vw |
| 25.2 | 3.54 | vw |
| 25.6 | 3.47 | vw |
| 26.2 | 3.39 | vs |
| 26.5 | 3.36 | s |
| 27.1 | 3.29 | w |
| 27.3 | 3.26 | vw |
| 27.7 | 3.22 | vw |
| 27.9 | 3.20 | w |
| 28.7 | 3.11 | vw |
| 28.9 | 3.08 | w |
| 29.6 | 3.01 | vw |
| 29.9 | 2.98 | vw |
| 30.3 | 2.95 | vw |
| 30.8 | 2.90 | vw |

TABLE 1-continued

Representative PXRD Peaks for Morphic
Form A (Cu Kα1 radiation)

| Angle (°2θ) | d value (Å) | Intensity |
|---|---|---|
| 31.2 | 2.86 | vw |
| 31.6 | 2.83 | vw |
| 31.9 | 2.80 | vw |
| 32.2 | 2.78 | vw |
| 32.9 | 2.72 | vw |
| 33.5 | 2.67 | vw |
| 34.0 | 2.63 | vw |
| 34.2 | 2.62 | vw |
| 34.8 | 2.57 | vw |
| 35.4 | 2.54 | vw |
| 35.6 | 2.52 | vw |
| 35.9 | 2.50 | w |
| 36.1 | 2.49 | vw |
| 36.5 | 2.46 | vw |
| 36.8 | 2.44 | vw |
| 37.2 | 2.42 | vw |
| 37.8 | 2.38 | vw |
| 38.3 | 2.35 | vw |
| 38.5 | 2.34 | vw |
| 39.0 | 2.31 | vw |
| 39.7 | 2.27 | vw |

Figure 8:
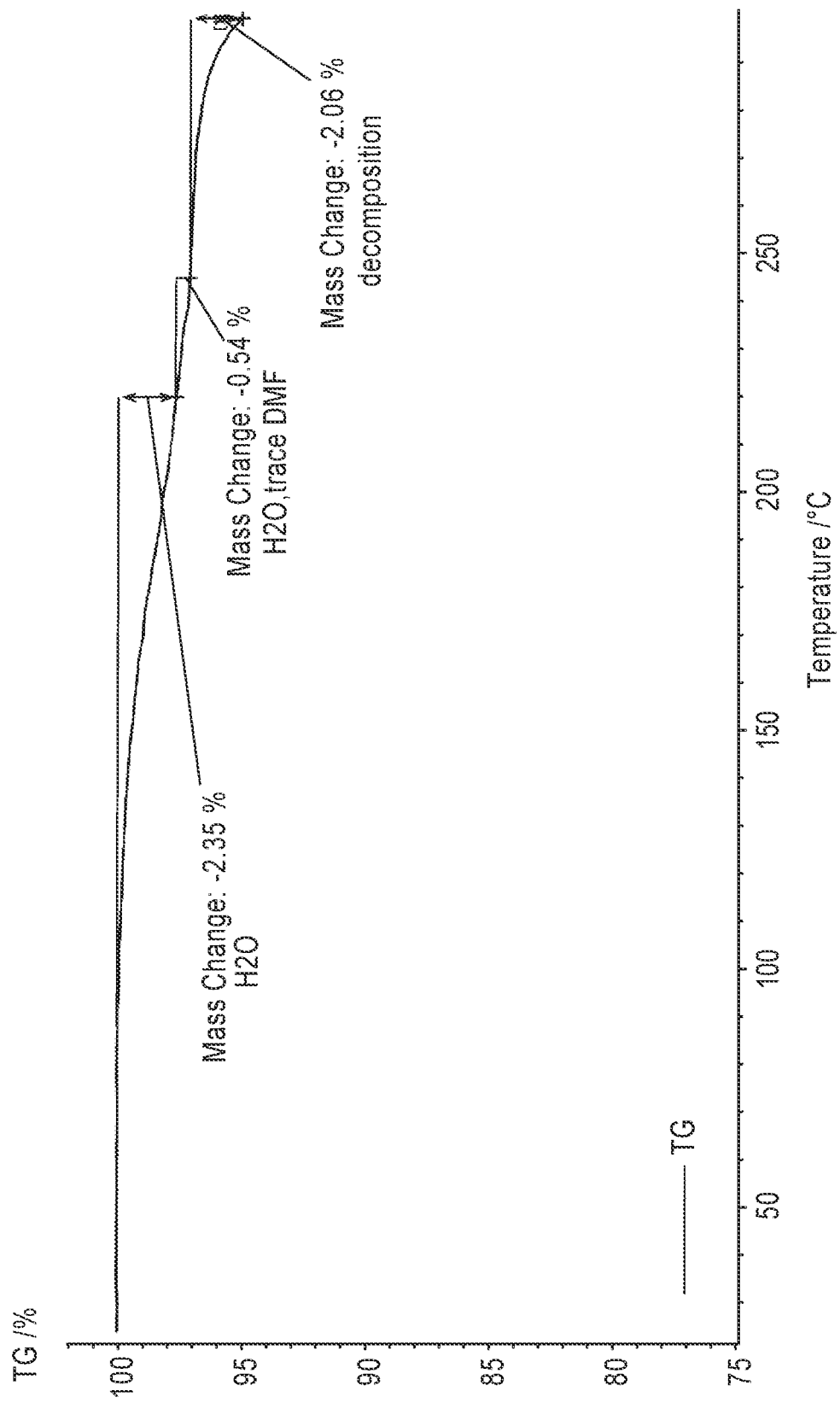
FIG. 8 is a TG-FTIR diagram of a sample of Compound 1, Form A.

FIG. 8 is a TG-FTIR diagram of a sample of Compound 1, Form A. FIG. 8 was obtained using a Netzsch TG 209, over the range of 25° C. to 300° C. The scanning speed was 10° C. per minute. FIG. 8 shows a mass loss step between about 110° C. and about 220° C. of about 2.4% (e.g., about 2.35%). Without wishing to be bound by theory, this mass loss can be attributable to a loss of water. In some embodiments, Form A is characterized by a mass loss of about 2.4% between about 110° C. and about 220° C. (e.g., as measured by TG-FTIR). FIG. 8 shows a second mass loss step between about 220° C. and about 245° C. of about 0.5% (e.g., about 0.54%). Without wishing to be bound by theory, this mass loss step can be attributed to the loss of additional water and trace amounts of DMF. In some embodiments, Form A is characterized by a mass loss of about 0.5% between about 220° C. and about 245° C.

Without wishing to be bound by theory, the amount of water lost is very close to the theoretical water content of about 2.7% (e.g., about 2.71%) for a hemihydrate, further providing support that morphic Form A is a hemihydrate. Moreover, without wishing to be bound by theory, the high temperature necessary for dehydration suggests that water is strongly bound in the crystalline lattice of Form A, which suggests a very stable hemihydrate. Accordingly, in some embodiments, the present disclosure provides a morphic form (e.g., a hemihydrate form) of Compound 1 that is highly stable. In some embodiments, the water content of Form A is about 2.4% (w/w) or about 2.7 (w/w).

Figure 15:
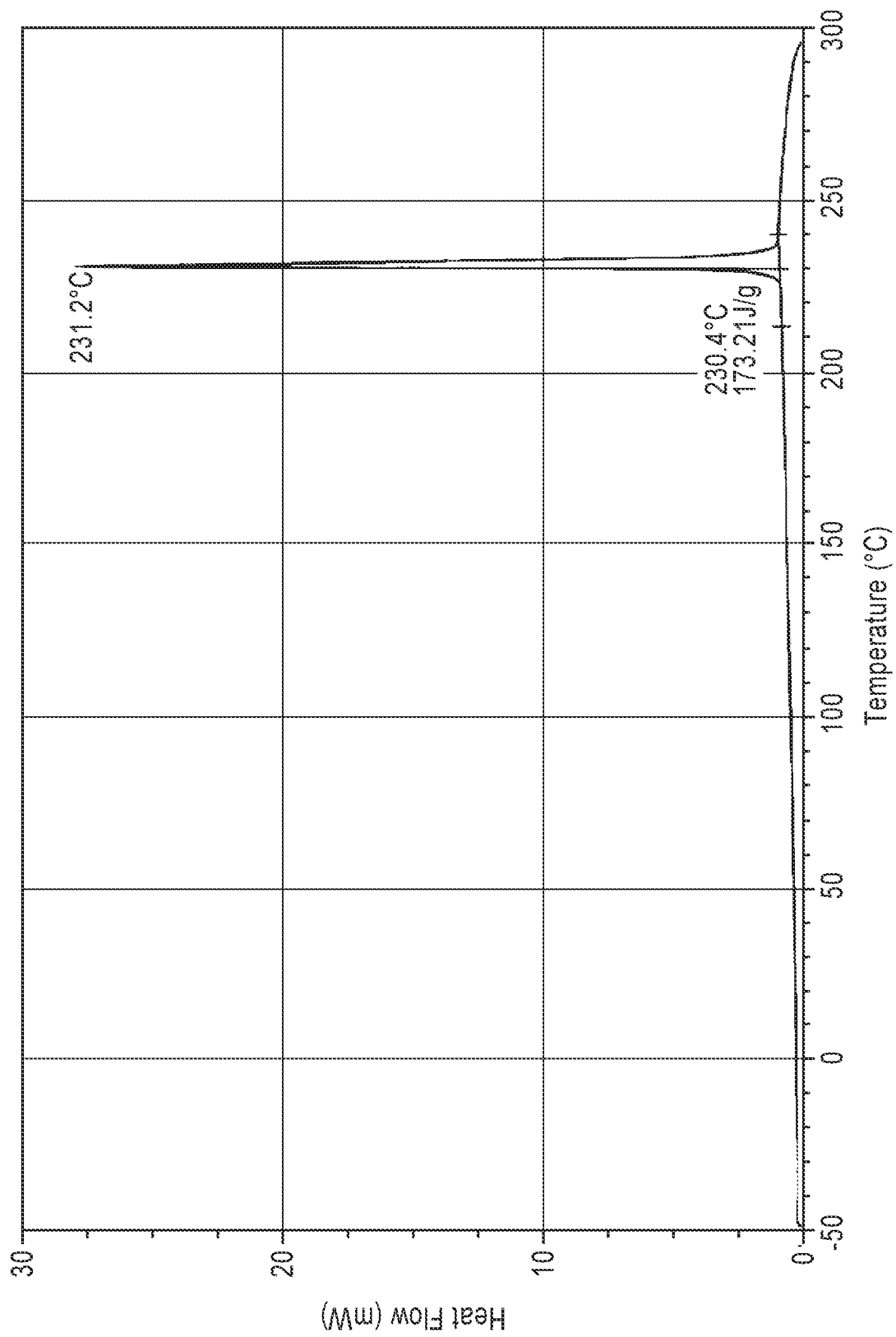
FIG. 15 is a DSC diagram of a sample of Compound 1, Form A.

FIG. 15 is a DSC diagram of a sample of Compound 1, Form A. FIG. 15 was obtained using a DSC Q2000 V24.3 with a hermetically closed gold sample pan. The heating rate was 10° C. per minute. As shown in FIG. 15, Form A revealed an endothermal peak with a peak temperature of about 231° C. (173 J/g) (e.g., about 231.2° C. (173.21 J/g)). Accordingly, in some embodiments, Form A is characterized by a DVS curve with an endothermal peak with a peak temperature of about 231° C. (173 J/g). In some embodiments, Form A is characterized by a DVS curve with a single endothermal peak (e.g., at about 231° C. (173 J/g)). In some embodiments, Form A is characterized by a DVS curve with no exothermic peak.

Figure 20A:
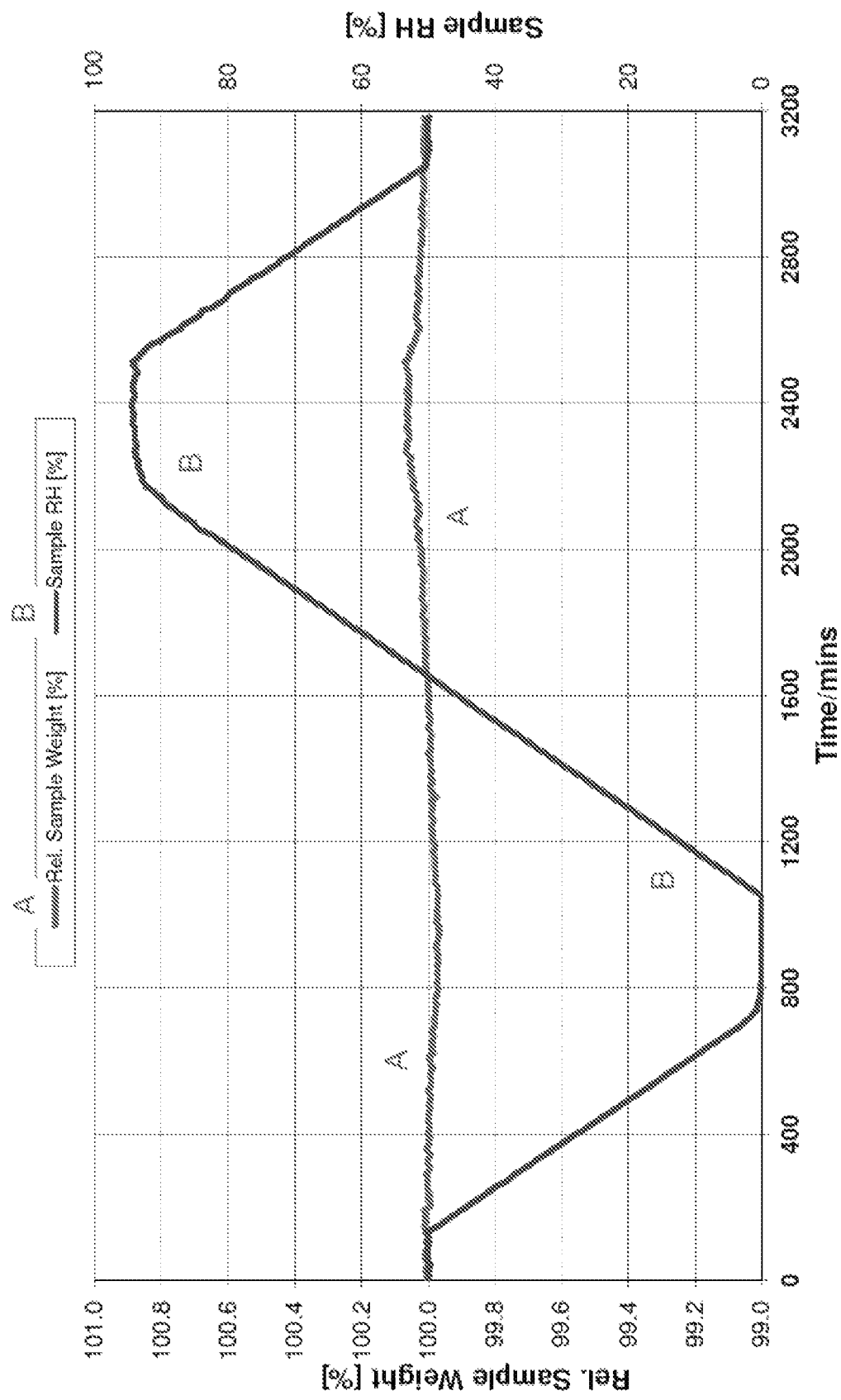
FIG. 20A is a DVS diagram of a sample of Compound 1, Form A as a function of time and the applied change in relative humidity.
Figure 20B:
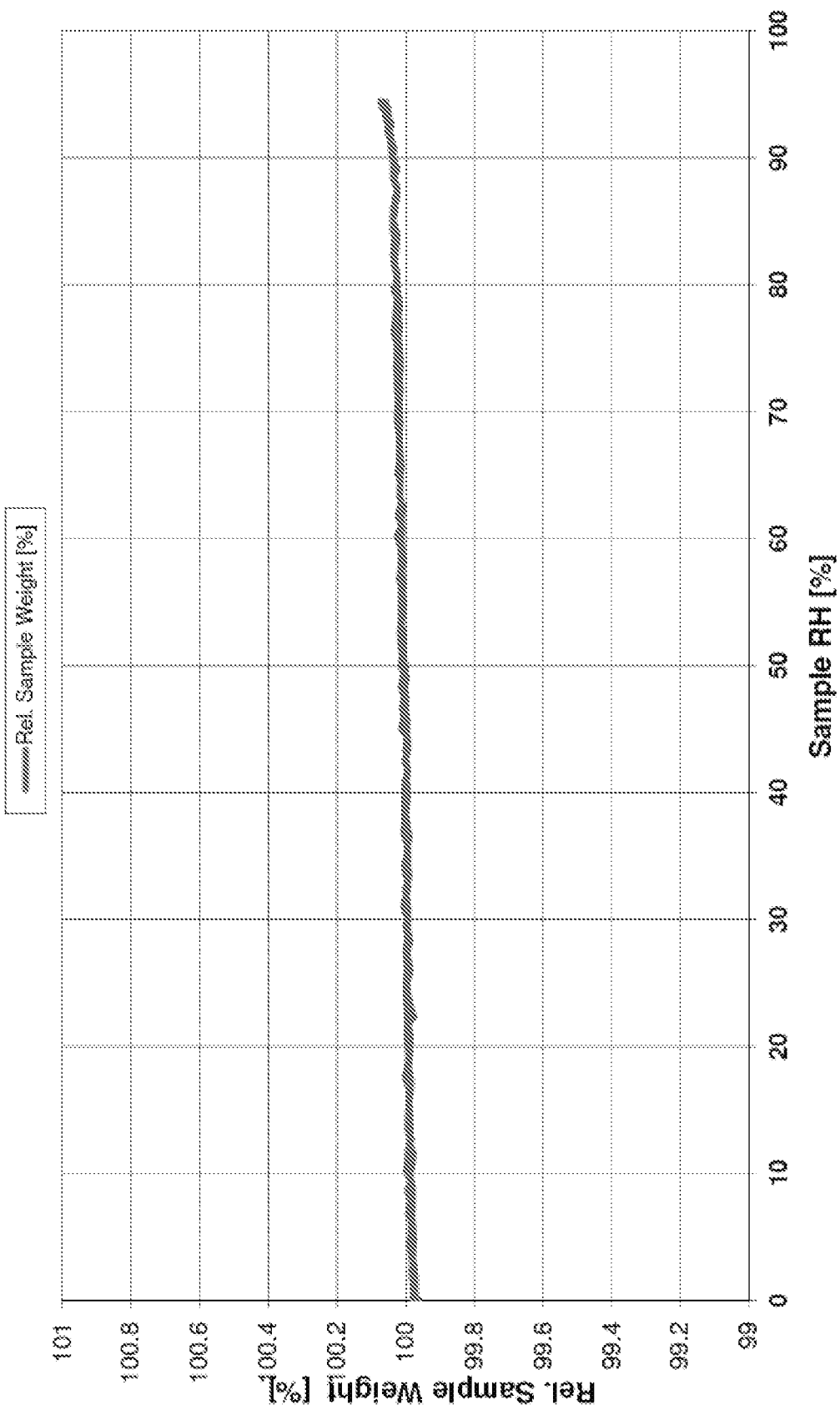
FIG. 20B is a DVS diagram of a sample of Compound 1, Form A as a function of the applied relative humidity.

FIG. 20A is a DVS diagram of a sample of Compound 1, Form A as a function of time and the applied change in relative humidity. Line A represents the relative weight of the sample at each relative humidity. Line B represents the applied relative humidity (i.e., the applied measurement program). FIG. 20B is a DVS diagram of a sample of Compound 1, Form A as a function of the applied relative humidity. FIG. 20A and FIG. 20B were obtained using a Sorptions Prufsystem ProUmid system using a scan rate of 5% relative humidity per hour at a temperature of 25° C.

As shown in FIG. 20A and FIG. 20B, the DVS analysis of Form A showed only small desorption (0% R.H.: ≤0.1% m/m) and adsorption (95% R.H.: ±0.1% m/m) of water. Without wishing to be bound by theory, these data demonstrate that Form A is stable and is non-hygroscopic. Additionally, PXRD measurement of the sample post-DVS showed the same pattern as the sample before DVS. Accordingly, in some embodiments, Form A is non-hygroscopic, and does not convert to other forms in the presence of high relative humidity.

Stability

In some embodiments, morphic Form A is less hygroscopic than other identified morphic forms (e.g., forms B-G). For example, FIG. 20A and FIG. 20B show that Form A showed only small adsorption or desorption of water as a function of relative humidity. In contrast, as shown below, other morphic Forms (e.g., Form B, Form D and Form E) exhibited greater fluctuations in mass as a function of relative humidity, suggesting that these morphic forms are more hygroscopic than Form A. These results also suggest that morphic Form A is the least hygroscopic morphic form of any of the forms identified in this disclosure.

Additionally, as set forth in Example 5, all seven of the morphic forms identified herein (i.e., Form A, Form B, Form C, Form D, Form E, Form F, and Form G) were stirred for four days in a 1:1 mixture of DMF:water; and a 95:5 mixture of methanol:water. After each experiment, PXRD of all of the samples returned only morphic Form A. Accordingly, without wishing to be bound by theory, morphic Form A is the most thermodynamically stable morphic form of all of the morphic forms identified herein.

Single Crystal Structure of the Form A Hemihydrate

The single crystal structure of Form A was elucidated using X-ray diffraction. The data allowed for the absolute configuration to be determined. Without wishing to be bound by theory, the molecule crystallizes in the triclinic space group P1 with two molecules of Compound 1 and one molecule of water in the asymmetric unit. One molecule of water is found in the asymmetric unit together with two molecules of Compound 1, which, without wishing to be bound by theory, likely confirms that the structure is a hemihydrate.

Figure 24:
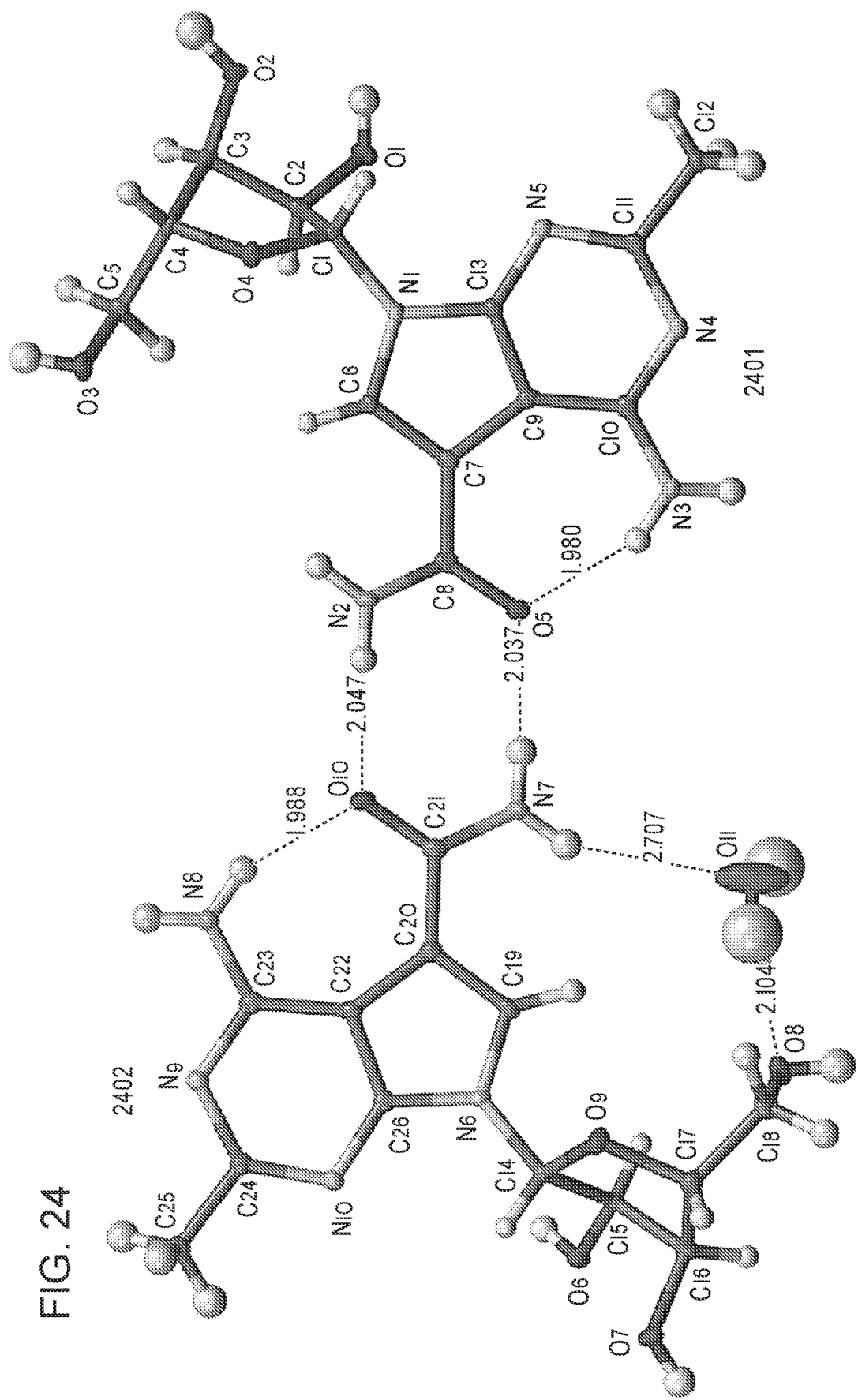
FIG. 24 is an ORTEP plot of the structure of Compound 1, Form A.

FIG. 24 is an ORTEP plot of the structure of Compound 1, Form A. FIG. 24 gives labels for all non-hydrogen atoms. As shown in FIG. 24, a molecule of water is associated with one of the equivalents of Compound 1 (2402) in the asymmetric unit cell. Molecule 2402 is hydrogen-bound to the other molecule of Compound 1 (2401). Referring again to FIG. 24, Bond distances and angles are as expected and all possible hydrogen bond donors and acceptors form hydrogen bonds.

The structure refined without problems and converged at an R-value of 2.24% applying a 2σ cutoff with a weighted R-value using all data of 2.55%. More details about the data collection, the structure solution, and refinement can be found in Table 2, below. The structure is ordered and only the displacement parameters of the water molecule are slightly larger than those for the rest of the atoms in the structure.

TABLE 2

Data Collection of Crystal Structure of Form A

| Formula | $2(C_{13}H_{17}N_5O_5) \cdot H_2O$ |
|---|---|
| Formula weight | 664.63 |
| Z, calculated density | 1, 1.589 Mg*m$^{-3}$ |
| F (000) | 350 |
| Description and size of crystal | Colorless plate, 002*0.13*0.16 mm$^3$ |
| Absorption Coefficient (mm$^{-1}$) | 1.070 |
| Min/max transmission | 0.87/0.98 |
| Temperature (K) | 123 |
| Radiation (wavelength) | CuK$_\alpha$ ($\lambda$ = 1.54178 Å) |
| Crystal System, space group | Triclinic, P1 |
| a/Å | 8.1005(6) |
| b/Å | 8.7599(6) |
| c/Å | 11.1948(8) |
| $\alpha/°$ | 69.537 (2) |
| $\beta/°$ | 69.349(2) |
| $\gamma/°$ | 79.041(3) |
| V/Å$^3$ | 694.60(9) |
| Min/max $\Theta/°$ | 4.434/68.875 |
| Number of collected reflections | 15445 |
| Number of independent reflections | 4651 (merging r = 0.024) |
| Number of observed reflections | 4596 (I > 2$\sigma$ (I)) |
| Number of refined parameters | 489 |
| R | 0.0224 (I > 2$\sigma$ (I)) |
| Rw | 0.0255 (all data) |
| Goodness of fit | 1.1272 |
| Flack parameter | 0.10(9) |
| Min/max density in difference map | −0.16/0.16 |

Exemplary Crystallization Protocol for Preparation of Form A

Example 6 below outlines the development of a robust crystallization process for the preparation of Form A of Compound 1 on an industrially relevant (e.g., 20-g or greater than 20-g) scale. As set forth in Example 6 below, it was found that crystallizing Compound 1 in a solvent system comprising 1-propanol and 0.01 M aqueous NaOH, e.g., at a ratio of 1:2 (v/v) effectively removed common impurities present in an initial sample of Compound 1, Form A. For example, crystallizing from 1-propanol and 0.01 M aqueous NaOH at a ratio of 1:2 (v/v) effectively removed residual benzoic acid and Impurity No. 1 which can be, for example, present in samples of Compound 1, (e.g., Compound 1, Form A) as a result of synthetic process (for example as set forth in U.S. Pat. No. 9,701,706, the contents of which are hereby incorporated by reference in their entirety). Accordingly, crystallizing Compound 1 using a mixture of 1-propanol and 0.01 M aqueous NaOH at a ratio of 1:2 (v/v) can result in highly pure (e.g., greater than 99% pure) samples of Compound 1, Form A. The crystallization conditions were also found to produce Compound 1, Form A in well-formed, plate-like particles, and at a high yield (e.g., 88%). Furthermore, residual content of the solvent (1-propanol) was found to be low (e.g., less than 0.1% m/m) after recrystallizing using a mixture of 1-propanol and 0.01 M aqueous NaOH at a ratio of 1:2 (v/v).

The present disclosure teaches a recrystallization protocol for Compound 1 to give a crystalline form of Compound 1 (e.g., Form A). The present disclosure differs from the teachings of U.S. Pat. No. 9,701,706, which teaches that a suspension of Compound 1 was slurried in water and filtered to give a powder-like solid. As set forth in U.S. Pat. No. 9,701,706, Compound 1 was produced at a purity of 98.84%. As set forth in Example 6, suspension equilibration as taught by U.S. Pat. No. 9,701,706 is not effective to eliminate the main impurities found in crude samples of Compound 1, such as benzoic acid, Impurity No. 1 and Impurity No. 2.

The present disclosure teaches highly pure compositions of Compound 1, for example by purification from 1-propanol and 0.01 M aqueous NaOH at a ratio of 1:2 (v/v). The present disclosure teaches compositions comprising Compound 1 that are greater than 99% pure (e.g., 99.1%, 99.2%, 99.3%, 99.4%, 99.5%, 99.6%, 99.7%, 99.8%, 99.9%, or 99.99%). The present disclosure teaches compositions that contain less than 0.1% benzoic acid (e.g., less than 0.09%, less than 0.08%, less than 0.07%, less than 0.06%, less than 0.05%, less than 0.04%, less than 0.03%, less than 0.02%, or less than 0.01%). The present disclosure also teaches compositions that contain less than 0.1% of Impurity No. 1 (e.g., less than 0.09%, less than 0.08%, less than 0.07%, less than 0.06%, less than 0.05%, less than 0.04%, less than 0.03%, less than 0.02%, or less than 0.01%). The present disclosure teaches compositions that contain less than 1% of Impurity No. 2 (e.g., less than 0.9%, less than 0.8%, less than 0.7%, less than 0.6%, less than 0.5%, less than 0.4%, less than 0.3%, less than 0.2%, or less than 0.1%).

Additionally, morphic Form A can be substantially free of solvent impurities. For example, Form A can be substantially free of methanol (e.g., Form A can contain less than 0.9%, less than 0.8%, less than 0.7%, less than 0.6%, less than 0.5%, less than 0.4%, less than 0.3%, less than 0.2%, or less than 0.1% methanol). For example, Form A can be substantially free of ethanol (e.g., Form A can contain less than 0.9%, less than 0.8%, less than 0.7%, less than 0.6%, less than 0.5%, less than 0.4%, less than 0.3%, less than 0.2%, or less than 0.1% ethanol). For example, Form A can be substantially free of 1-propanol, (e.g., Form A can contain less than 0.9%, less than 0.8%, less than 0.7%, less than 0.6%, less than 0.5%, less than 0.4%, less than 0.3%, less than 0.2%, or less than 0.1% of 1-propanol). Form A can be substantially free of 2-propanol, (e.g., Form A can contain less than 0.9%, less than 0.8%, less than 0.7%, less than 0.6%, less than 0.5%, less than 0.4%, less than 0.3%, less than 0.2%, or less than 0.1% of 2-propanol). For example, Form A can be substantially free of DMSO (e.g., Form A can contain less than 0.9%, less than 0.8%, less than 0.7%, less than 0.6%, less than 0.5%, less than 0.4%, less than 0.3%, less than 0.2%, or less than 0.1% DMSO).

The high purity of the compositions of the present disclosure has advantages over the teachings of U.S. Pat. No. 9,701,706. For example, impurities such as benzoic acid and Impurity Nos. 1 and 2 are undesirable for incorporation in a pharmaceutical composition. For instance, impurities such as benzoic acid and Impurity Nos. 1 and 2 can be toxic, and can cause unwanted side effects when ingested (e.g., as part of a pharmaceutical formulation).

As set forth in Example 6 below, a sample of Compound 1, Form A was found to contain three main impurities left over from the synthetic process (see e.g., U.S. Pat. No. 9,701,706). The impurities were benzoic acid, Impurity No. 1 and Impurity No. 2 (the structures of which are shown below in Example 6). As outlined in Example 6, Compound 1 was dissolved at 90° C. in 1-propanol/0.01M aqueous NaOH (1:2 v/v). The solvent volume for dissolution of 1 g of Compound 1 at 90° C. was 12.5 mL. Without wishing to be bound by theory, this solvent volume can be acceptable for crystal production at an industrial (e.g., greater than 20-g) scale. After cooling to 80° C., the solution became supersaturated and was seeded using 1% m/m of Compound 1, Form A, cooled to 5° C. and filtered. Suspensions thus obtained were found to be easy to stir and easy to filter.

As set forth in Example 6, Compound 1, Form A crystallized in well-formed plate-like particles with a particle size of between about 50 μm and 250 μm at a yield of 88%. The residual content of 1-propanol was less than 0.1% (m/m). Furthermore, crystallization from 1-propanol/0.01M aqueous NaOH (1:2 v/v) effectively removed the impurities of benzoic acid and Impurity No. 1, and partially removed the content of Impurity No. 2.

Accordingly, the present disclosure provides a process for the preparation of Compound 1, Form A comprising recrystallizing Compound 1 using a mixture of 1-propanol and 0.01 M aqueous NaOH, e.g. at a ratio of 1:2 (v/v). In some embodiments, Compound 1 can be dissolved in the mixture of 1-propanol and 0.01 M aqueous NaOH at a ratio of 1:2 (v/v) at a temperature of about 90° C. (e.g., about 110° C.; about 100° C.; about 90° C.; about 80° C.; about 70° C.). In some embodiments, the solution of Compound 1 in the mixture of 1-propanol and 0.01 M aqueous NaOH at a ratio of 1:2 (v/v) can be cooled to about 80° C. (e.g., about 100° C.; about 90° C.; about 80° C.; about 70° C.; about 60° C.). In some embodiments, this cooling results in supersaturation. In some embodiments, the solution of Compound 1 (e.g., the cooled solution) can be seeded with Compound 1, Form A. In some embodiments, the seed crystal is itself suspended in a solution (e.g., water; 1-propanol and 0.01 M aqueous NaOH at a ratio of 1:2 (v/v)). In some embodiments, the seed crystal is about 1% m/m of the amount of Compound 1 dissolved in the 1-propanol and 0.01 M aqueous NaOH at a ratio of 1:2 (v/v). For example, the seed crystal can be about 0.1%, about 0.2%, about 0.3%, about 0.4%, about 0.5%, about 0.6%, about 0.7%, about 0.8%, about 0.9%, about 1.0%, about 2%, about 3%, about 4%, or about 5%). In some embodiments, crystallizing Compound 1 from 1-propanol and 0.01 M aqueous NaOH at a ratio of 1:2 (v/v) can result in a highly pure sample of Compound 1, Form A (e.g., greater than about 90% pure; greater than about 91% pure; greater than about 92% pure; greater than about 93% pure; greater than about 94% pure; greater than about 95% pure; greater than about 96% pure; greater than about 97% pure; greater than about 98% pure; greater than about 99% pure; greater than about 99.9% pure; or greater than about 99.99% pure).

In some embodiments, highly pure Compound 1 (e.g., 99% pure, 99.1% pure, 99.2% pure, 99.3% pure, 99.4% pure, 99.5% pure, 99.6% pure, 99.7% pure, 99.8% pure, 99.9% pure, or 99.99% pure) can be incorporated into a pharmaceutical composition. For example, the pharmaceutical composition can comprise highly pure Compound 1 and a pharmaceutically acceptable carrier.

In some embodiments, the present disclosure provides a method of treatment of a viral infection comprising administering to a subject in need thereof a highly pure sample of Compound 1 (e.g., 99% pure, 99.1% pure, 99.2% pure, 99.3% pure, 99.4% pure, 99.5% pure, 99.6% pure, 99.7% pure, 99.8% pure, 99.9% pure, or 99.99% pure). In some embodiments, the method comprises administering to the subject a pharmaceutical composition comprising a highly pure sample of Compound 1.

In some embodiments, a highly pure sample of Compound 1 (e.g., 99% pure, 99.1% pure, 99.2% pure, 99.3% pure, 99.4% pure, 99.5% pure, 99.6% pure, 99.7% pure, 99.8% pure, 99.9% pure, or 99.99% pure) can be used for the treatment or prevention of a viral infection. In some embodiments, a highly pure sample of Compound 1 (e.g., 99% pure, 99.1% pure, 99.2% pure, 99.3% pure, 99.4% pure, 99.5% pure, 99.6% pure, 99.7% pure, 99.8% pure, 99.9% pure, or 99.99% pure) can be used in the manufacture of a medicament for the treatment or prevention of a viral infection.

In some embodiments, the solution and/or suspension of Compound 1 in the mixture of 1-propanol and 0.01 M aqueous NaOH, e.g. at a ratio of 1:2 (v/v) is stirred. The stirring can be at a rate of about 500 rpm, and can ensure that Compound 1 does not spontaneously crystallize to an appreciable degree before seeding.

As set forth in Example 6, although many crystallization conditions were identified that can produce Form A, 1-propanol and 0.01 M aqueous NaOH at a ratio of 1:2 (v/v) was able to dissolve Compound 1 using less total solvent than other solvent systems tested. In some embodiments, this can enable larger amounts of Compound 1 (e.g., Form A) to be produced or processed per batch of solvent. Additionally, this solvent system was able to dissolve Compound 1 over a broad temperature range, enabling a higher yield of Form A (e.g., 88% or greater) while still maintaining a high (e.g., greater than 99%) purity. Additionally, solutions comprising Compound 1 in 1-propanol and 0.01 M aqueous NaOH at a ratio of 1:2 (v/v) were found to be easy to stir and filter (e.g., did not exhibit extensive stickiness when stirring and filtering). Furthermore, the crystallization was able to remove many of the common impurities (e.g., benzoic acid, Impurity Nos. 1 and 2) that can be found in samples of Compound 1, Form A. Additionally, stirring the solution and/or suspension can ensure that Compound 1 does not spontaneously crystallize to an appreciable degree before seeding, which can ensure higher purity of the resulting morphic form (e.g., Form A). Furthermore, the solvents that are used (i.e., 1-propanol and 0.01 M NaOH are considered class 3 solvents for their low toxicity. That is, according to FDA guidelines, class 3 solvents may be regarded as less toxic and of lower risk to human health. These solvents exhibit no known risk to human health at levels normally accepted in pharmaceuticals. For example, according to FDA guidelines, the acceptable level of 1-propanol is 5,000 ppm. Accordingly, the solvents used are safer than other common organic solvents.

The present disclosure provides a morphic Form A of Compound 1 that has advantages over other forms of Compound 1. For example, Form A can be highly pure; Form A can be more stable than other morphic forms; and Form A can be non-hygroscopic. Preparation of Form A can also be straightforward, as suspensions and/or solutions of Form A can be easy to stir and filter, and Form A can be prepared from substantially non-toxic solvents.

Form B

Morphic Form B of Compound 1 was characterized as a methanol hemisolvate of Compound 1. Morphic Form B can be prepared by crystallization of Compound 1 from methanol (e.g., substantially pure methanol) by cooling a solution of Compound 1 in methanol.

Figure 2A:
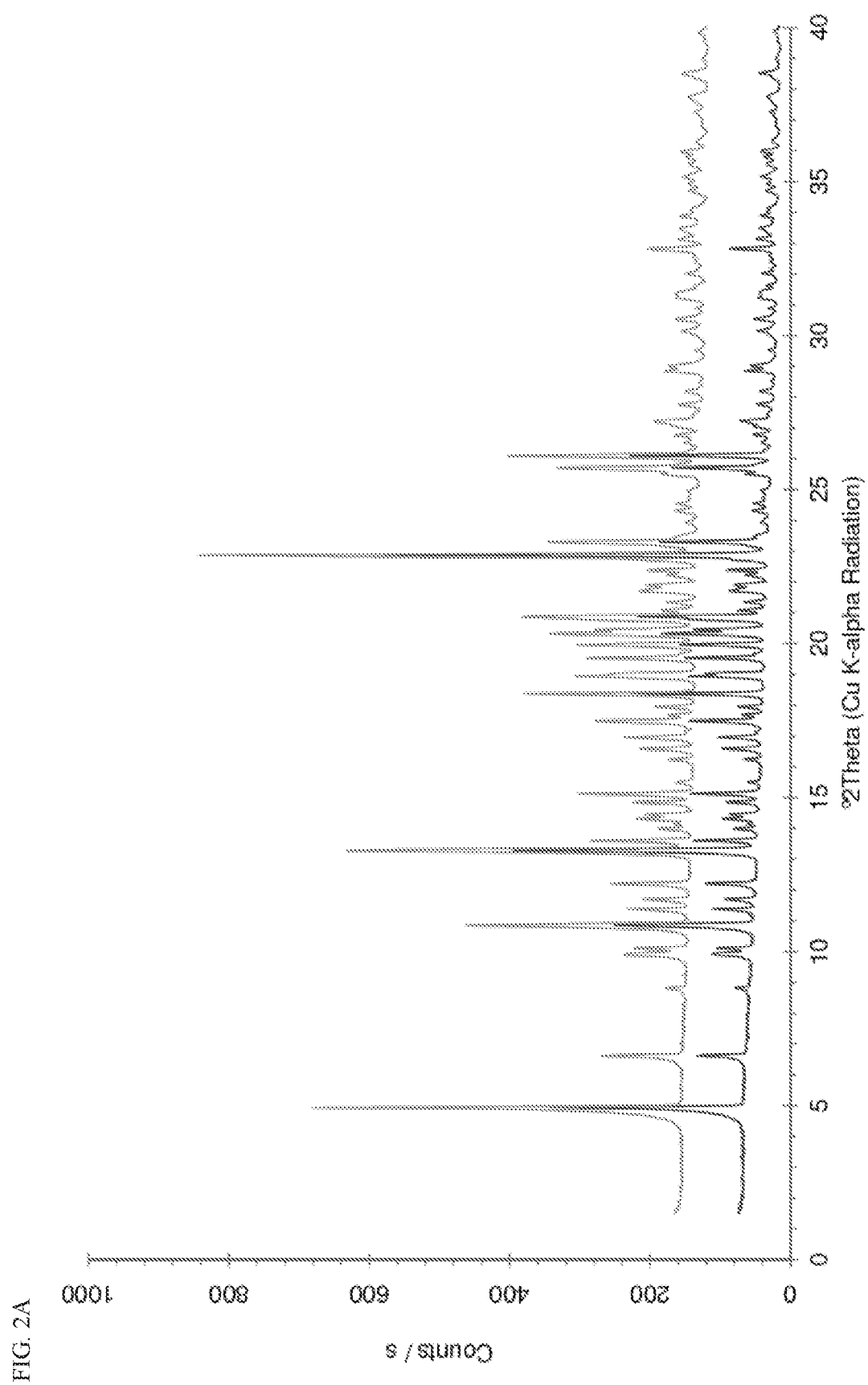
FIG. 2A is a PXRD pattern of two samples of Compound 1, Form B taken in transmission geometry.
Figure 2B:
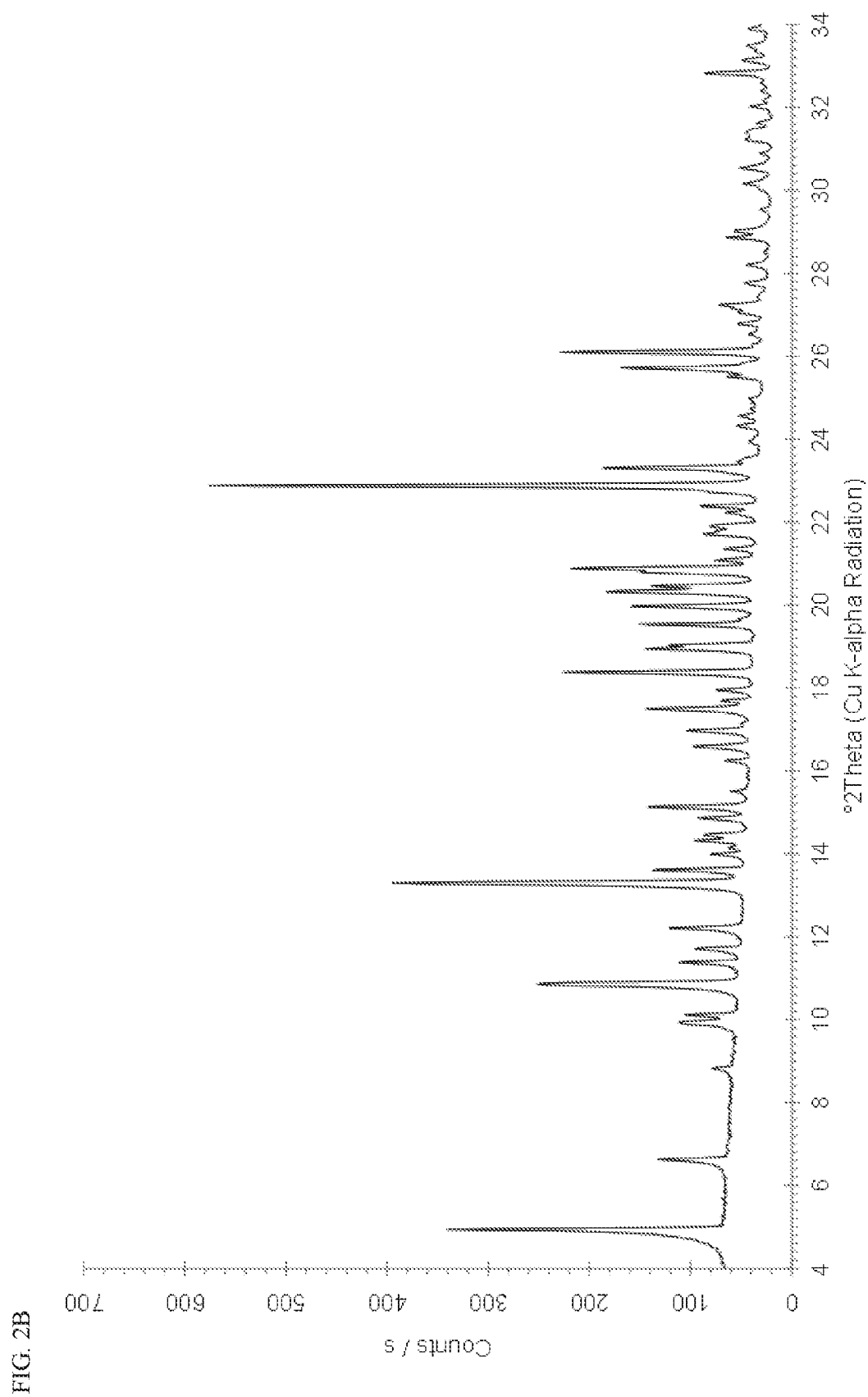
FIG. 2B is a PXRD pattern of a sample of Compound 1, Form B, taken in transmission geometry.

FIG. 2A is a PXRD pattern of two samples of Compound 1, Form B taken in transmission mode. Both of the PXRD patterns in FIG. 2A were obtained using a Stoe Stadi P powder X-ray diffractometer using Cu Kα1 radiation and transmission geometry. FIG. 2B is a PXRD pattern of Form B measured from 4 to 34 °2θ.

In some embodiments, morphic Form B can be characterized by the PXRD peaks set forth below in Table 3. For example, morphic Form B can be characterized by a PXRD peak at about 22.9 °2θ (±0.2 °2θ; ±0.1 °2θ; or ±0.0 °2θ; Cu Kα1 radiation). Form B can further be characterized by PXRD peaks at about 4.9 °2θ, 10.9 °2θ, 13.3 °2θ, 18.4 °2θ, 20.9 °2θ, and/or 26.1 °2θ (±0.2 °2θ; ±0.1 °2θ; or ±0.0 °2θ; Cu Kα1 radiation). Form B can further be characterized by PXRD peaks at about 13.6 °2θ, 15.1 °2θ, 17.5 °2θ, 19.0 °2θ, 19.5 °2θ, 20.0 °2θ, 20.3 °2θ, 20.4 °2θ, 23.3 °2θ, and/or 25.7 °2θ (±0.2 °2θ; ±0.1 °2θ; or ±0.0 °2θ; Cu Kα1 radiation).

In some embodiments, Form B can be characterized by PXRD peaks at about 4.9 °2θ, about 10.9 °2θ, and about 13.3 °2θ (±0.2 °2θ; ±0.1 °2θ; or ±0.0 °2θ; Cu Kα1 radiation). In some embodiments, Form B can be characterized by PXRD peaks at about 10.9 °2θ, about 13.3 °2θ, and about 18.4 °2θ, (±0.2 °2θ; ±0.1 °2θ; or ±0.0 °2θ; Cu Kα1 radiation). In some embodiments, Form B can be characterized by PXRD peaks at about 13.3 °2θ, about 18.4 °2θ, and about 20.9 °2θ, (±0.2 °2θ; ±0.1 °2θ; or ±0.0 °2θ; Cu Kα1 radiation). In some embodiments, Form B can be characterized by PXRD peaks at about 18.4 °2θ, about 20.9 °2θ, and about 22.9 °2θ (±0.2 °2θ; ±0.1 °2θ; or ±0.0 °2θ; Cu Kα1 radiation). In some embodiments, Form B can be characterized by PXRD peaks at about 20.9 °2θ, about 22.9 °2θ, and about 26.1 °2θ, (±0.2 °2θ; ±0.1 °2θ; or ±0.0 °2θ; Cu Kα1 radiation).

In some embodiments, Form B can be characterized by PXRD peaks at about 22.9 °2θ and about 4.9 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, and about 10.9 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, and about 13.3 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, and about 18.4 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 18.4 °2θ, and about 20.9 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 18.4 °2θ, about 20.9 °2θ, and about 26.1 °2θ (±0.2 °2θ; ±0.1 °2θ; or ±0.0 °2θ; Cu Kα1 radiation). In some embodiments, morphic Form B can further be characterized by PXRD peaks at about 23.3 and/or 25.7 °2θ (±0.2 °2θ; ±0.1 °2θ; or ±0.0 °2θ; Cu Kα1 radiation).

In some embodiments, Form B can be characterized by PXRD peaks at about 22.9 °2θ, about 4.9 °2θ, about 10.9 °2θ, about 13.3 °2θ, about 13.6 °2θ, about 18.4 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 18.4 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.0 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.0 °2θ, about 20.3 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.0 °2θ, about 20.3 °2θ, about 20.4 °2θ, about 20.9 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.0 °2θ, about 20.3 °2θ, about 20.4 °2θ, about 20.9 °2θ, about 23.3 °2θ, and about 26.1 °2θ (±0.2 °2θ; ±0.1 °2θ; or ±0.0 °2θ; Cu Kα1 radiation). In some embodiments, Form B can be characterized by PXRD peaks at about 22.9 °2θ, about 4.9 °2θ, about 10.9 °2θ, about 13.3 °2θ, about 13.6 °2θ, about 15.1 °2θ, about 17.5 °2θ, about 18.4 °2θ, about 19.0 °2θ, about 19.5 °2θ, about 20.0 °2θ, about 20.3 °2θ, about 20.4 °2θ, about 20.9 °2θ, about 23.3 °2θ, about 25.7 °2θ, and about 26.1 °2θ (±0.2 °2θ; ±0.1 °2θ; or ±0.0 °2θ; Cu Kα1 radiation).

In some embodiments, morphic Form B is characterized by one peak selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by two peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by three peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by four peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by five peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by six peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by seven peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by eight peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by nine peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by ten peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by eleven peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by twelve peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by thirteen peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by fourteen peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by fifteen peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by sixteen peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation). In some embodiments, morphic Form B is characterized by seventeen peaks selected from about 4.9 °2θ, 10.9 °2θ, 13.3 °2θ, 13.6 °2θ, 15.1 °2θ, 17.5 °2θ, 18.4 °2θ, 19.0 °2θ, 19.5 °2θ, 20.0 °2θ, 20.3 °2θ, 20.4 °2θ, 20.9 °2θ, 22.9 °2θ, 23.3 °2θ, 25.7 °2θ, and 26.1 °2θ (±0.2 °2θ; ±0.1 °2θ; or ±0.0 °2θ; Cu Kα1 radiation).

Accordingly, in some embodiments, morphic Form B is characterized by one, two, three, four, five, six, seven, eight, nine, ten, eleven, twelve, thirteen, fourteen, fifteen, sixteen or seventeen peaks selected from about 4.9, 10.9, 13.3, 13.6, 15.1, 17.5, 18.4, 19.0, 19.5, 20.0, 20.3, 20.4, 20.9, 22.9, 23.3, 25.7, and 26.1 °2θ (Cu Kα1 radiation).

TABLE 3

Representative PXRD Peaks of Morphic Form B (Cu Kα1 radiation)

| Angle (°2θ) | d value (Å) | Intensity |
| --- | --- | --- |
| 4.9 | 17.89 | s |
| 6.6 | 13.38 | w |
| 8.8 | 10.02 | vw |
| 9.9 | 8.91 | w |
| 10.1 | 8.74 | w |
| 10.9 | 8.15 | s |
| 11.4 | 7.78 | w |
| 11.7 | 7.56 | w |
| 12.2 | 7.25 | w |
| 13.3 | 6.66 | s |
| 13.6 | 6.50 | m |
| 14.0 | 6.32 | w |
| 14.3 | 6.19 | w |
| 14.4 | 6.13 | w |
| 14.8 | 5.96 | w |
| 15.1 | 5.85 | m |
| 15.5 | 5.72 | vw |
| 16.2 | 5.46 | vw |
| 16.6 | 5.34 | w |
| 17.0 | 5.22 | w |
| 17.5 | 5.07 | m |
| 17.7 | 5.01 | w |
| 18.0 | 4.94 | w |
| 18.4 | 4.83 | s |
| 19.0 | 4.68 | m |
| 19.5 | 4.54 | m |
| 20.0 | 4.44 | m |
| 20.3 | 4.37 | m |
| 20.4 | 4.34 | m |
| 20.9 | 4.25 | s |
| 21.1 | 4.21 | w |
| 21.4 | 4.16 | w |
| 21.7 | 4.09 | w |
| 21.9 | 4.06 | w |
| 22.2 | 4.00 | w |
| 22.4 | 3.97 | w |
| 22.9 | 3.89 | vs |
| 23.3 | 3.81 | m |
| 23.9 | 3.71 | vw |
| 24.3 | 3.66 | vw |
| 24.6 | 3.62 | vw |
| 25.5 | 3.49 | w |
| 25.7 | 3.46 | m |
| 26.1 | 3.41 | s |
| 26.8 | 3.33 | vw |
| 27.2 | 3.27 | w |
| 27.8 | 3.21 | vw |
| 28.2 | 3.16 | vw |
| 28.9 | 3.09 | w |
| 29.0 | 3.07 | w |
| 29.5 | 3.02 | vw |
| 30.2 | 2.96 | w |
| 30.5 | 2.92 | w |
| 30.9 | 2.89 | vw |
| 31.2 | 2.86 | vw |
| 31.6 | 2.83 | vw |
| 32.0 | 2.79 | vw |
| 32.8 | 2.73 | w |
| 33.1 | 2.70 | w |
| 33.5 | 2.67 | vw |
| 33.9 | 2.64 | vw |
| 34.7 | 2.58 | vw |
| 35.2 | 2.55 | vw |
| 35.6 | 2.52 | vw |
| 35.8 | 2.51 | vw |
| 36.0 | 2.49 | vw |
| 36.3 | 2.47 | vw |
| 37.3 | 2.41 | vw |
| 37.8 | 2.38 | vw |
| 38.5 | 2.33 | w |
| 39.9 | 2.26 | vw |

Figure 9A:
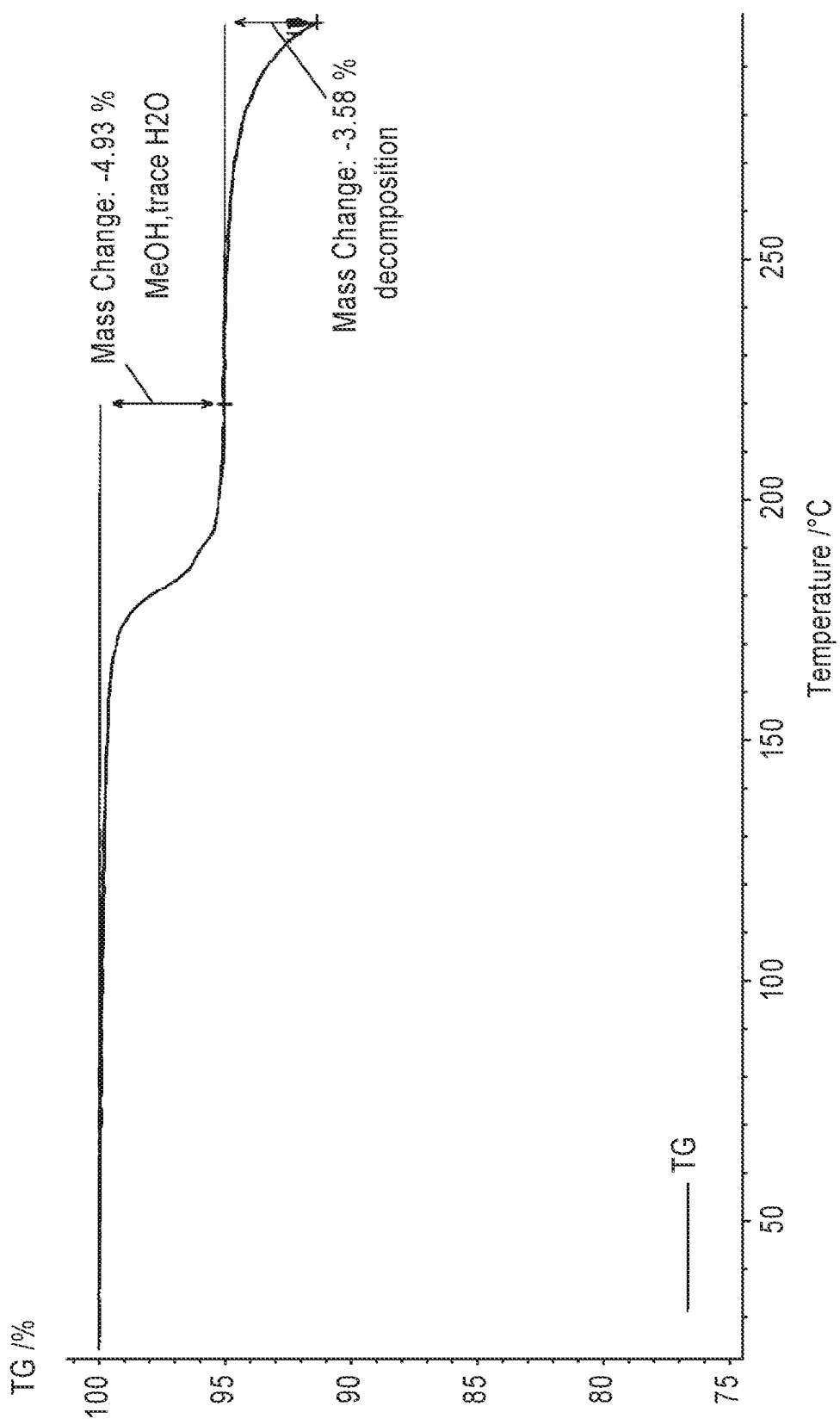
FIG. 9A is a TG-FTIR diagram of a first sample of Compound 1, Form B.
Figure 9B:
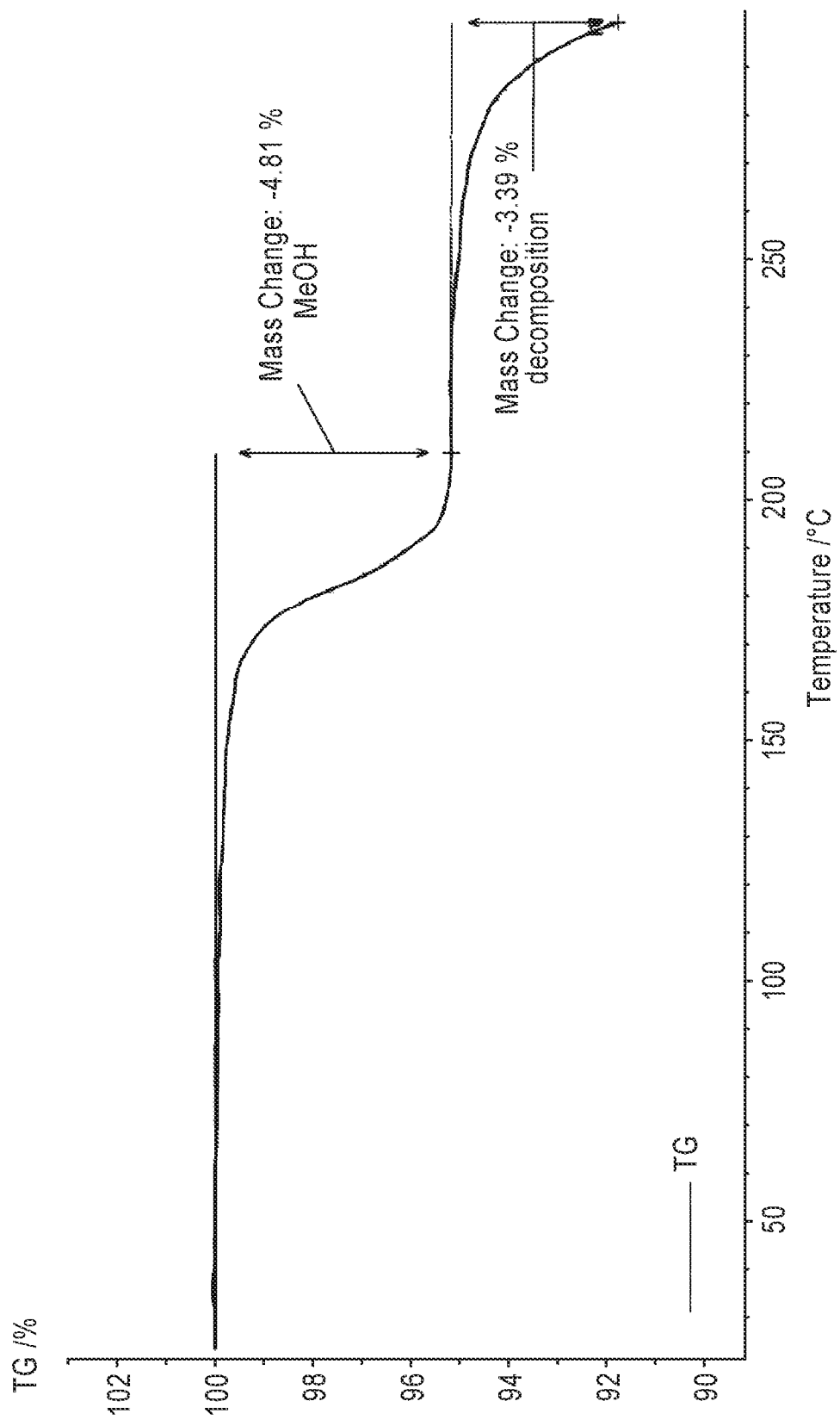
FIG. 9B is a TG-FTIR diagram of a second sample of Compound 1, Form B.

FIG. 9A is a TG-FTIR diagram of a first sample of Compound 1, Form B prepared as set forth in Example 1, Experiment 9. FIG. 9B is a TG-FTIR diagram of a second sample of Compound 1, Form B prepared as set forth in Example 1, Experiment 10. FIG. 9A and FIG. 9B was obtained using a Netzsch TG 209, over the range of 25° C. to 300° C. The scanning speed was 10° C. per minute.

As shown in FIG. 9A and FIG. 9B, morphic Form B shows a mass change between of about 4.9% (e.g., about 4.81%; about 4.93%) about 100° C. and about 215° C. Without wishing to be bound by theory, this mass change is attributed to loss of methanol and trace water. Accordingly, in some embodiments, morphic Form B contains about 4.9% methanol (w/w). In some embodiments, morphic Form B is characterized by a mass loss of about 4.9% between about 100° C. and about 215° C. (e.g., as measured by TG-FTIR).

Figure 16:
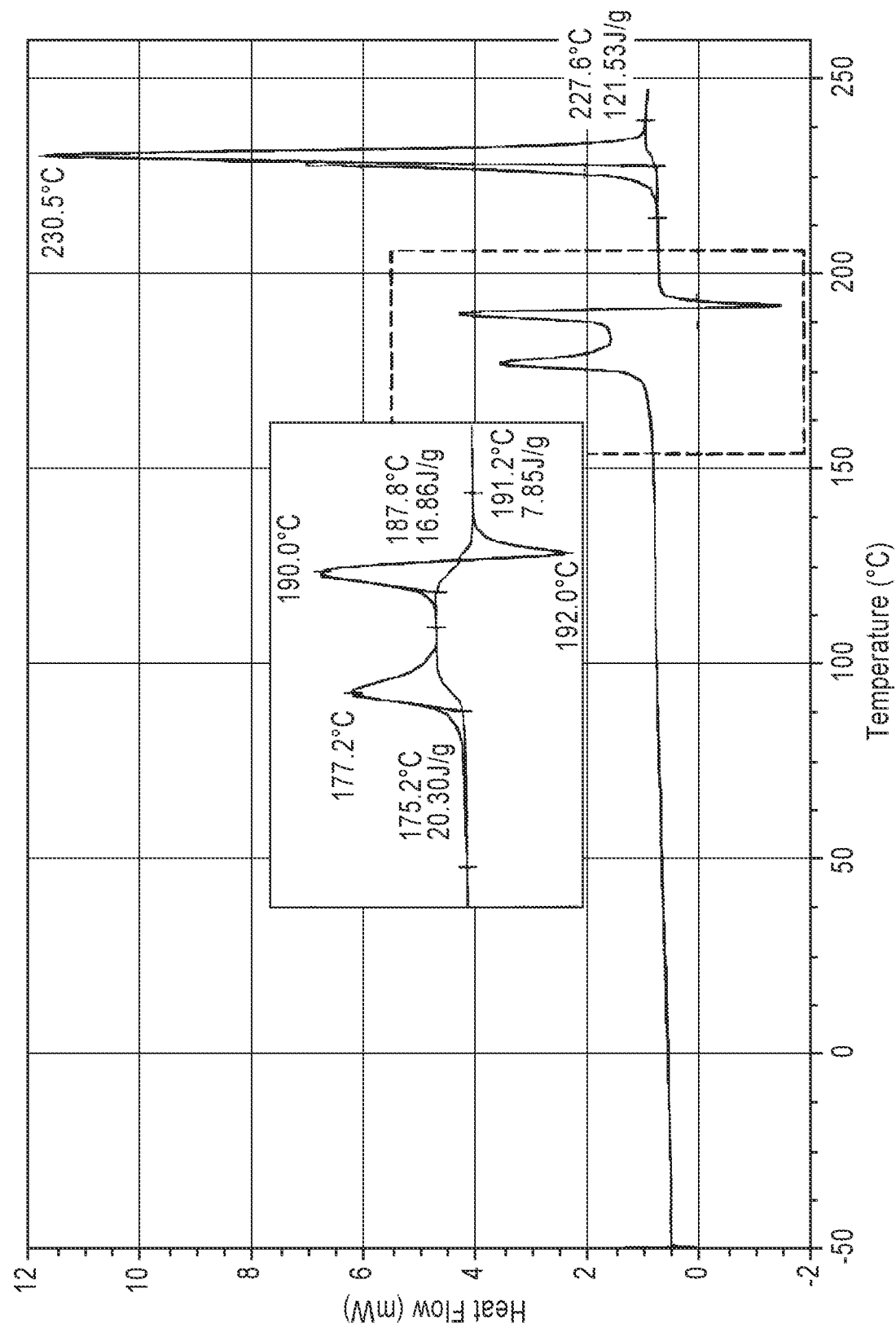
FIG. 16 is a DSC diagram of a sample of Compound 1, Form B.

FIG. 16 is a DSC diagram of a sample of Compound 1, Form B. FIG. 16 was obtained using a DSC Q2000 V24.3 with a hermetically closed gold sample pan. The heating rate was 10° C. per minute. The DSC diagram shows an insert between about 155° C. and 205° C.

As shown in FIG. 16, morphic Form B exhibited endothermic peaks at about 177° C. (20 J/g) (e.g., about 177.2° C. (20.30 J/g)); about 190° C. (17 J/g) (e.g., about 190.0° C. (16.86 J/g)); and about 231° C. (122 J/g) (e.g., about 230.5° C. (121.53 J/g)). Morphic Form B also exhibited an exothermic peak at about 191° C. (8 J/g) (e.g., about 191.2° C. (7.85 J/g)). Accordingly, in some embodiments, morphic Form B shows peaks above about 170° C. In some embodiments, morphic Form B is characterized by a DSC diagram exhibiting an endothermic peak at about 177° C. (20 J/g) (e.g., about 177.2° C. (20.30 J/g)). In some embodiments, morphic Form B is characterized by a DSC diagram exhibiting an endothermic peak at about 190° C. (17 J/g) (e.g., about 190.0° C. (16.86 J/g)). In some embodiments, morphic Form B is characterized by a DSC diagram exhibiting an endothermic peak at about 231° C. (122 J/g) (e.g., about 230.5° C. (121.53 J/g)). In some embodiments, morphic Form B is characterized by a DSC diagram exhibiting endothermic peaks at about 177° C. (20 J/g) (e.g., about 177.2° C. (20.30 J/g)); about 190° C. (17 J/g) (e.g., about 190.0° C. (16.86 J/g)); and about 231° C. (122 J/g) (e.g., about 230.5° C. (121.53 J/g)). In some embodiments, morphic Form B is characterized by a DSC diagram exhibiting an exothermic peak at about 191° C. (8 J/g) (e.g., about 191.2° C. (7.85 J/g)).

Figure 21A:
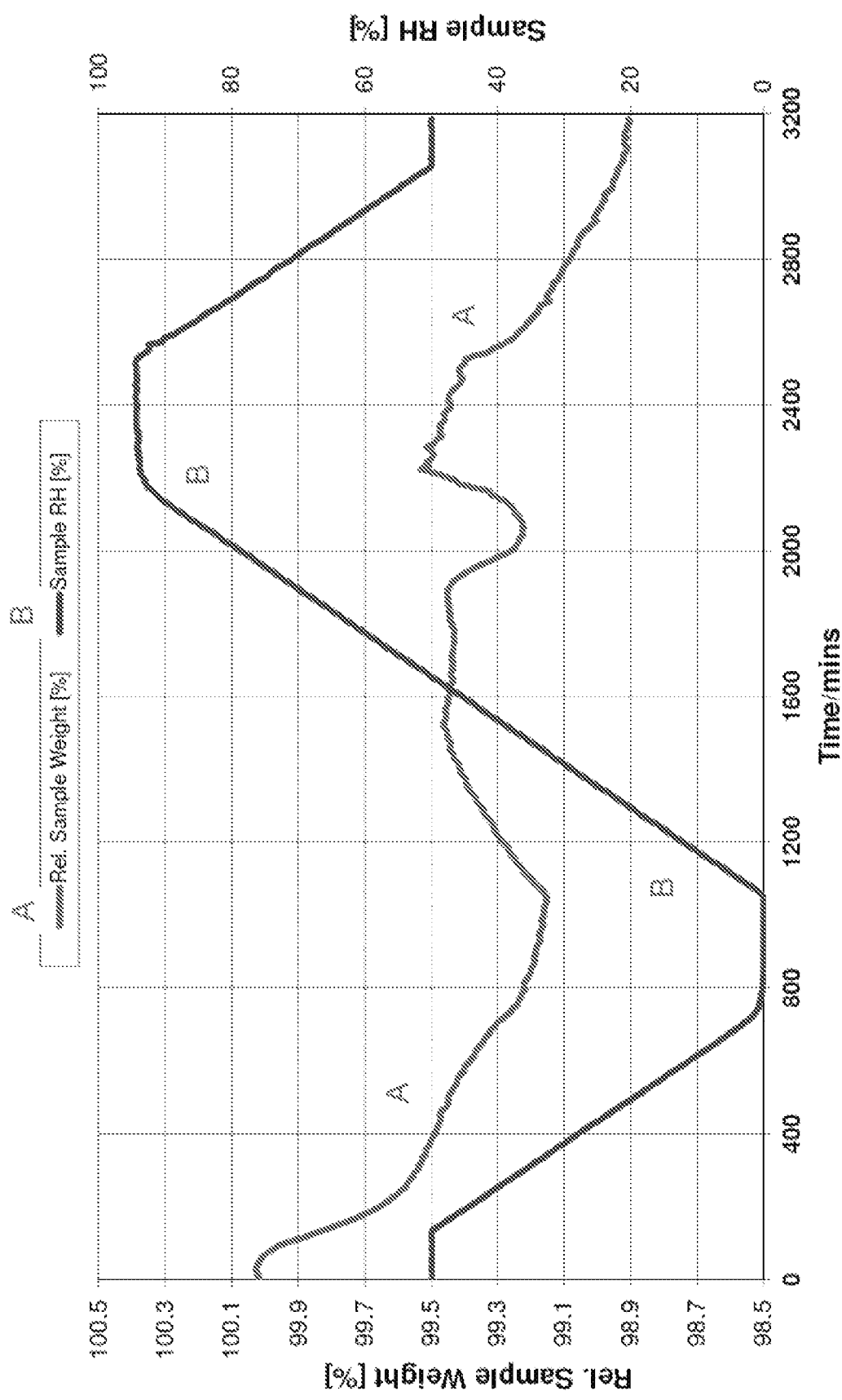
FIG. 21A is a DVS diagram of a sample of Compound 1, Form B as a function of time and the applied change in relative humidity.
Figure 21B:
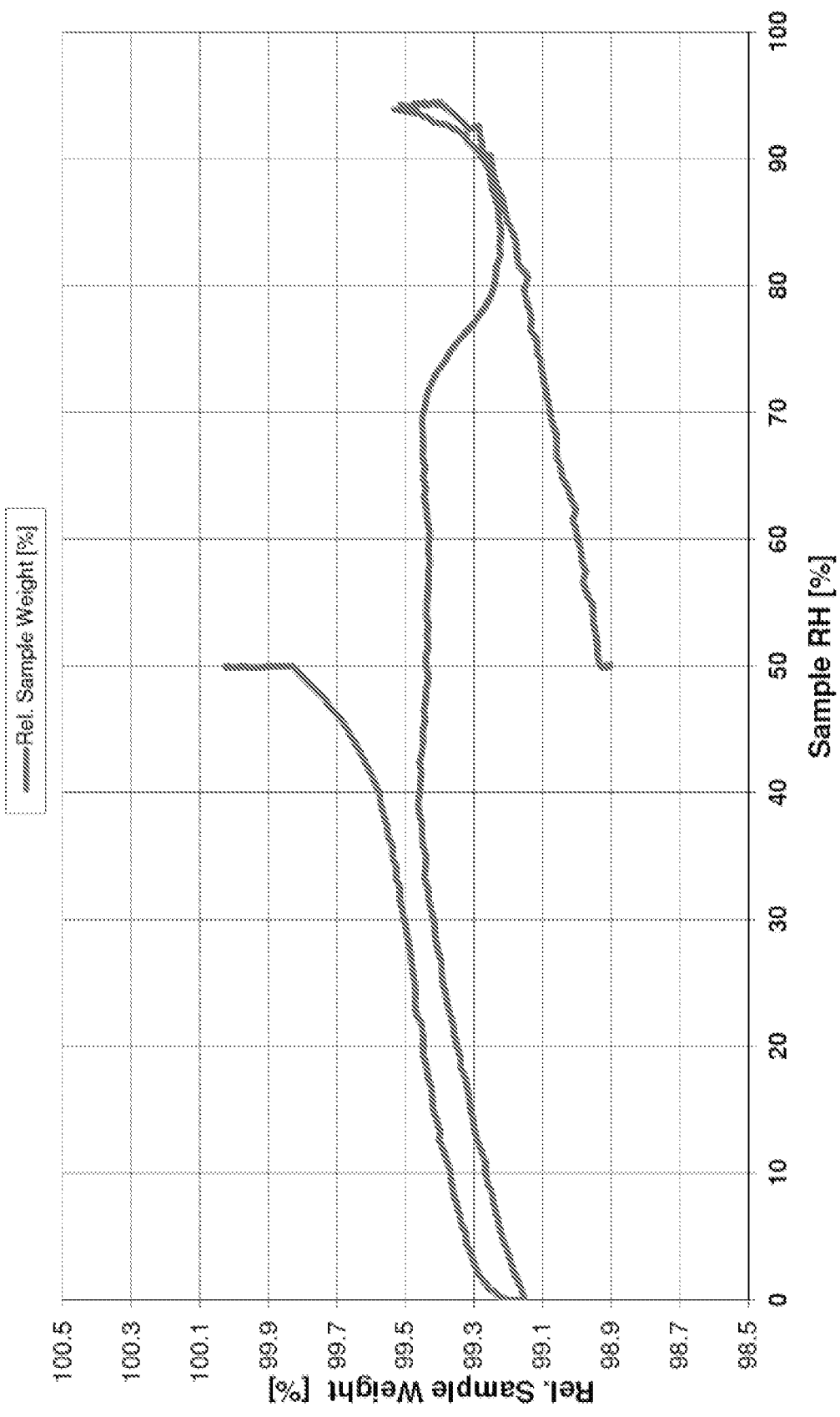
FIG. 21B is a DVS diagram of a sample of Compound 1, Form B as a function of the applied relative humidity.

FIG. 21A is a DVS diagram of a sample of Compound 1, Form B as a function of time and the applied change in relative humidity. Line A represents the relative weight of the sample at each relative humidity. Line B represents the applied relative humidity (i.e., the applied measurement program). FIG. 21B is a DVS diagram of a sample of Compound 1, Form B as a function of the applied relative humidity. FIG. 21A and FIG. 21B were obtained using a Sorptions Prufsystem ProUmid system using a scan rate of 5% relative humidity per hour at a temperature of 25° C. As shown in FIGS. 21A and 21B, the mass of the sample of morphic Form B was found to fluctuate as a function of relative humidity. Without wishing to be bound by theory, this suggests that morphic Form B is hygroscopic. Additionally, Form B was found to transform in to Form A under the conditions of the DVS. Accordingly, in some embodiments, Form B can be converted to Form A under conditions of high relative humidity (e.g., at about 25° C. and about 50% relative humidity or above, for instance under conditions of dynamic water vapor sorption experiments).

Form C

Morphic Form C of Compound 1 was characterized as an ethanol hemisolvate of Compound 1. In some embodiments, morphic Form C can be prepared by crystallization of Compound 1 from ethanol (e.g., substantially pure ethanol) by cooling a solution of Compound 1 in ethanol.

Figure 3:
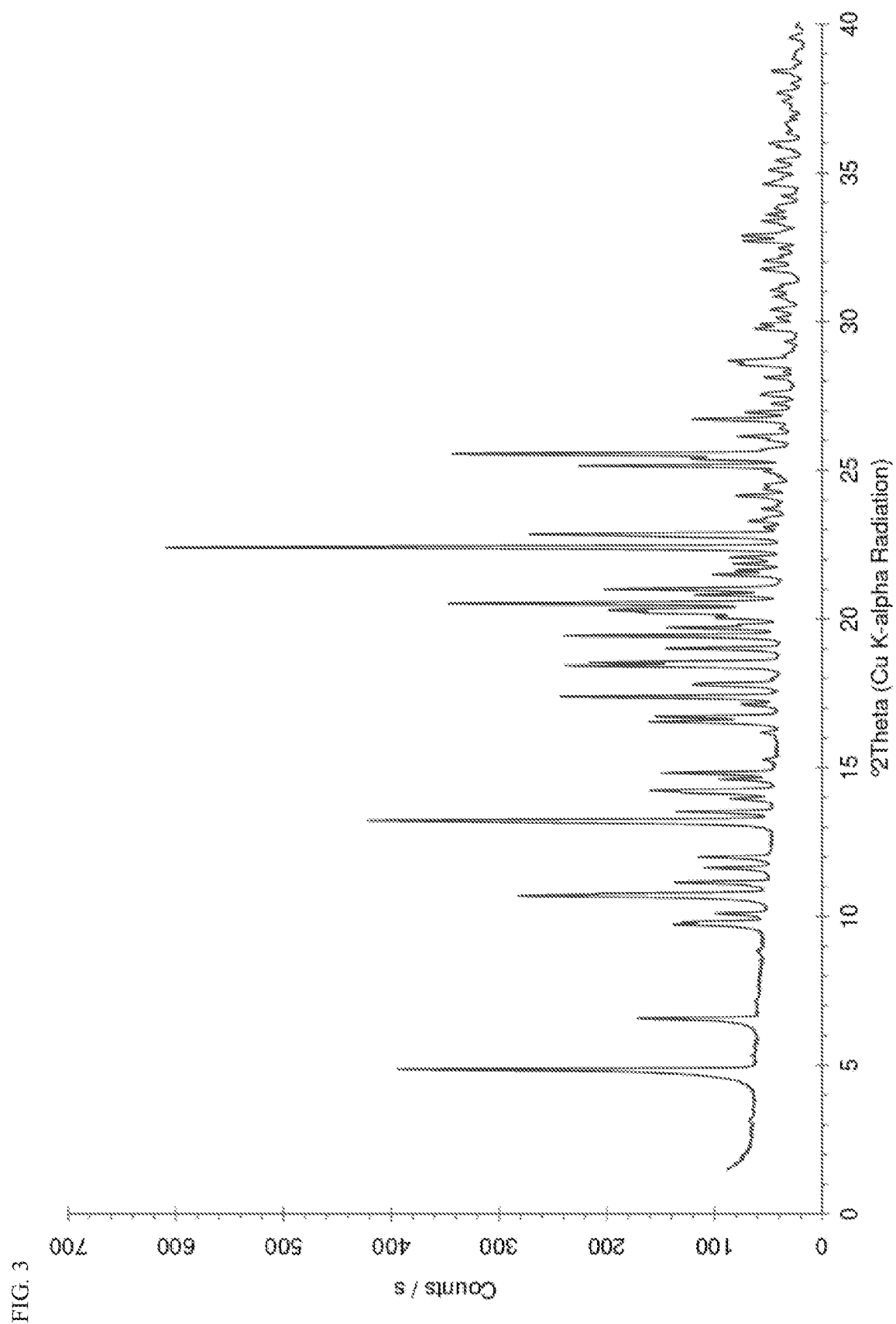
FIG. 3 is a PXRD pattern of a sample of Compound 1, Form C taken in transmission geometry.

FIG. 3 is a PXRD pattern of a sample of Compound 1, Form C taken in transmission mode. FIG. 3 was obtained using a Stoe Stadi P powder X-ray diffractometer using Cu Kα1 radiation and transmission geometry.

In some embodiments, morphic Form C can be characterized by the PXRD peaks set forth below in Table 4. For example, morphic Form C can be characterized by a PXRD peak at about 22.4 °2θ (±0.2 °2θ; ±0.1 °2θ; or ±0.0 °2θ; Cu Kα1 radiation). Morphic Form C can further be characterized by a PXRD peak at about 4.9 °2θ, 10.7 °2θ, 13.2 °2θ, 17.4 °2θ, 19.4 °2θ, 20.5 °2θ, 22.8 °2θ, 25.2 °2θ, and/or 25.6, °2θ (±0.2 °2θ; ±0.1 °2θ; or ±0.0 °2θ; Cu Kα1 radiation). Morphic Form C can further be characterized by a PXRD peak at about 6.6 °2θ, 11.2 °2θ, 13.5 °2θ, 14.2 °2θ, 14.8 °2θ, 16.5 °2θ, 16.7 °2θ, 18.5 °2θ, 19.0 °2θ, 19.7 °2θ, 20.3 °2θ, 21.0 °2θ, 25.4 °2θ, and/or 26.7 °2θ (±0.2 °2θ; ±0.1 °2θ; or ±0.0 °2θ; Cu Kα1 radiation).

In some embodiments, morphic Form C can be characterized by PXRD peaks at about 4.9 °2θ, about 10.7 °2θ, and about 13.2 °2θ (±0.2 °2θ; ±0.1 °2θ; or ±0.0 °2θ; Cu Kα1 radiation). In some embodiments, morphic Form C can be characterized by PXRD peaks at about 10.7 °2θ, about 13.2 °2θ, and about 17.4 °2θ (±0.2 °2θ; ±0.1 °2θ; or ±0.0 °2θ; Cu Kα1 radiation). In some embodiments, morphic Form C can be characterized by PXRD peaks at about 13.2 °2θ, about 17.4 °2θ, and about 19.4 °2θ (±0.2 °2θ; ±0.1 °2θ; or ±0.0 °2θ; Cu Kα1 radiation). In some embodiments, morphic Form C can be characterized by PXRD peaks at about 17.4 °2θ, about 19.4 °2θ, and about 20.5 °2θ (±0.2 °2θ; ±0.1 °2θ; or ±0.0 °2θ; Cu Kα1 radiation). In some embodiments, morphic Form C can be characterized by PXRD peaks at about 19.4 °2θ, about 20.5 °2θ, and about 22.4 °2θ (±0.2 °2θ; ±0.1 °2θ; or ±0.0 °2θ; Cu Kα1 radiation). In some embodiments, morphic Form C can be characterized by PXRD peaks at about 20.5 °2θ, about 22.4 °2θ, and about 22.8 °2θ (±0.2 °2θ; ±0.1 °2θ; or ±0.0 °2θ; Cu Kα1 radiation). In some embodiments, morphic Form C can be characterized by PXRD peaks at about 22.4 °2θ, about 22.8 °2θ, and about 25.2 °2θ (±0.2 °2θ; ±0.1 °2θ; or ±0.0 °2θ; Cu Kα1 radiation). In some embodiments, morphic Form C can be characterized by PXRD peaks at about 22.8 °2θ, about 25.2 °2θ, and about 25.6 °2θ (±0.2 °2θ; ±0.1 °2θ; or ±0.0 °2θ; Cu Kα1 radiation).

In some embodiments, morphic Form C can be characterized by a PXRD peak at about 22.4 °2θ and about 4.9 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, and about 10.7 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, and about 13.2 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, and about 17.4 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, about 17.4 °2θ, and about 19.4 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, about 17.4 °2θ, about 19.4 °2θ, and about 20.5 °2θ

(±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, about 17.4 °2θ, about 19.4 °2θ, about 20.5 °2θ, and about 22.8 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, about 17.4 °2θ, about 19.4 °2θ, about 20.5 °2θ, about 22.8 °2θ, and about 25.2 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 10.7 °2θ, about 13.2 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation).

In some embodiments, morphic Form C can be characterized by a PXRD peak at about 22.4 °2θ about 4.9 °2θ, about 6.6 °2θ, about 10.7 °2θ, about 13.2 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 19.7 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 19.7 °2θ, about 20.3 °2θ, about 20.5 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 19.7 °2θ, about 20.3 °2θ, about 20.5 °2θ, about 21.0 °2θ, about 22.8 °2θ, about 25.2 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 19.7 °2θ, about 20.3 °2θ, about 20.5 °2θ, about 21.0 °2θ, about 22.8 °2θ, about 25.2 °2θ, about 25.4 °2θ, and about 25.6 °2θ (±0.2 °2θ; ±0.1 °2θ; or ±0.0 °2θ; Cu Kα1 radiation). In some embodiments, morphic Form C can be characterized by a PXRD peak at about 22.4 °2θ about 4.9 °2θ, about 6.6 °2θ, about 10.7 °2θ, about 11.2 °2θ, about 13.2 °2θ, about 13.5 °2θ, about 14.2 °2θ, about 14.8 °2θ, about 16.5 °2θ, about 16.7 °2θ, about 17.4 °2θ, about 18.5 °2θ, about 19.0 °2θ, about 19.4 °2θ, about 19.7 °2θ, about 20.3 °2θ, about 20.5 °2θ, about 21.0 °2θ, about 22.8 °2θ, about 25.2 °2θ, about 25.4 °2θ, about 25.6 °2θ, and about 26.7 °2θ (±0.2 °2θ; ±0.1 °2θ; or ±0.0 °2θ; Cu Kα1 radiation).

Accordingly, in some embodiments, Form C can be characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three or twenty-four PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (Cu Kα1 radiation). In some embodiments, Form C can be characterized by one PXRD peak selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by two PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by three PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by four PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by five PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by six PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by seven PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by eight PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by nine PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by ten PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by eleven PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twelve PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by thirteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by fourteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by fifteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by sixteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by seventeen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by eighteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by nineteen PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twenty PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twenty-one PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twenty-two PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twenty-three PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation). In some embodiments, Form C can be characterized by twenty-four PXRD peaks selected from about 4.9, 6.6, 10.7, 11.2, 13.2, 13.5, 14.2, 14.8, 16.5, 16.7, 17.4, 18.5, 19.0, 19.4, 19.7, 20.3, 20.5, 21.0, 22.8, 22.4, 25.2, 25.4, 25.6, and 26.7 °2θ (±0.2 °2θ; ±0.1 °2θ; or ±0.0 °2θ; Cu Kα1 radiation).

TABLE 4

Representative PXRD Peaks for Morphic Form C (Cu Kα1 radiation)

| Angle (°2θ) | d value (Å) | Intensity |
| --- | --- | --- |
| 4.9 | 18.17 | s |
| 6.6 | 13.44 | m |
| 9.8 | 9.06 | w |
| 10.1 | 8.75 | w |
| 10.7 | 8.25 | s |
| 11.2 | 7.93 | m |
| 11.6 | 7.61 | w |
| 12.0 | 7.37 | w |
| 13.2 | 6.70 | s |
| 13.5 | 6.55 | m |
| 14.0 | 6.34 | w |
| 14.2 | 6.22 | m |
| 14.6 | 6.06 | w |
| 14.8 | 5.97 | m |
| 15.3 | 5.80 | vw |
| 16.2 | 5.47 | vw |
| 16.5 | 5.36 | m |
| 16.7 | 5.30 | m |
| 17.1 | 5.17 | w |

TABLE 4-continued

Representative PXRD Peaks for Morphic Form C (Cu Kα1 radiation)

| Angle (°2θ) | d value (Å) | Intensity |
|---|---|---|
| 17.4 | 5.10 | s |
| 17.8 | 4.98 | w |
| 18.5 | 4.79 | m |
| 19.0 | 4.66 | m |
| 19.4 | 4.57 | s |
| 19.7 | 4.50 | m |
| 20.0 | 4.43 | w |
| 20.3 | 4.37 | m |
| 20.5 | 4.32 | s |
| 20.8 | 4.27 | w |
| 21.0 | 4.22 | m |
| 21.5 | 4.13 | w |
| 21.6 | 4.10 | w |
| 21.8 | 4.07 | w |
| 22.1 | 4.03 | w |
| 22.4 | 3.96 | vs |
| 22.8 | 3.89 | s |
| 23.1 | 3.85 | vw |
| 23.3 | 3.82 | w |
| 23.7 | 3.75 | vw |
| 24.1 | 3.68 | w |
| 24.4 | 3.65 | vw |
| 24.5 | 3.63 | vw |
| 25.2 | 3.54 | s |
| 25.4 | 3.51 | m |
| 25.6 | 3.48 | s |
| 26.1 | 3.41 | w |
| 26.7 | 3.34 | m |
| 26.9 | 3.31 | w |
| 27.2 | 3.27 | vw |
| 27.6 | 3.23 | w |
| 28.1 | 3.17 | vw |
| 28.6 | 3.12 | w |
| 29.3 | 3.04 | vw |
| 29.7 | 3.00 | w |
| 30.1 | 2.97 | vw |
| 30.4 | 2.94 | vw |
| 31.1 | 2.88 | vw |
| 31.2 | 2.86 | vw |
| 31.8 | 2.81 | w |
| 32.0 | 2.79 | w |
| 32.5 | 2.76 | vw |
| 32.7 | 2.74 | w |
| 32.9 | 2.72 | w |
| 33.4 | 2.68 | w |
| 33.6 | 2.67 | w |
| 33.8 | 2.65 | vw |
| 34.2 | 2.62 | vw |
| 34.6 | 2.59 | w |
| 35.1 | 2.55 | vw |
| 35.4 | 2.53 | vw |
| 36.0 | 2.49 | vw |
| 37.1 | 2.42 | vw |
| 37.4 | 2.40 | vw |
| 37.7 | 2.38 | vw |
| 38.0 | 2.37 | vw |
| 38.4 | 2.34 | vw |
| 39.6 | 2.28 | vw |

Figure 10:
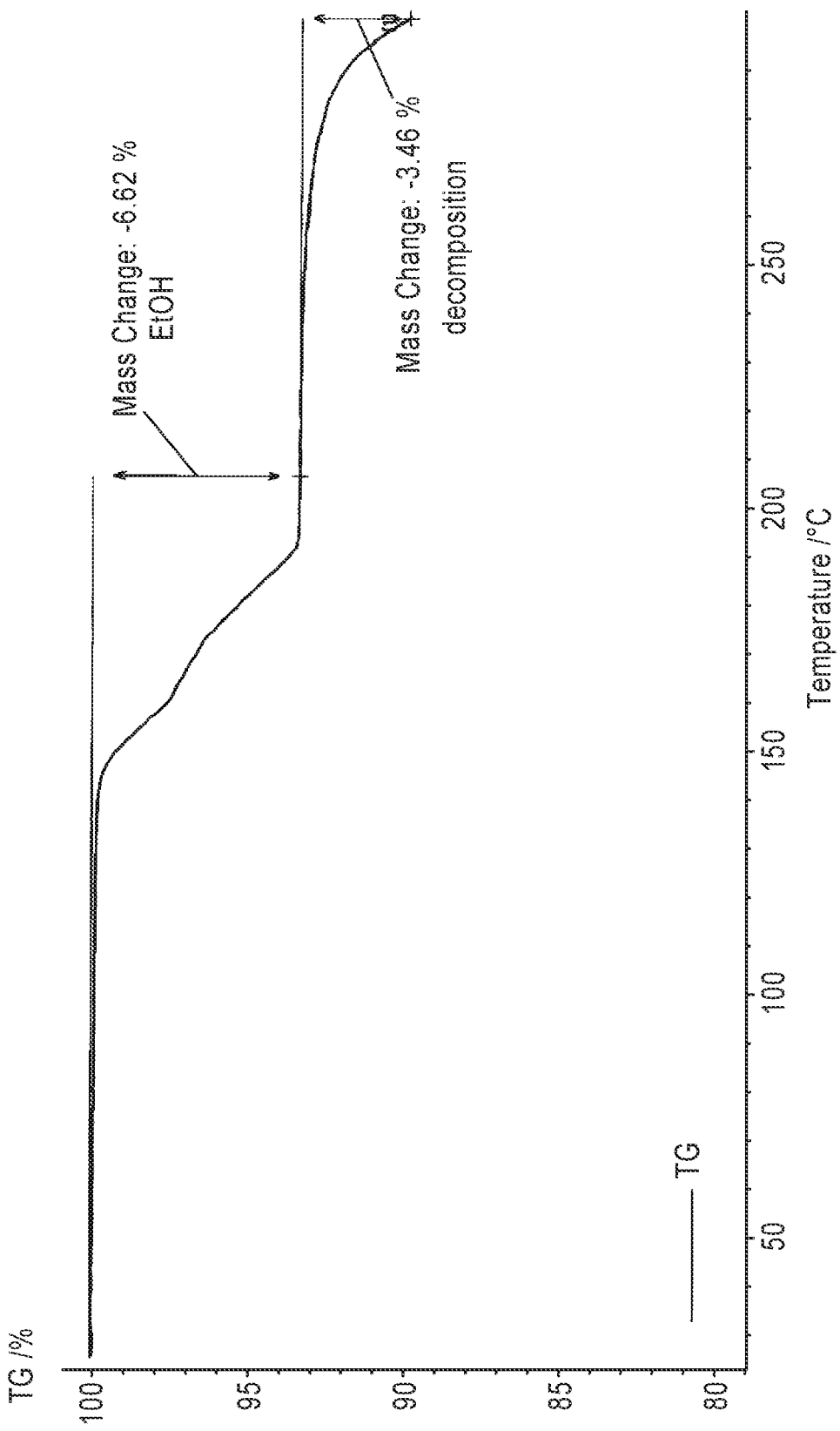
FIG. 10 is a TG-FTIR diagram of a sample of Compound 1, Form C.

FIG. 10 is a TG-FTIR diagram of a sample of Compound 1, Form C. FIG. 10 was obtained using a Netzsch TG 209, over the range of 25° C. to 300° C. The scanning speed was 10° C. per minute. As shown in FIG. 10, Form C exhibited a mass change of about 6.6% (e.g., about 6.62%) between about 100 and about 200° C. Without wishing to be bound by theory, this is proposed to be due to a loss of ethanol. Accordingly, in some embodiments, morphic Form C contains about 6.6% ethanol (w/w). Accordingly, in some embodiments, morphic Form C is characterized by a mass loss of about 6.6% between about 100 and about 200° C. (e.g., as measured by TG-FTIR).

Figure 17:
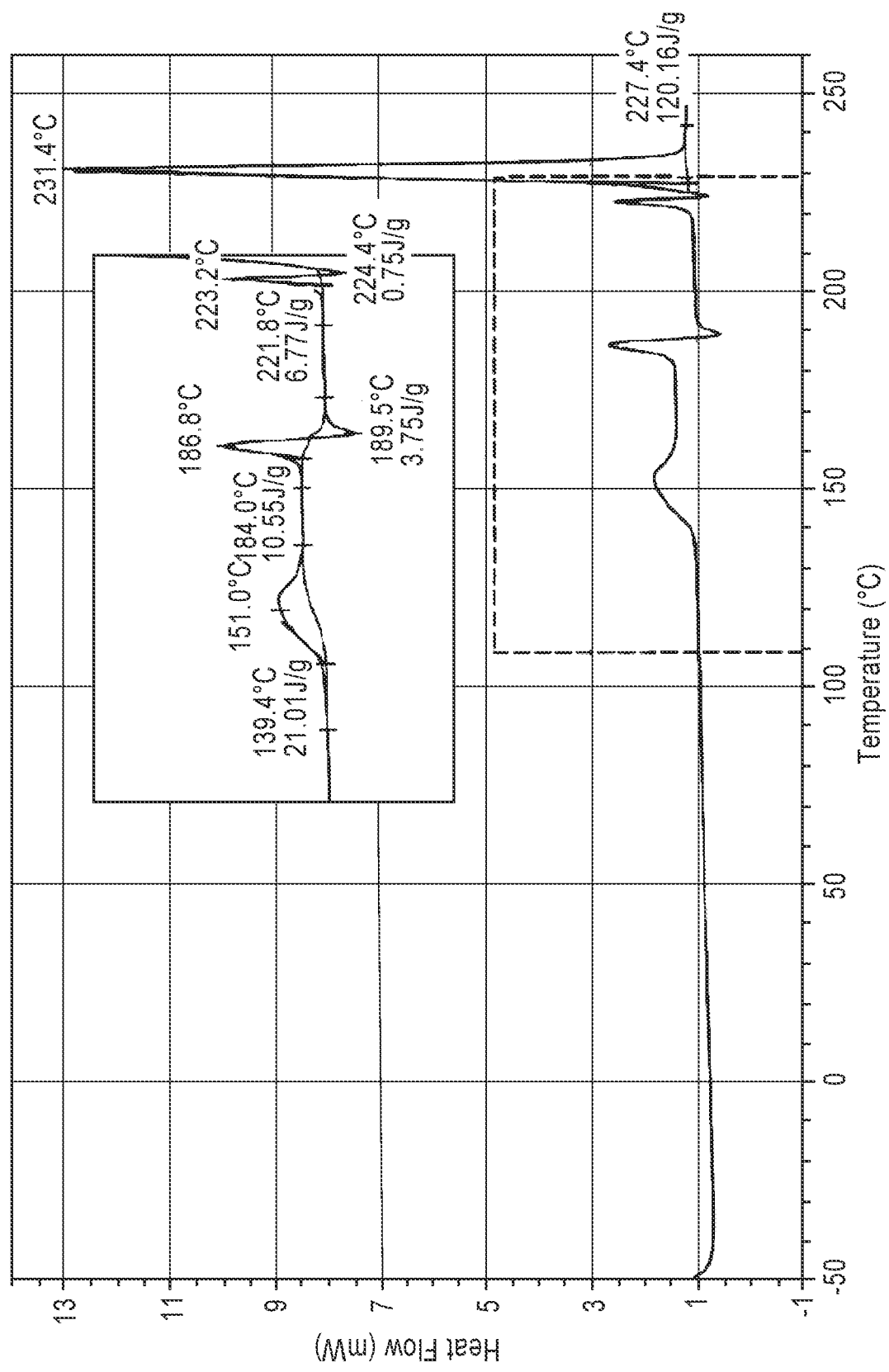
FIG. 17 is a DSC diagram of a sample of Compound 1, Form C.

FIG. 17 is a DSC diagram of a sample of Compound 1, Form C. FIG. 17 was obtained using a DSC Q2000 V24.3 with a hermetically closed gold sample pan. The heating rate was 10° C. per minute. The DSC diagram shows an insert between about 120° C. and 225° C. for greater detail. As shown in FIG. 17, Form C exhibited endotherms with peaks at about 151° C. (21 J/g) (e.g., about 151.0° C. (21.01 J/g)); about 187° C. (11 J/g) (e.g., about 186.8° C. (10.55 J/g)); about 223° C. (7 J/g) (e.g., about 223.2° C. (6.77 J/g)); and about 231° C. (120 J/g) (e.g., about 231.4° C. (120.16 J/g)). Form C also exhibited exotherms with troughs at about 190° C. (4 J/g) (e.g., about 189.5° C. (3.75 J/g)) and about 224° C. (1 J/g) (e.g., about 224.4° C. (0.75 J/g)). Accordingly, in some embodiments, morphic Form C exhibits DSC peaks above about 150° C.

In some embodiments, Form C is characterized by a DSC diagram exhibiting an endothermic peak at about 151° C. (21 J/g) (e.g., about 151.0° C. (21.01 J/g)). In some embodiments, Form C is characterized by a DSC diagram exhibiting an endothermic peak at about 187° C. (11 J/g) (e.g., about 186.8° C. (10.55 J/g)). In some embodiments, Form C is characterized by a DSC diagram exhibiting an endothermic peak at about 223° C. (7 J/g) (e.g., about 223.2° C. (6.77 J/g)). In some embodiments, Form C is characterized by a DSC diagram exhibiting an endothermic peak at about 231° C. (120 J/g) (e.g., about 231.4° C. (6.77 J/g)). In some embodiments, Form C is characterized by a DSC diagram exhibiting an endothermic peak at about 151.0° C. (21.01 J/g)); about 187° C. (11 J/g) (e.g., about 186.8° C. (10.55 J/g)); about 223° C. (7 J/g) (e.g., about 223.2° C. (6.77 J/g)); and about 231° C. (120 J/g) (e.g., about 231.4° C. (120.16 J/g)).

In some embodiments, Form C is characterized by a DSC diagram exhibiting an exothermic peak at about 190° C. (4 J/g) (e.g., about 189.5° C. (3.75 J/g)). In some embodiments, Form C is characterized by a DSC diagram exhibiting an exothermic peak at about 224° C. (1 J/g) (e.g., about 224.4° C. (0.75 J/g)). In some embodiments, Form C is characterized by a DSC diagram exhibiting an exothermic peak at about 190° C. (4 J/g) (e.g., about 189.5° C. (3.75 J/g)) and about 224° C. (1 J/g) (e.g., about 224.4° C. (0.75 J/g)).

Form D

Morphic Form D of Compound 1 was characterized as a first substantially anhydrous morphic form of Compound 1. In some embodiments, morphic Form D can be prepared by heating the hemihydrate morphic Form A under a flow of dry nitrogen to about 200° C.

Figure 4:
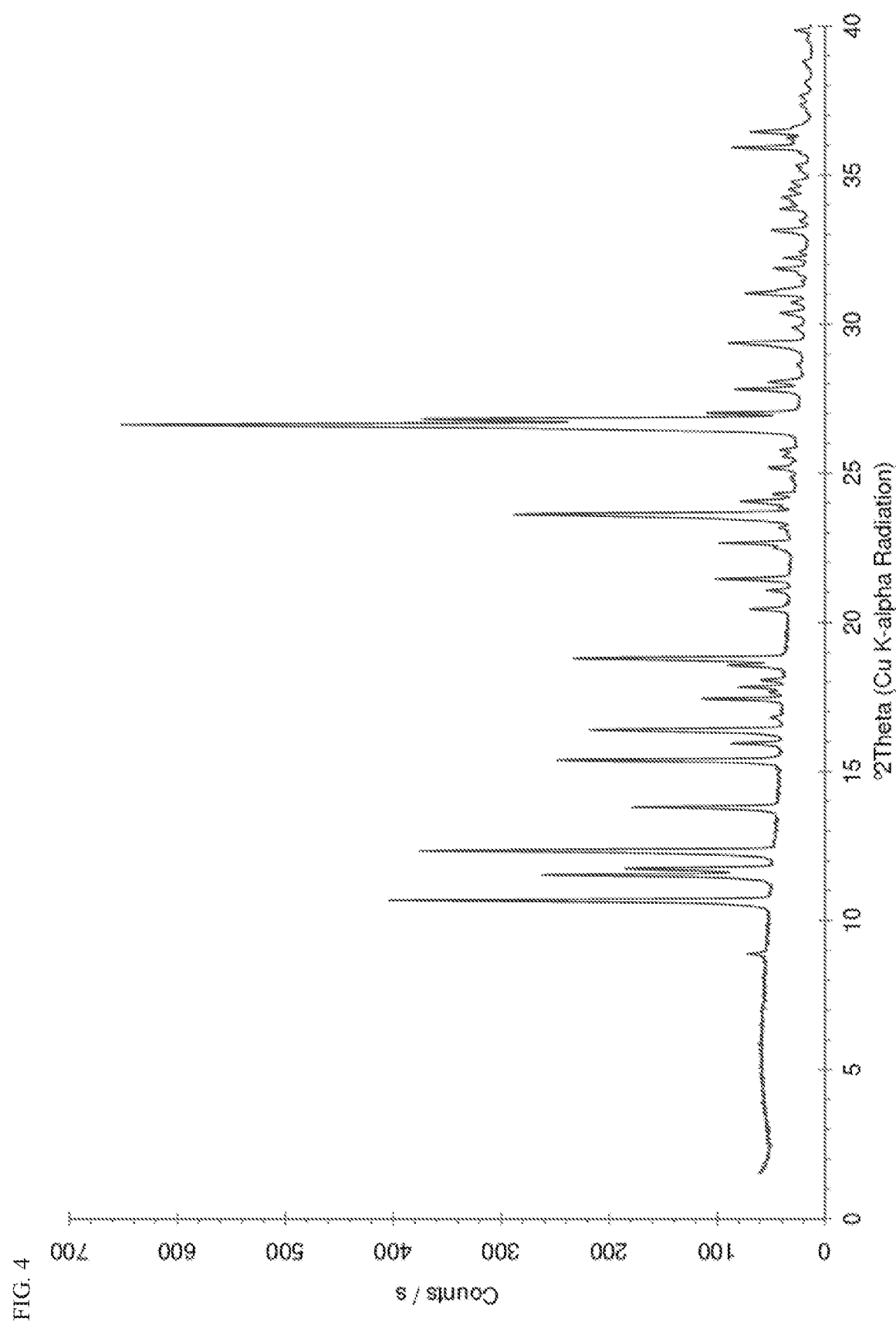
FIG. 4 is a PXRD pattern of a sample of Compound 1, Form D taken in transmission geometry.

FIG. 4 is a PXRD pattern of a sample of Compound 1, Form D taken in transmission mode. FIG. 4 was obtained using a Stoe Stadi P powder X-ray diffractometer using Cu Kα1 radiation and transmission geometry.

In some embodiments, morphic Form D can be characterized by the PXRD peaks set forth below in Table 5. For example, morphic Form D can be characterized by a PXRD peak at about 26.6 °2θ (±0.2 °2θ; ±0.1 °2θ; or ±0.0 °2θ; Cu Kα1 radiation). Form D can further be characterized by PXRD peaks at about 10.7 °2θ, 11.5 °2θ, 12.3 °2θ, 15.4 °2θ, 18.8 °2θ, 23.6 °2θ, and/or 26.8 °2θ (±0.2 °2θ; ±0.1 °2θ; or ±0.0 °2θ; Cu Kα1 radiation). Form D can further be characterized by peaks at about 11.7 °2θ, 13.8 °2θ, and/or 16.4 °2θ (±0.2 °2θ; ±0.1 °2θ; or ±0.0 °2θ; Cu Kα1 radiation).

In some embodiments, morphic Form D can be characterized by PXRD peaks at about 10.7 °2θ, about 11.5 °2θ, and about 12.3 °2θ (±0.2 °2θ; ±0.1 °2θ; or ±0.0 °2θ; Cu Kα1 radiation). In some embodiments, morphic Form D can be characterized by PXRD peaks at about 11.5 °2θ, about 12.3 °2θ, and about 15.4 °2θ (±0.2 °2θ; ±0.1 °2θ; or ±0.0 °2θ; Cu Kα1 radiation). In some embodiments, morphic Form D can be characterized by PXRD peaks at about 12.3 °2θ, about 15.4 °2θ, and about 18.8 °2θ (±0.2 °2θ; ±0.1 °2θ; or ±0.0 °2θ; Cu Kα1 radiation). In some embodiments, morphic Form D can be characterized by PXRD peaks at about 15.4 °2θ, about 18.8 °2θ, and about 23.6 °2θ (±0.2 °2θ; ±0.1 °2θ; or ±0.0 °2θ; Cu Kα1 radiation). In some embodiments, morphic Form D can be characterized by PXRD peaks at about 18.8 °2θ, about 23.6 °2θ, and about 26.6 °2θ (±0.2 °2θ; ±0.1 °2θ; or ±0.0 °2θ; Cu Kα1 radiation). In some embodiments, morphic Form D can be characterized by PXRD peaks at about 23.6 °2θ, about 26.6 °2θ, and about 26.8 °2θ (±0.2 °2θ; ±0.1 °2θ; or ±0.0 °2θ; Cu Kα1 radiation).

In some embodiments, morphic Form D can be characterized by PXRD peaks at about 26.6 °2θ and about 10.7 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ and about 11.5 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, and about 12.3 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 12.3 °2θ, and about 15.4 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 12.3 °2θ, about 15.4 °2θ, and about 18.8 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 12.3 °2θ, about 15.4 °2θ, about 18.8 °2θ, and about 23.6 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 12.3 °2θ, about 15.4 °2θ, about 18.8 °2θ, about 23.6 °2θ, and about 26.8 °2θ (±0.2 °2θ; ±0.1 °2θ; or ±0.0 °2θ; Cu Kα1 radiation).

In some embodiments, morphic Form D can be characterized by PXRD peaks at about 26.6 °2θ, about 10.7 °2θ, about 11.5 °2θ, about 11.7 °2θ, about 12.3 °2θ, about 15.4 °2θ, about 18.8 °2θ, about 23.6 °2θ, and about 26.8 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 11.7 °2θ, about 12.3 °2θ, about 13.8 °2θ, about 15.4 °2θ, about 18.8 °2θ, about 23.6 °2θ, and about 26.8 °2θ (±0.2 °2θ; ±0.1 °2θ; or ±0.0 °2θ; Cu Kα1 radiation). In some embodiments, morphic Form D can be characterized by PXRD peaks at about 26.6 °2θ, about 10.7 °2θ, about 11.5 °2θ, about 11.7 °2θ, about 12.3 °2θ, about 13.8 °2θ, about 15.4 °2θ, about 16.4, about 18.8 °2θ, about 23.6 °2θ, and about 26.8 °2θ (±0.2 °2θ; ±0.1 °2θ; or ±0.0 °2θ; Cu Kα1 radiation).

Accordingly, in some embodiments, morphic Form D can be characterized by one, two, three, four, five, six, seven, eight, nine, ten, or eleven PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by one, PXRD peak selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by two PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by three PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by four PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by five PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by six PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by seven PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by eight PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by nine PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by ten PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation). In some embodiments, morphic Form D can be characterized by eleven PXRD peaks selected from the group consisting of about 10.7 °2θ, 11.5 °2θ, 11.7 °2θ, 12.3 °2θ, 13.8 °2θ, 15.4 °2θ, 16.4 °2θ, 18.8 °2θ, 23.6 °2θ, 26.6 °2θ, and 26.8 °2θ (Cu Kα1 radiation).

TABLE 5

Representative PXRD Peaks for Morphic Form D (Cu Kα1 radiation)

| Angle (°2θ) | d value (Å) | Intensity |
|---|---|---|
| 8.9 | 9.94 | vw |
| 10.7 | 8.29 | s |
| 11.5 | 7.67 | s |
| 11.7 | 7.54 | m |
| 12.3 | 7.17 | s |
| 13.8 | 6.41 | m |
| 15.4 | 5.76 | s |
| 15.9 | 5.55 | w |
| 16.4 | 5.40 | m |
| 16.8 | 5.27 | vw |
| 17.4 | 5.08 | w |
| 17.8 | 4.97 | w |
| 18.1 | 4.91 | vw |
| 18.6 | 4.78 | w |
| 18.8 | 4.72 | s |
| 20.4 | 4.34 | w |
| 21.1 | 4.22 | vw |
| 21.4 | 4.14 | w |
| 22.7 | 3.92 | w |
| 23.2 | 3.84 | vw |

TABLE 5-continued

Representative PXRD Peaks for Morphic
Form D (Cu Kα1 radiation)

| Angle (°2θ) | d value (Å) | Intensity |
|---|---|---|
| 23.6 | 3.77 | s |
| 24.1 | 3.70 | w |
| 24.3 | 3.66 | vw |
| 25.2 | 3.53 | vw |
| 25.6 | 3.48 | vw |
| 25.8 | 3.45 | vw |
| 26.6 | 3.35 | vs |
| 26.8 | 3.32 | s |
| 27.0 | 3.30 | w |
| 27.8 | 3.20 | w |
| 28.1 | 3.18 | vw |
| 29.4 | 3.04 | w |
| 29.9 | 2.99 | vw |
| 30.4 | 2.94 | vw |
| 30.7 | 2.91 | vw |
| 31.0 | 2.88 | w |
| 31.9 | 2.81 | vw |
| 32.2 | 2.78 | vw |
| 32.4 | 2.76 | vw |
| 33.1 | 2.70 | w |
| 33.5 | 2.68 | vw |
| 33.9 | 2.64 | vw |
| 34.3 | 2.62 | vw |
| 34.8 | 2.58 | vw |
| 35.3 | 2.54 | vw |
| 35.9 | 2.50 | w |
| 36.4 | 2.46 | w |
| 37.6 | 2.39 | vw |
| 39.8 | 2.26 | vw |

Figure 11:
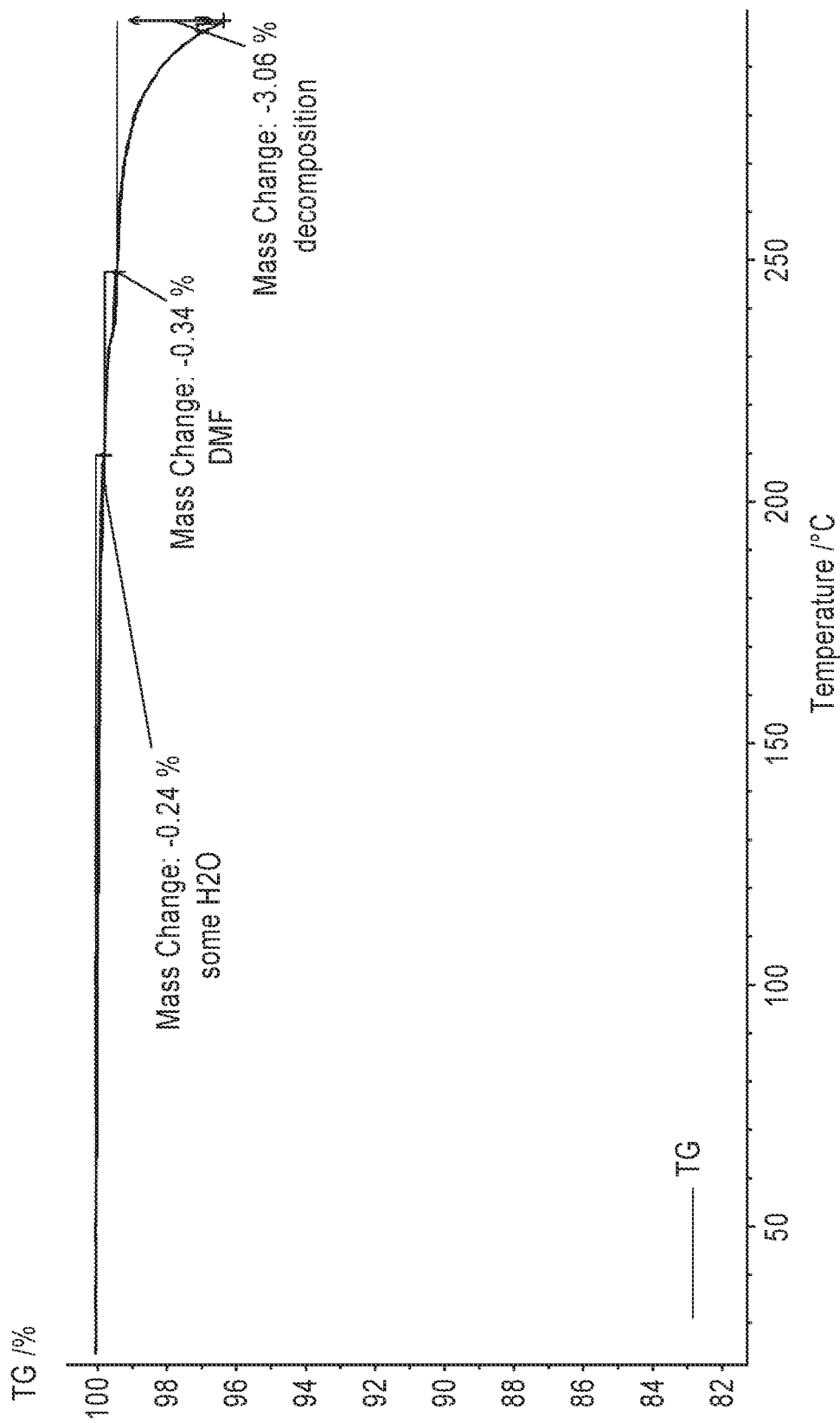
FIG. 11 is a TG-FTIR diagram of a sample of Compound 1, Form D.

FIG. 11 is a TG-FTIR diagram of a sample of Compound 1, Form D. FIG. 11 was obtained using a Netzsch TG 209, over the range of 25° C. to 300° C. The scanning speed was 10° C. per minute. As shown in FIG. 11, Form D exhibited a mass loss of about 0.2% (e.g., about 0.24%) between about 100° C. and about 210° C. Without wishing to be bound by theory, this is proposed to be due to a loss of water. Form D also exhibited a mass loss of about 0.3% (e.g., about 0.34%) between about 210° C. and about 250° C. Without wishing to be bound by theory, this is proposed to be due to a loss of DMF. Accordingly, in some embodiments, morphic Form D contains about 0.2% water (w/w). In some embodiments, morphic Form D contains about 0.3% DMF (w/w). In some embodiments, Form D contains less than 0.2% water. In some embodiments, Form D is substantially anhydrous. In some embodiments, Form D is characterized by a mass loss of about 0.3% between about 210° C. and about 250° C. (e.g., as measured by TG-FTIR). In some embodiments, Form D is characterized by a mass loss of about 0.2% between about 100° C. and about 210° C. (e.g., as measured by TG-FTIR).

Figure 18:
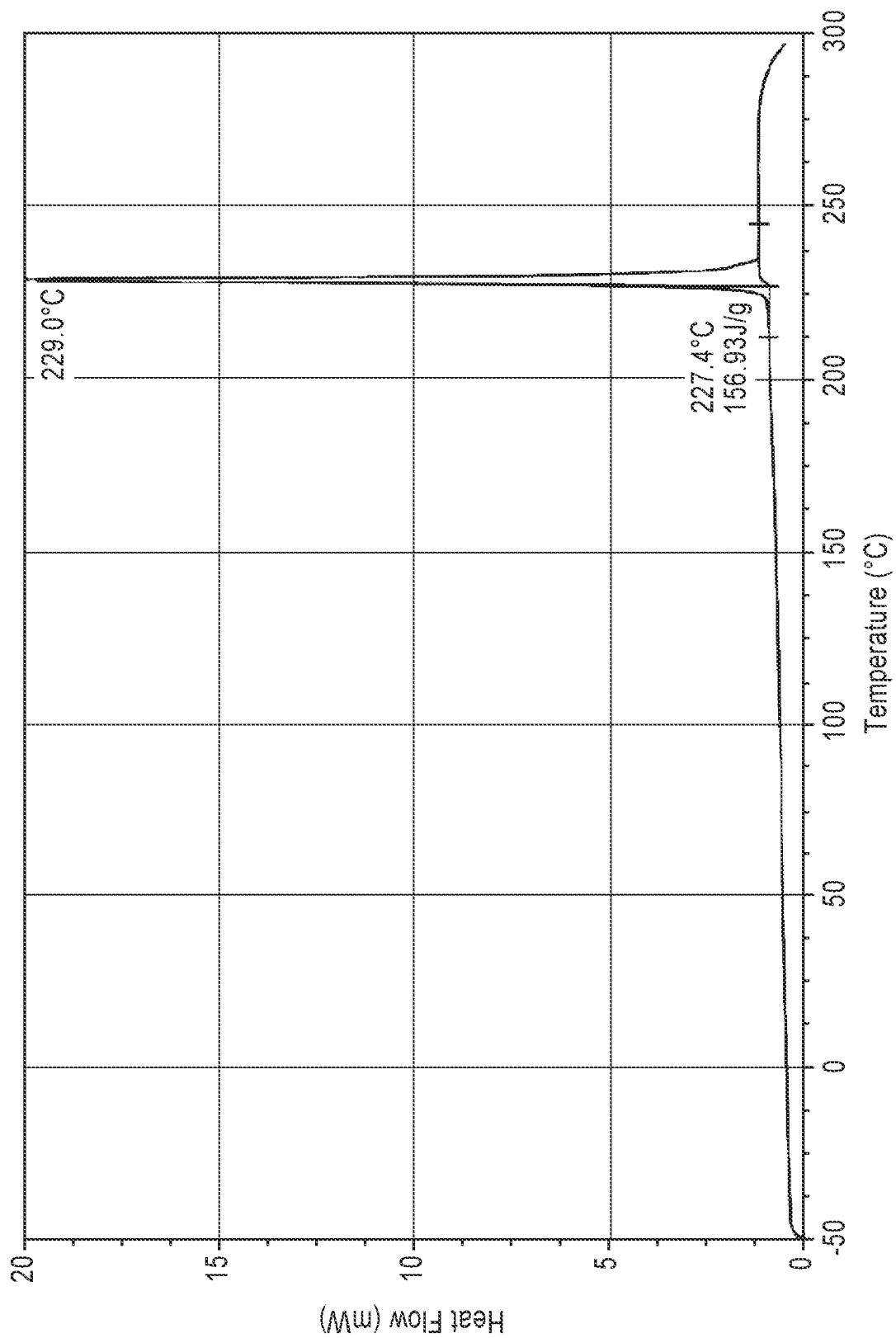
FIG. 18 is a DSC diagram of a sample of Compound 1, Form D.

FIG. 18 is a DSC diagram of a sample of Compound 1, Form D. FIG. 18 was obtained using a DSC Q2000 V24.3 with a hermetically closed gold sample pan. The heating rate was 10° C. per minute. As shown in FIG. 18, Form D exhibited an endotherm with a peak at about 229° C. (157 J/g) (e.g., about 229.0° C. (156.93 J/g)). Accordingly, in some embodiments morphic Form D is characterized by a DSC diagram exhibiting a peak at about 229° C. (157 J/g).

Figure 22A:
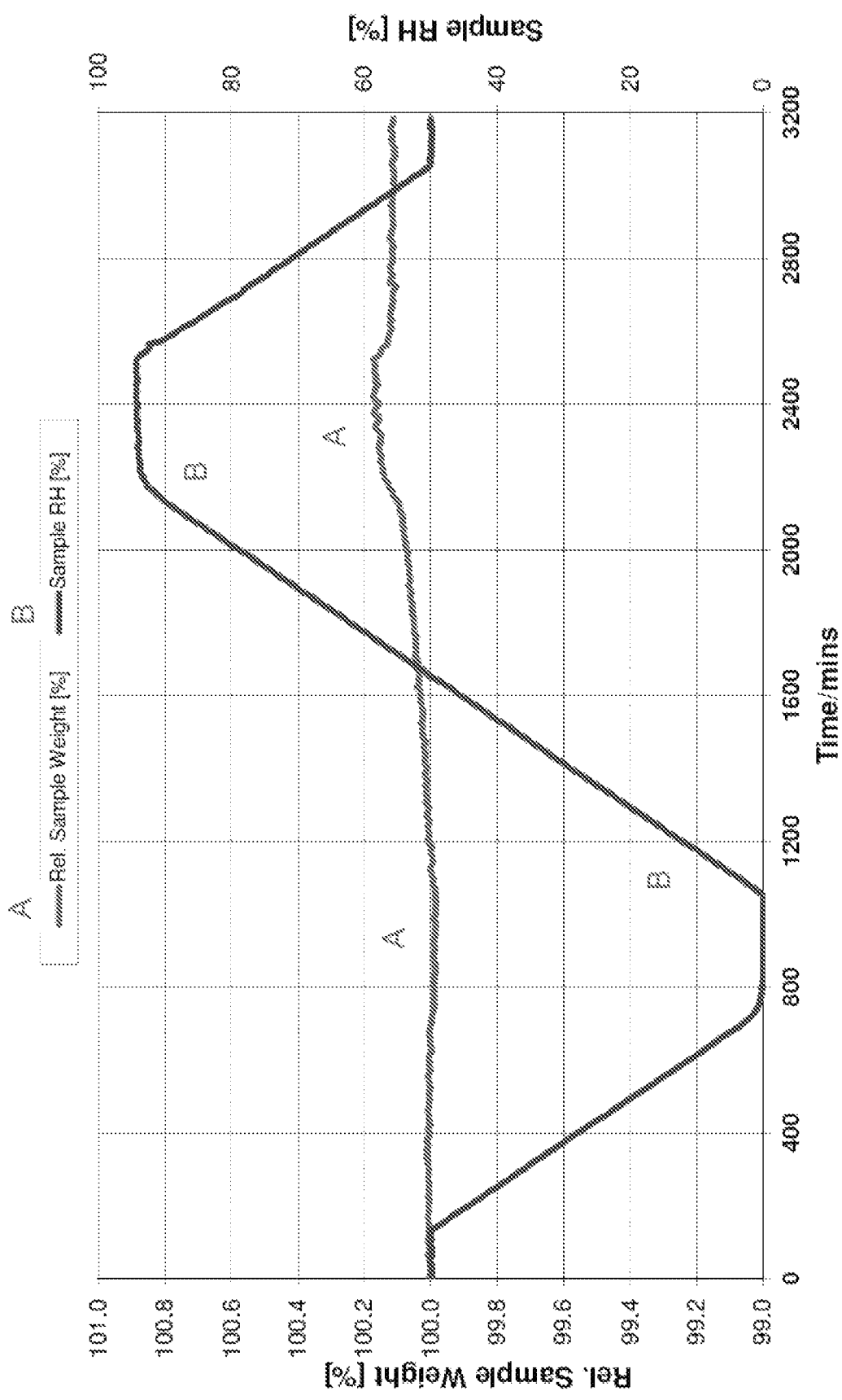
FIG. 22A is a DVS diagram of a sample of Compound 1, Form D as a function of time and the applied change in relative humidity.
Figure 22B:
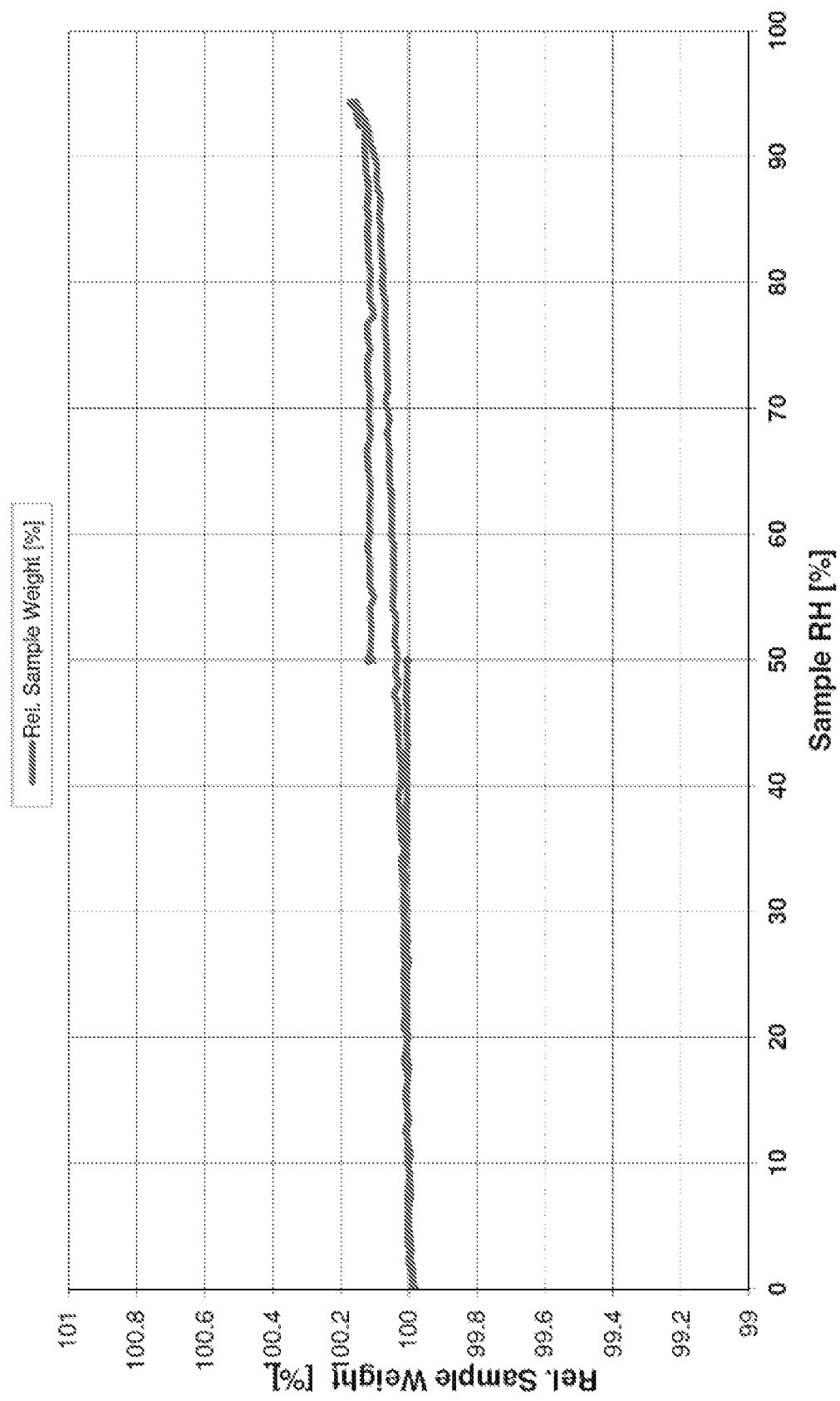
FIG. 22B is a DVS diagram of a sample of Compound 1, Form D as a function of the applied relative humidity.

FIG. 22A is a DVS diagram of a sample of Compound 1, Form D as a function of time and the applied change in relative humidity. Line A represents the relative weight of the sample at each relative humidity. Line B represents the applied relative humidity (i.e., the applied measurement program). FIG. 22B is a DVS diagram of a sample of Compound 1, Form D as a function of the applied relative humidity. FIG. 22A and FIG. 22B were obtained using a Sorptions Prufsystem ProUmid system using a scan rate of 5% relative humidity per hour at a temperature of 25° C. As shown in FIG. 22A and FIG. 22B, the relative sample weight of Form D changed as a function of the relative humidity of the environment. Without wishing to be bound by theory, this suggests that Form D is hygroscopic (e.g., more hygroscopic than Form A). In some embodiments, Form D is slightly hygroscopic.

Form E

Morphic Form E of Compound 1 was characterized as a second substantially anhydrous morphic form of Compound 1. In some embodiments, morphic Form E can be prepared by heating the methanol hemisolvate morphic Form B under a flow of dry nitrogen to about 200° C.

Figure 5A:
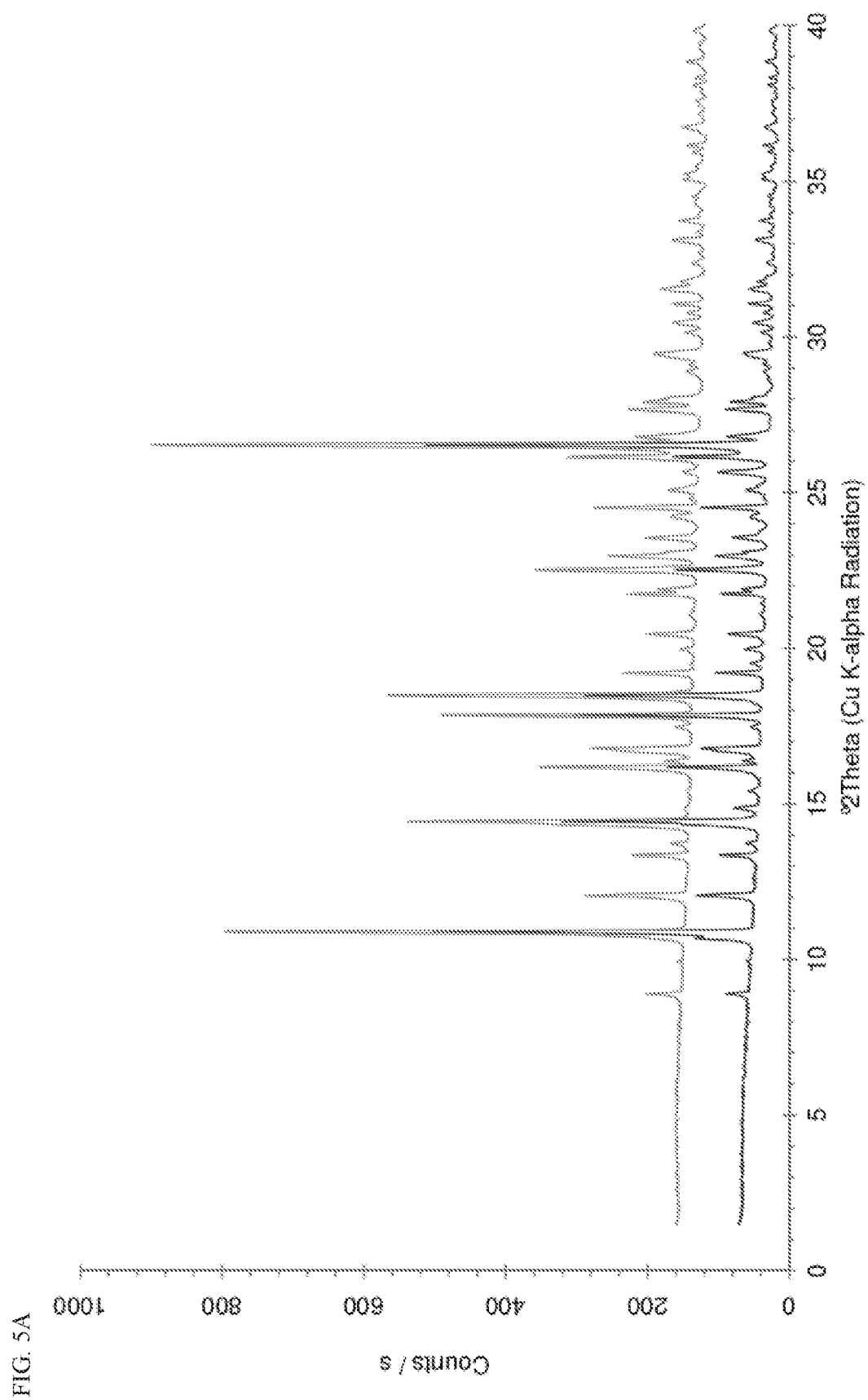
FIG. 5A is a PXRD pattern of two samples of Compound 1, Form E taken in transmission geometry.
Figure 5B:
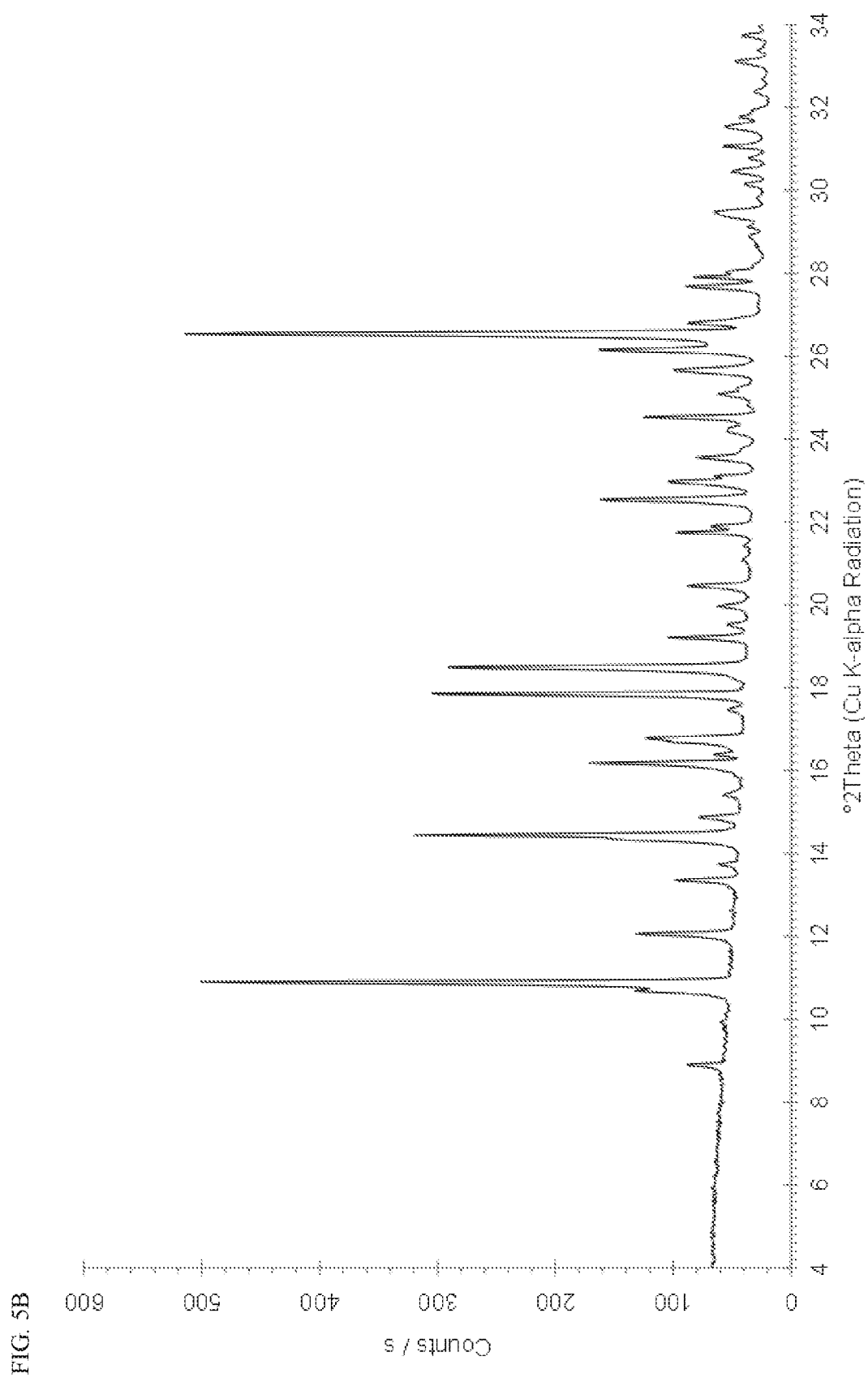
FIG. 5B is a PXRD pattern of a sample of Compound 1, Form E, taken in transmission geometry.

FIG. 5A is a PXRD pattern of two samples of Compound 1, Form E taken in transmission mode. Both of the PXRD patterns in FIG. 5 were obtained using a Stoe Stadi P powder X-ray diffractometer using Cu Kα1 radiation and transmission geometry. FIG. 5B is a PXRD pattern of Form E measured from 4 to 34 °2θ.

In some embodiments, morphic Form E can be characterized by the PXRD peaks set forth below in Table 6. For example, morphic Form E can be characterized by PXRD peaks at about 10.9 °2θ and/or 26.5 °2θ (±0.2 °2θ; ±0.1 °2θ; or ±0.0 °2θ; Cu Kα1 radiation). Morphic Form E can further be characterized by a PXRD peak at about 14.4 °2θ, 17.8 °2θ, and/or 18.5 °2θ (±0.2 °2θ; ±0.1 °2θ; or ±0.0 °2θ; Cu Kα1 radiation). Morphic Form E can further be characterized by a PXRD peak at about 10.7 °2θ, 12.1 °2θ, 16.2 °2θ, 16.8 °2θ, 22.5 °2θ, 24.5 °2θ, and/or 26.2 °2θ (±0.2 °2θ; ±0.1 °2θ; or ±0.0 °2θ; Cu Kα1 radiation).

In some embodiments, morphic Form E can be characterized by PXRD peaks at about 10.9 °2θ, about 14.4 °2θ, and about 17.8 °2θ (±0.2 °2θ; ±0.1 °2θ; or ±0.0 °2θ; Cu Kα1 radiation). In some embodiments, morphic Form E can be characterized by PXRD peaks at about 14.4 °2θ, about 17.8 °2θ, and about 18.5 °2θ (±0.2 °2θ; ±0.1 °2θ; or ±0.0 °2θ; Cu Kα1 radiation). In some embodiments, morphic Form E can be characterized by PXRD peaks at about 17.8 °2θ, about 18.5 °2θ, and about 26.5 °2θ (±0.2 °2θ; ±0.1 °2θ; or ±0.0 °2θ; Cu Kα1 radiation).

In some embodiments, morphic Form E can be characterized by PXRD peaks at about 10.9 °2θ and about 26.5 °2θ (±0.2 °2θ; ±0.1 °2θ; or ±0.0 °2θ; Cu Kα1 radiation). In some embodiments, morphic Form E can be characterized by PXRD peaks at about 10.9 °2θ, about 14.4 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.9 °2θ, about 14.4 °2θ, about 17.8 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.9 °2θ, about 14.4 °2θ, about 17.8 °2θ, about 18.5 °2θ, and about 26.5 °2θ (±0.2 °2θ; ±0.1 °2θ; or ±0.0 °2θ; Cu Kα1 radiation).

In some embodiments, morphic Form E can be characterized by PXRD peaks at about 10.7 °2θ, about 10.9 °2θ, about 14.4 °2θ, about 17.8 °2θ, about 18.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 17.8 °2θ, about 18.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 16.2 °2θ, about 17.8 °2θ, about 18.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 16.2 °2θ, about 16.8 °2θ, about 17.8 °2θ, about 18.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 16.2 °2θ, about 16.8 °2θ, about 17.8 °2θ, about 18.5 °2θ, about 22.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 16.2 °2θ, about 16.8 °2θ, about 17.8 °2θ, about 18.5 °2θ, about 22.5 °2θ, about 24.5 °2θ, and about 26.5 °2θ (±0.2 °2θ; ±0.1 °2θ; or ±0.0 °2θ; Cu Kα1 radiation). In some embodiments, morphic Form E can be characterized by PXRD peaks at about 10.7 °2θ, about 10.9 °2θ, about 12.1 °2θ, about 14.4 °2θ, about 16.2 °2θ, about 16.8 °2θ, about 17.8 °2θ, about 18.5 °2θ, about 22.5 °2θ, about 24.5 °2θ, about 26.2 °2θ, and about 26.5 °2θ (±0.2 °2θ; ±0.1 °2θ; or ±0.0 °2θ; Cu Kα1 radiation).

Accordingly, in some embodiments, morphic Form E can be characterized by one, two, three, four, five, six, seven, eight, nine, ten, eleven, or twelve PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by one PXRD peak selected from about 10.7, 10.9, 12.1, 14.4, 16.2, 16.8, 18.5, 22.5, 24.5, 26.2, and 26.5 °2θ (Cu Kα1 radiation). In some embodiments, morphic Form E can be characterized by two PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by three PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by four PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by five PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by six PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by seven PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by eight PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by nine PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by ten PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by eleven PXRD peaks selected from about 10.7, 10.9, 12.1, 14.4, 16.2, 16.8, 17.8, 18.5, 22.5, 24.5, 26.2, and 26.5 °2θ (Cu Kα1 radiation). In some embodiments, morphic Form E can be characterized by twelve PXRD peaks selected from about 10.7, 10.9, 12.1, 14.4, 16.2, 16.8, 17.8, 18.5, 22.5, 24.5, 26.2, and 26.5 °2θ (Cu Kα1 radiation).

TABLE 6

Representative PXRD Peaks for Morphic Form E (Cu Kα1 radiation)

| Angle (°2θ) | d value (Å) | Intensity |
|---|---|---|
| 8.9 | 9.93 | w |
| 10.7 | 8.28 | m |
| 10.9 | 8.12 | vs |
| 12.1 | 7.34 | m |
| 13.3 | 6.63 | w |
| 13.7 | 6.45 | vw |
| 14.4 | 6.13 | s |
| 14.9 | 5.95 | w |
| 15.4 | 5.75 | vw |
| 16.2 | 5.47 | m |
| 16.4 | 5.40 | w |
| 16.8 | 5.28 | m |
| 17.5 | 5.07 | vw |
| 17.8 | 4.97 | s |
| 18.5 | 4.79 | s |
| 19.2 | 4.62 | w |
| 19.5 | 4.55 | vw |
| 20.0 | 4.44 | w |
| 20.4 | 4.34 | w |
| 21.8 | 4.08 | w |
| 21.9 | 4.06 | w |
| 22.5 | 3.94 | m |
| 23.0 | 3.87 | w |
| 23.5 | 3.78 | w |
| 24.2 | 3.67 | vw |
| 24.5 | 3.63 | m |
| 25.1 | 3.55 | w |
| 25.7 | 3.47 | w |
| 26.2 | 3.40 | m |
| 26.5 | 3.36 | vs |
| 26.8 | 3.32 | w |
| 27.7 | 3.22 | w |
| 27.9 | 3.19 | w |
| 29.5 | 3.03 | w |
| 30.1 | 2.96 | vw |
| 30.5 | 2.93 | w |
| 30.8 | 2.90 | vw |
| 31.1 | 2.88 | w |
| 31.5 | 2.83 | w |
| 32.4 | 2.76 | vw |
| 33.1 | 2.70 | w |
| 33.7 | 2.65 | vw |
| 34.5 | 2.60 | vw |
| 35.1 | 2.56 | vw |
| 36.0 | 2.50 | vw |
| 36.2 | 2.48 | vw |
| 36.7 | 2.44 | vw |
| 38.1 | 2.36 | vw |
| 38.3 | 2.35 | vw |
| 38.9 | 2.32 | vw |
| 39.9 | 2.26 | vw |

Figure 12:
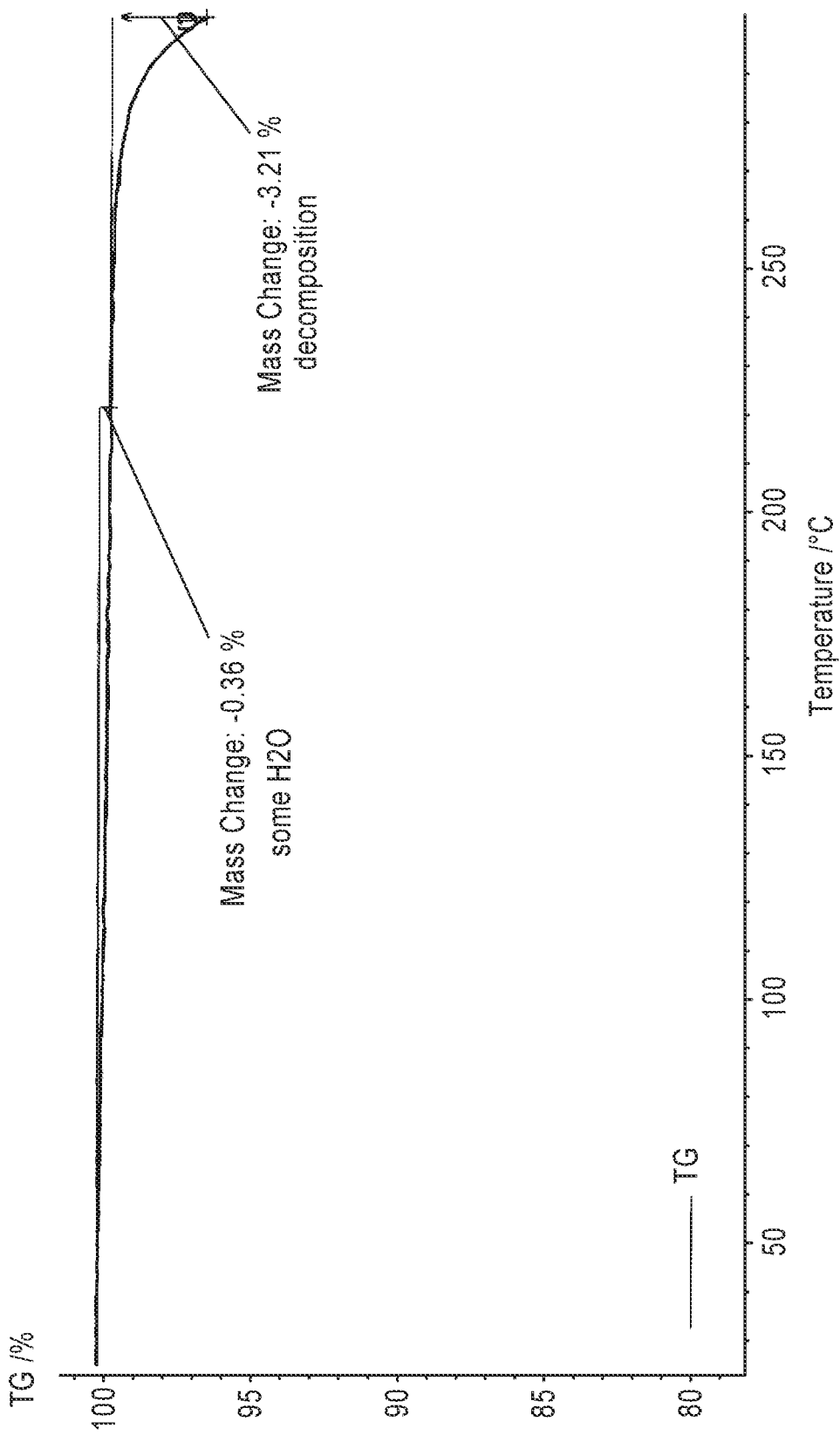
FIG. 12 is a TG-FTIR diagram of a sample of Compound 1, Form E.

FIG. 12 is a TG-FTIR diagram of a sample of Compound 1, Form E. FIG. 12 was obtained using a Netzsch TG 209, over the range of 25° C. to 300° C. The scanning speed was 10° C. per minute. As shown in FIG. 12, Form E shows a mass change of about 0.4% (e.g., about 0.36%) between about 50° C. and about 215° C. Without wishing to be bound by theory, this is proposed to be due to a loss of trace water. Accordingly, in some embodiments, morphic Form E contains about 0.4% water (w/w). Accordingly, in some embodiments, morphic Form E is characterized by a mass loss of about 0.4% between about 50° C. and about 215° C. (e.g., as measured by TG-FTIR).

Figure 19:
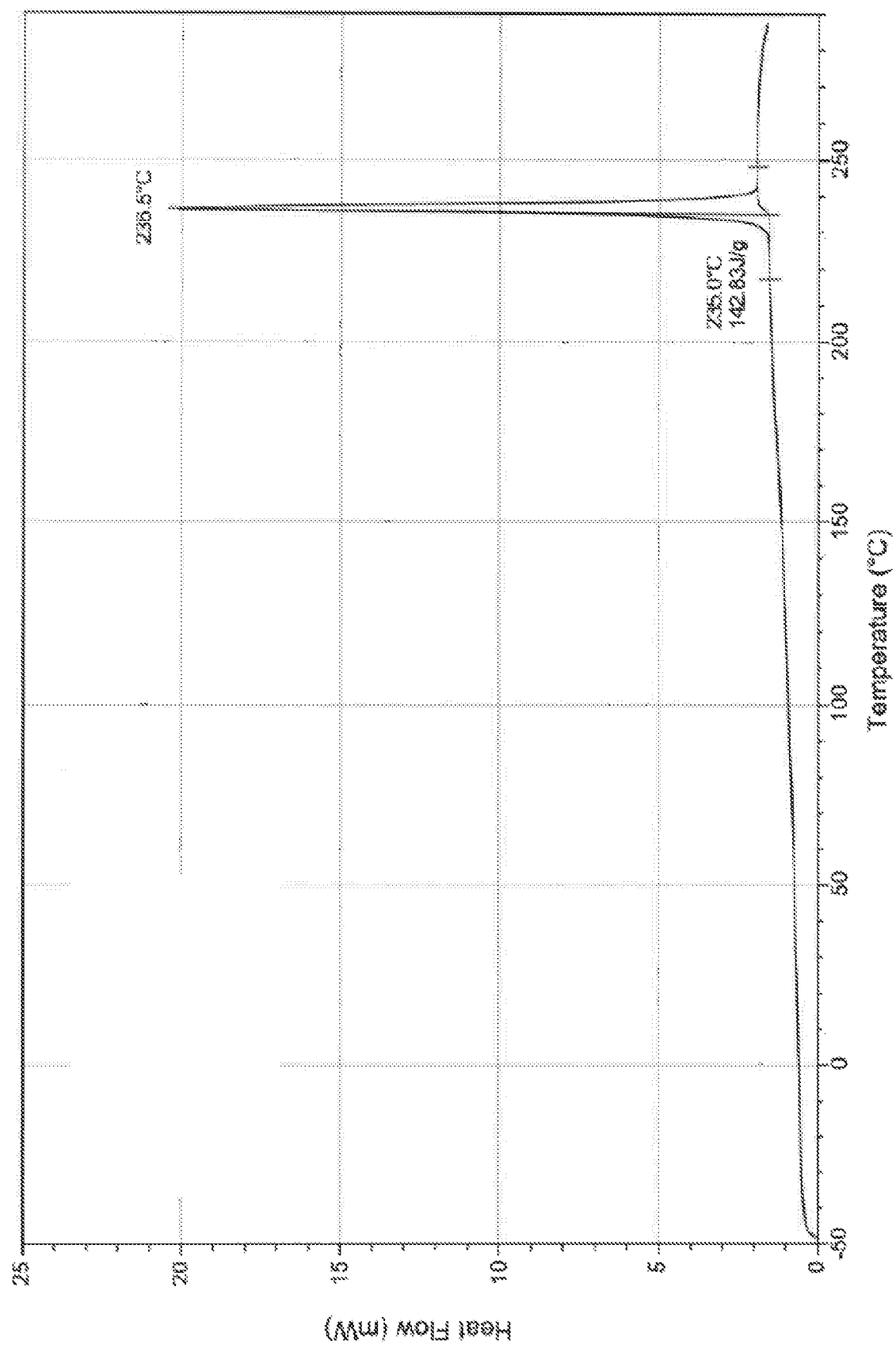
FIG. 19 is a DSC diagram of a sample of Compound 1, Form E.

FIG. 19 is a DSC diagram of a sample of Compound 1, Form E. FIG. 19 was obtained using a DSC Q2000 V24.3 with a hermetically closed gold sample pan. The heating rate was 10° C. per minute. As shown in FIG. 19, Form E shows an endotherm with a peak at about 237° C. (143 J/g) (e.g., about 236.5° C. (142.83 J/g)). Accordingly, in some embodiments, morphic Form E is characterized by a DSC diagram exhibiting a DSC peak at about 237° C. (143 J/g).

Figure 23A:
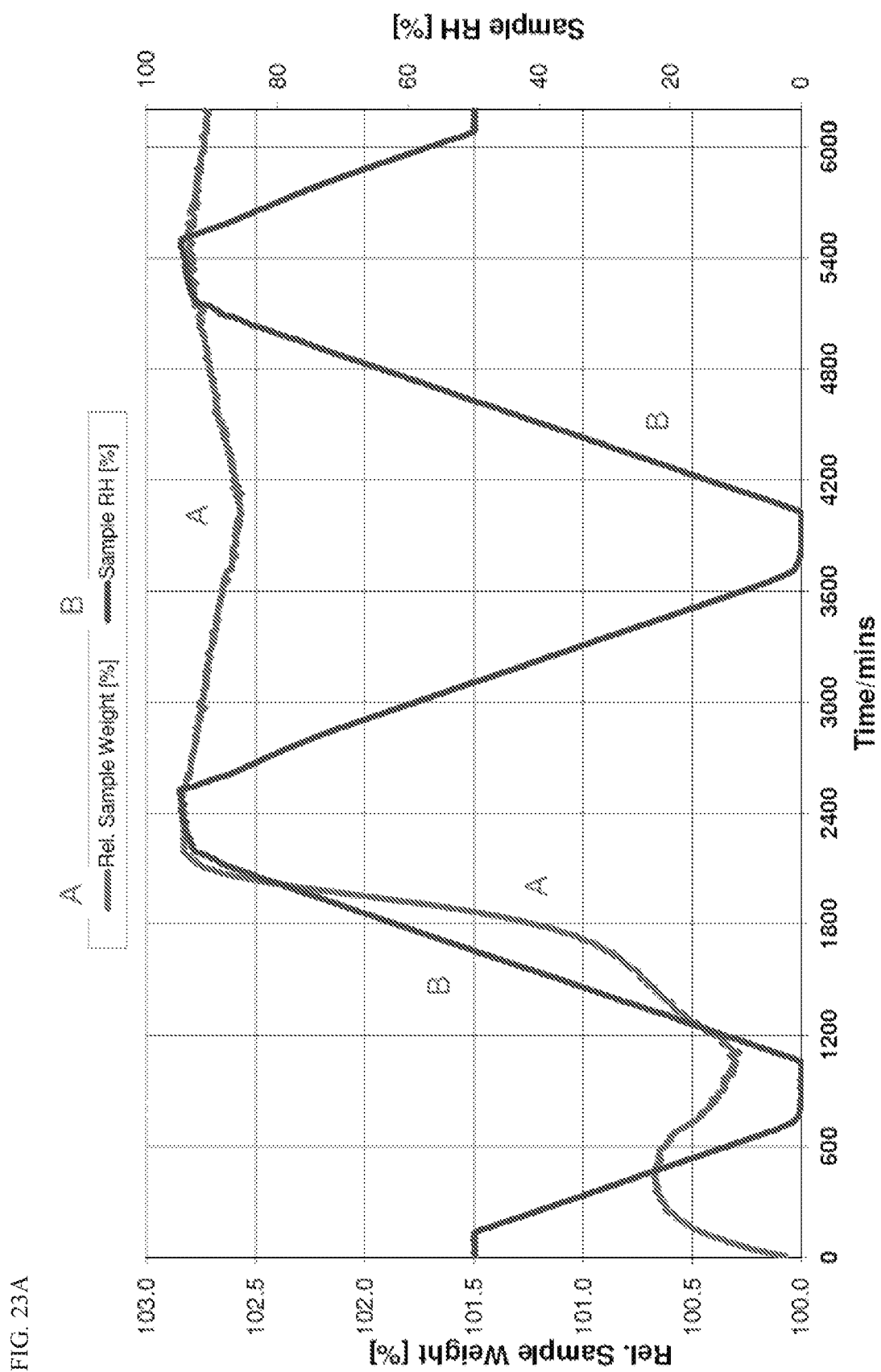
FIG. 23A is a DVS diagram of a sample of Compound 1, Form E as a function of time and the applied change in relative humidity.
Figure 23B:
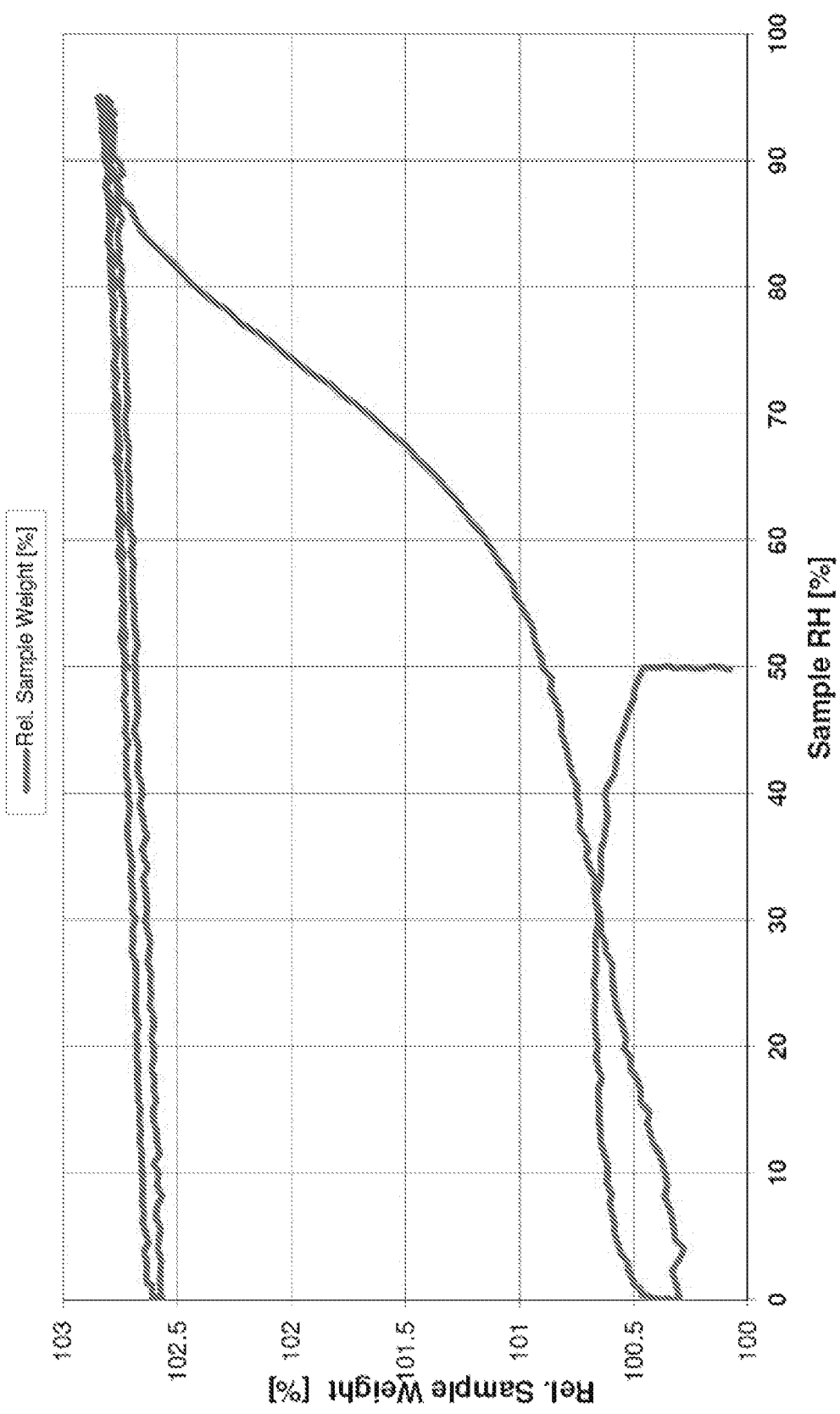
FIG. 23B is a DVS diagram of a sample of Compound 1, Form E as a function of the applied relative humidity.

FIG. 23A is a DVS diagram of a sample of Compound 1, Form E as a function of time and the applied change in relative humidity. Line A represents the relative weight of the sample at each relative humidity. Line B represents the applied relative humidity (i.e., the applied measurement program). FIG. 23B is a DVS diagram of a sample of Compound 1, Form E as a function of the applied relative humidity. FIG. 23A and FIG. 23B were obtained using a Sorptions Prufsystem ProUmid system using a scan rate of 5% relative humidity per hour at a temperature of 25° C.

As shown in FIG. 23A and FIG. 23B, the mass of Form E fluctuated as a function of the relative humidity of the environment. Without wishing to be bound by theory, this suggests that Form E is hygroscopic (e.g., more hygroscopic than morphic Form A). Additionally, it was found that under the conditions of the DVS analysis, morphic Form E was transformed into Form A. Accordingly, in some embodiments, morphic Form E can be converted to Form A in the presence of high relative humidity, for example at about 25° C. and about 50% relative humidity or above (e.g., under the conditions of dynamic water vapor sorption experiments).

Form F

Morphic Form F of Compound 1 was preliminarily characterized as a 2-propanol solvate form of Compound 1. In some embodiments, morphic Form F can be prepared dissolving Compound 1 in DMSO and precipitating Compound 1 at room temperature using 2-propanol.

Figure 6:
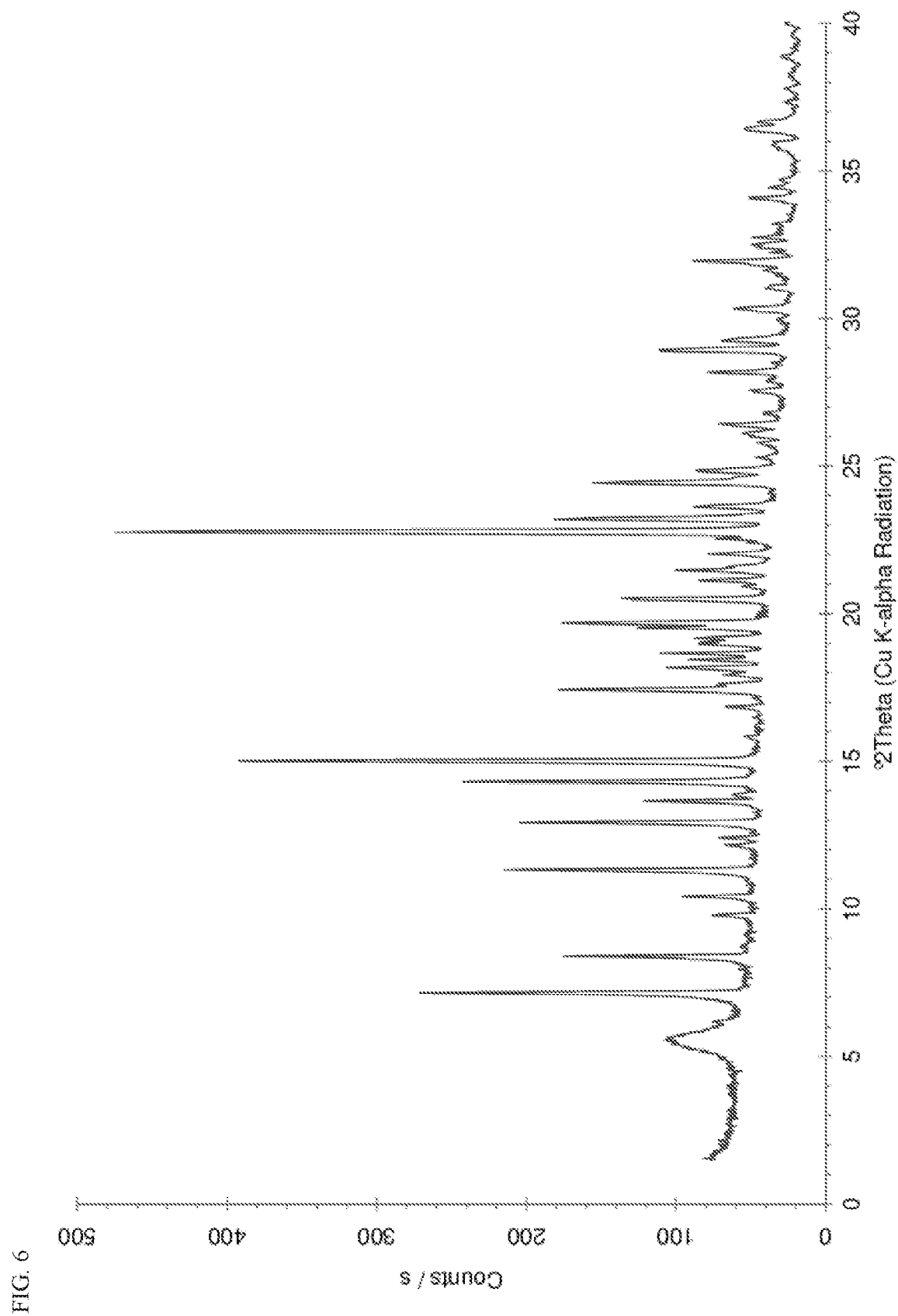
FIG. 6 is a PXRD pattern of a sample of Compound 1, Form F taken in transmission geometry between 0 °2θ and 40 °2θ.

FIG. 6 is a PXRD pattern of a sample of Compound 1, Form F taken in transmission mode. FIG. 6 was obtained using a Stoe Stadi P powder X-ray diffractometer using Cu Kα1 radiation and transmission geometry.

In some embodiments, morphic Form F can be characterized by the PXRD peaks set forth below in Table 7. For example, Form F can be characterized by PXRD peaks at about 15.0 and/or 22.8 °2θ (Cu Kα1 radiation). Form F can further be characterized by PXRD peaks at about 7.1 °2θ, 11.3 °2θ, 12.9 °2θ, 14.3 °2θ, 17.4 °2θ, 19.7 °2θ, and/or 23.2 °2θ (Cu Kα1 radiation). Form F can further be characterized by PXRD peaks at about 8.4 °2θ, 13.7 °2θ, 18.7 °2θ, 19.5 °2θ, 20.5 °2θ, 24.4 °2θ and/or 28.9 °2θ (Cu Kα1 radiation).

In some embodiments, morphic Form F can be characterized by PXRD peaks at about 7.1 °2θ, about 11.3 °2θ, and about 12.9 °2θ (±0.2 °2θ; ±0.1 °2θ; or ±0.0 °2θ; Cu Kα1 radiation). In some embodiments, morphic Form F can be characterized by PXRD peaks at about 11.3 °2θ, about 12.9 °2θ, and about 14.3 °2θ (±0.2 °2θ; ±0.1 °2θ; or ±0.0 °2θ; Cu Kα1 radiation). In some embodiments, morphic Form F can be characterized by PXRD peaks at about 12.9 °2θ, about 14.3 °2θ, and about 15.0 °2θ (±0.2 °2θ; ±0.1 °2θ; or ±0.0 °2θ; Cu Kα1 radiation). In some embodiments, morphic Form F can be characterized by PXRD peaks at about 14.3 °2θ, about 15.0 °2θ, and about 17.4 °2θ (±0.2 °2θ; ±0.1 °2θ; or ±0.0 °2θ; Cu Kα1 radiation). In some embodiments, morphic Form F can be characterized by PXRD peaks at about 15.0 °2θ, about 17.4 °2θ, and about 19.7 °2θ (±0.2 °2θ; ±0.1 °2θ; or ±0.0 °2θ; Cu Kα1 radiation). In some embodiments, morphic Form F can be characterized by PXRD peaks at about 17.4 °2θ, about 19.7 °2θ, and about 22.8 °2θ (±0.2 °2θ; ±0.1 °2θ; or ±0.0 °2θ; Cu Kα1 radiation). In some embodiments, morphic Form F can be characterized by PXRD peaks at about 19.7 °2θ, about 22.8 °2θ, and about 23.2 °2θ (±0.2 °2θ; ±0.1 °2θ; or ±0.0 °2θ; Cu Kα1 radiation).

In some embodiments, morphic Form F can be characterized by PXRD peaks at about 15.0 °2θ and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 15.0 °2θ and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 15.0 °2θ and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 12.9 °2θ, about 15.0 °2θ and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 12.9 °2θ, about 14.3 °2θ, about 15.0 °2θ and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 12.9 °2θ, about 14.3 °2θ, about 15.0 °2θ, about 17.4 °2θ, and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 12.9 °2θ, about 14.3 °2θ, about 15.0 °2θ, about 17.4 °2θ, about 19.7 °2θ, and about 22.8 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 11.3 °2θ, about 12.9 °2θ, about 14.3 °2θ, about 15.0 °2θ, about 17.4 °2θ, about 19.7 °2θ, about 22.8 °2θ, and about 23.2 °2θ (±0.2 °2θ; ±0.1 °2θ; or ±0.0 °2θ; Cu Kα1 radiation).

In some embodiments, morphic Form F can be characterized by PXRD peaks at about 7.1 °2θ, about 8.4 °2θ, about 11.3 °2θ, about 12.9 °2θ, about 14.3 °2θ, about 15.0 °2θ, about 17.4 °2θ, about 19.7 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 19.7 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 18.7 °2θ, about 19.7 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 18.7 °2θ, about 19.5 °2θ, about 19.7 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 18.7 °2θ, about 19.5 °2θ, about 19.7 °2θ, about 20.5 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 18.7 °2θ, about 19.5 °2θ, about 19.7 °2θ, about 20.5 °2θ, about 22.8 °2θ, about 23.2 °2θ, and about 24.4 °2θ (±0.2 °2θ; ±0.1 °2θ; or ±0.0 °2θ; Cu Kα1 radiation). In some embodiments, morphic Form F can be characterized by PXRD peaks at about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 18.7 °2θ, about 19.5 °2θ, about 19.7 °2θ, about 20.5 °2θ, about 22.8 °2θ, about 23.2 °2θ, about 24.4 °2θ, and about 28.9 °2θ (±0.2 °2θ; ±0.1 °2θ; or ±0.0 °2θ; Cu Kα1 radiation).

Accordingly, in some embodiments, morphic Form F is characterized by one, two, three, four, five, six, seven, eight, nine, ten, eleven, twelve, thirteen, fourteen, fifteen or sixteen peaks selected from about 7.1, 8.4, 11.3, 12.9, 13.7, 14.3, 15.0, 17.4, 18.7, 19.5, 19.7, 20.5, 22.8, 23.2, 24.4, and 28.9 °2θ (Cu Kα1 radiation).

In some embodiments, morphic Form F is characterized by one peak selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by two peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by three peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by four peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by five peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by six peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by seven peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by eight peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by nine peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by ten peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by eleven peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by twelve peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by thirteen peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by fourteen peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by fifteen peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation). In some embodiments, morphic Form F is characterized by sixteen peaks selected from about 7.1 °2θ, 8.4 °2θ, 11.3 °2θ, 12.9 °2θ, 13.7 °2θ, 14.3 °2θ, 15.0 °2θ, 17.4 °2θ, 18.7 °2θ, 19.5 °2θ, 19.7 °2θ, 20.5 °2θ, 22.8 °2θ, 23.2 °2θ, 24.4 °2θ, and 28.9 °2θ (±0.2 °2θ; ±0.1 °2θ; or ±0.0 °2θ; Cu Kα1 radiation).

TABLE 7

Representative PXRD Peaks for Morphic Form F (Cu Kα1 radiation)

| Angle (°2θ) | d value (Å) | Intensity |
| --- | --- | --- |
| 7.1 | 12.37 | s |
| 8.4 | 10.52 | m |
| 9.8 | 9.03 | w |
| 10.4 | 8.49 | w |
| 11.3 | 7.81 | s |
| 12.1 | 7.28 | vw |
| 12.4 | 7.12 | w |
| 12.9 | 6.84 | s |
| 13.7 | 6.48 | m |
| 14.3 | 6.19 | s |
| 15.0 | 5.90 | vs |
| 16.8 | 5.26 | w |
| 17.4 | 5.08 | s |
| 17.9 | 4.94 | w |
| 18.2 | 4.88 | w |
| 18.4 | 4.81 | w |
| 18.7 | 4.75 | m |
| 19.0 | 4.67 | w |
| 19.5 | 4.54 | m |
| 19.7 | 4.50 | s |
| 20.5 | 4.33 | m |
| 21.1 | 4.20 | w |
| 21.5 | 4.14 | w |
| 22.0 | 4.03 | w |
| 22.8 | 3.90 | vs |
| 23.2 | 3.83 | s |
| 23.6 | 3.76 | w |
| 24.4 | 3.64 | m |
| 24.8 | 3.58 | w |
| 26.1 | 3.41 | w |
| 26.4 | 3.37 | w |

TABLE 7-continued

Representative PXRD Peaks for Morphic Form F (Cu Kα1 radiation)

| Angle (°2θ) | d value (Å) | Intensity |
|---|---|---|
| 27.5 | 3.24 | w |
| 28.2 | 3.16 | w |
| 28.9 | 3.08 | m |
| 29.3 | 3.05 | w |
| 30.3 | 2.94 | w |
| 31.1 | 2.88 | vw |
| 32.0 | 2.80 | w |
| 32.5 | 2.75 | w |
| 32.7 | 2.73 | w |
| 34.1 | 2.63 | w |
| 34.4 | 2.60 | vw |
| 36.4 | 2.46 | w |

Figure 13:
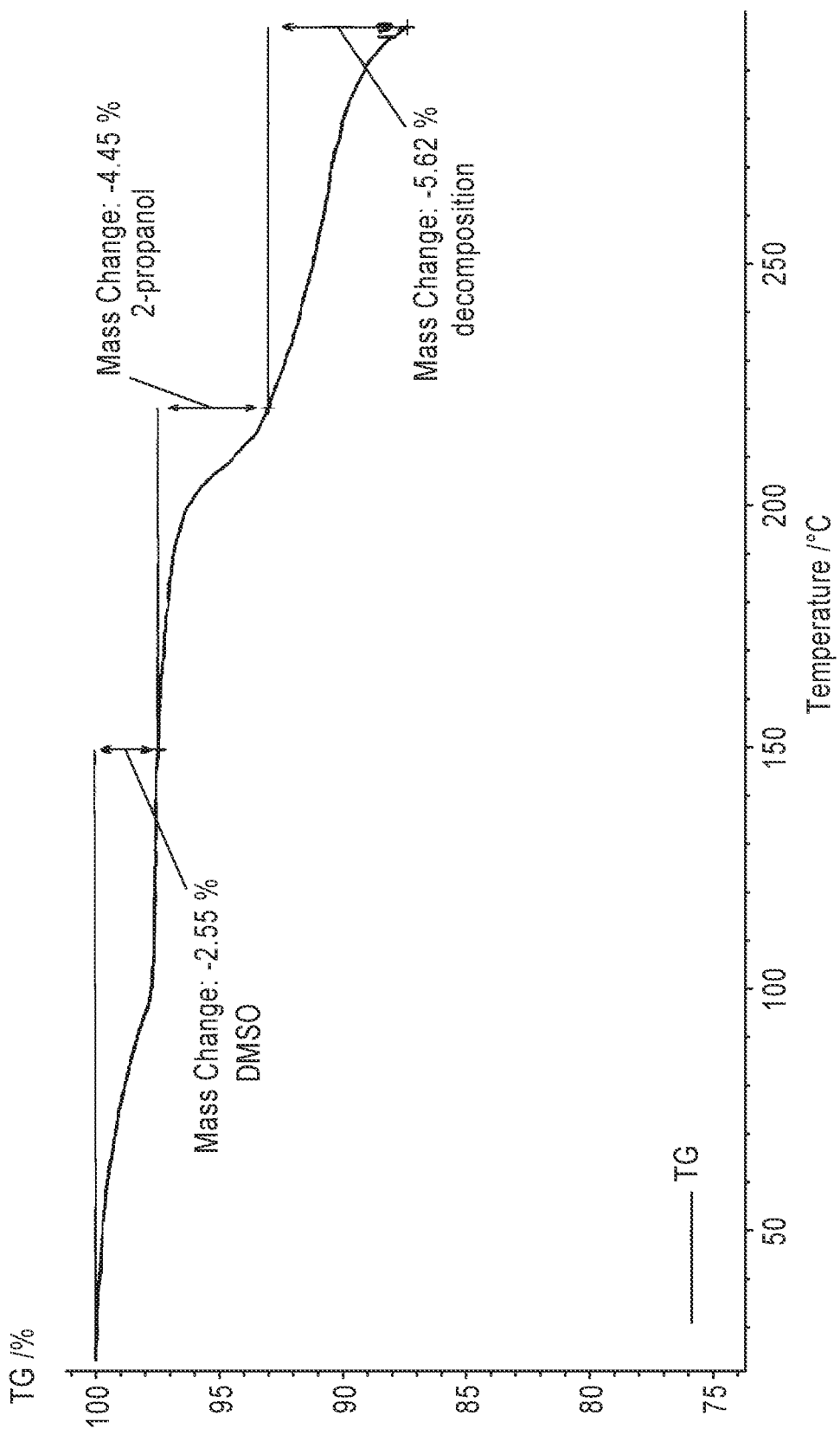
FIG. 13 is a TG-FTIR diagram of a sample of Compound 1, Form F.

FIG. 13 is a TG-FTIR diagram of a sample of Compound 1, Form F. FIG. 13 was obtained using a Netzsch TG 209, over the range of 25° C. to 300° C. The scanning speed was 10° C. per minute. As shown in FIG. 13, Form F has a mass loss change of about 2.5% (e.g., about 2.55%) between about 40° C. and about 150° C. Without wishing to be bound by theory, this mass loss is proposed to be due to the loss of DMSO. Form F also shows a mass loss of about 4.5% (e.g., about 4.45%) between about 150° C. and about 220° C. Without wishing to be bound by theory, this is proposed to be due to a loss of 2-propanol. Accordingly, in some embodiments, morphic Form F contains DMSO and/or 2-propanol. Accordingly, in some embodiments, morphic Form F is characterized by a mass loss of about 2.5% between about 40° C. and about 150° C. (e.g., as measured by TG-FTIR). In some embodiments, morphic Form F is characterized by a mass loss of about 4.5% between about 150° C. and about 220° C. (e.g., as measured by TG-FTIR).

Form G

Morphic Form G of Compound 1 was preliminarily characterized as a DMSO solvate form of Compound 1. In some embodiments, morphic Form G can be prepared dissolving Compound 1 in DMSO and precipitating Compound 1 at room temperature using acetone. Without wishing to be bound by theory, form F and Form G show similar XRPD patterns but contain different solvents. Accordingly, without wishing to be bound by theory, Form F and Form G are isomorphous solvates.

Figure 7:
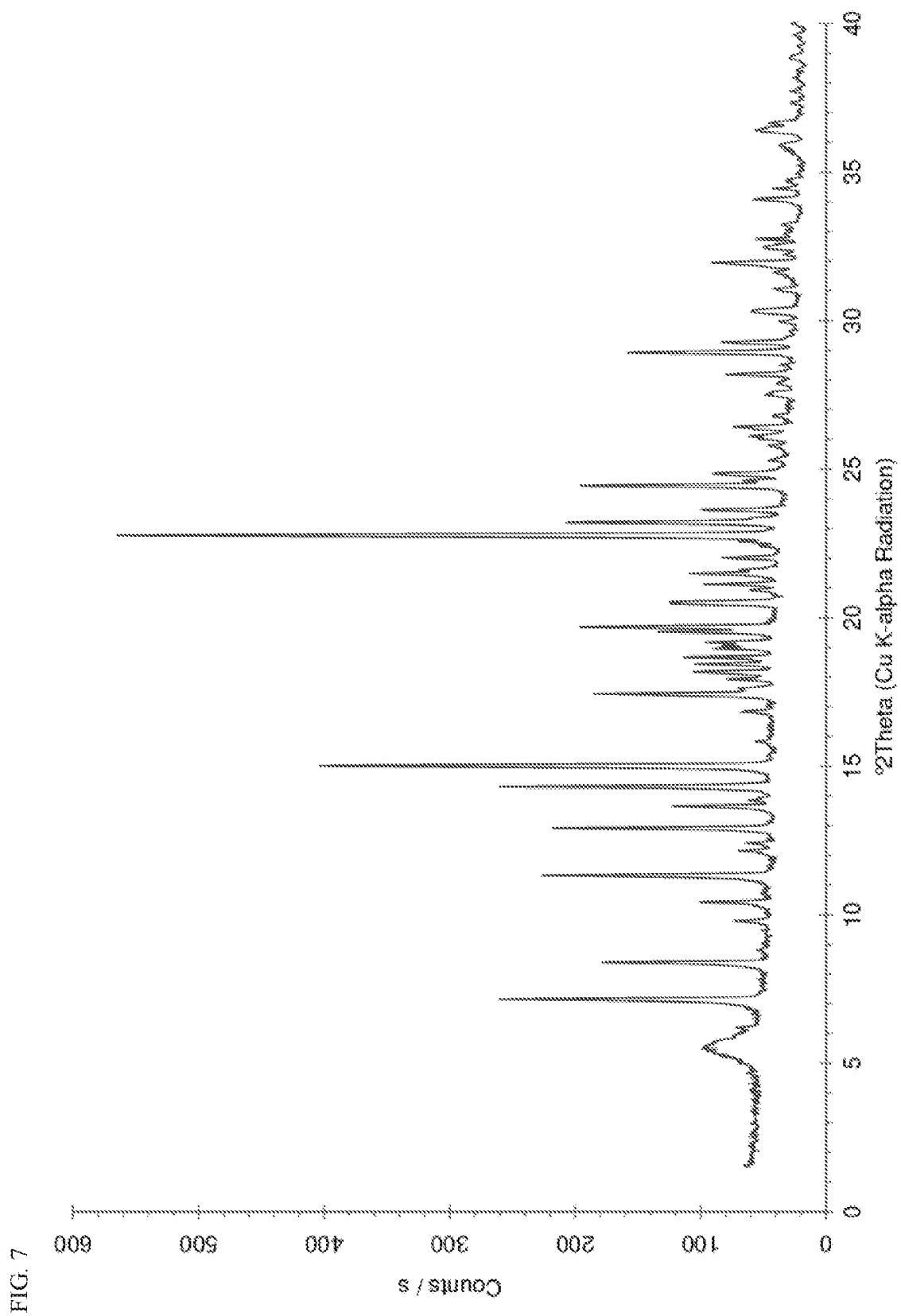
FIG. 7 is a PXRD pattern of a sample of Compound 1, Form G taken in transmission geometry between 0 °2θ and 40 °2θ.

FIG. 7 is a PXRD pattern of a sample of Compound 1, Form G taken in transmission mode. FIG. 7 was obtained using a Stoe Stadi P powder X-ray diffractometer using Cu Kα1 radiation and transmission geometry.

In some embodiments, morphic Form G can be characterized by the PXRD peaks set forth below in Table 8. For example, morphic Form G can be characterized by a PXRD peak at about 22.8 °2θ (Cu Kα1 radiation). Morphic Form G can further be characterized by PXRD peaks at about 7.1 °2θ, 11.3 °2θ, 12.9 °2θ, 14.3 °2θ, 15.0 °2θ, 23.2 °2θ, and/or 24.4 °2θ (Cu Kα1 radiation). Morphic Form G can further be characterized by PXRD peaks at about 8.4 °2θ, 13.7 °2θ, 17.4 °2θ, 19.5 °2θ, 19.7 °2θ, 20.5 °2θ, and/or 28.9 °2θ (Cu Kα1 radiation).

In some embodiments, morphic Form F can be characterized by PXRD peaks at about 7.1 °2θ, about 11.3 °2θ, and about 12.9 °2θ (±0.2 °2θ; ±0.1 °2θ; or ±0.0 °2θ; Cu Kα1 radiation). In some embodiments, morphic Form F can be characterized by PXRD peaks at about 11.3 °2θ, about 12.9 °2θ, and about 14.3 °2θ (±0.2 °2θ; ±0.1 °2θ; or ±0.0 °2θ; Cu Kα1 radiation). In some embodiments, morphic Form F can be characterized by PXRD peaks at about 12.9 °2θ, about 14.3 °2θ, and about 15.0 °2θ (±0.2 °2θ; ±0.1 °2θ; or ±0.0 °2θ; Cu Kα1 radiation). In some embodiments, morphic Form F can be characterized by PXRD peaks at about 14.3 °2θ, about 15.0 °2θ, and about 22.8 °2θ (±0.2 °2θ; ±0.1 °2θ; or ±0.0 °2θ; Cu Kα1 radiation). In some embodiments, morphic Form F can be characterized by PXRD peaks at about 15.0 °2θ, about 22.8 °2θ, and about 23.2 °2θ (±0.2 °2θ; ±0.1 °2θ; or ±0.0 °2θ; Cu Kα1 radiation). In some embodiments, morphic Form F can be characterized by PXRD peaks at about 22.8 °2θ, about 23.2 °2θ, and about 24.4 °2θ (±0.2 °2θ; ±0.1 °2θ; or ±0.0 °2θ; Cu Kα1 radiation).

In some embodiments, morphic Form G can be characterized by PXRD peaks at about 22.8 °2θ and about 7.1 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, and about 11.3 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 11.3 °2θ, and about 12.9 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 11.3 °2θ, 12.9 °2θ, and about 14.3 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 11.3 °2θ, about 12.9 °2θ, about 14.3 °2θ, and about 15.0 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 11.3 °2θ, about 12.9 °2θ, about 14.3 °2θ, about 15.0 °2θ, and about 23.2 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 11.3 °2θ, about 12.9 °2θ, about 14.3 °2θ, about 15.0 °2θ, about 23.2 °2θ, and about 24.4 °2θ (±0.2 °2θ; ±0.1 °2θ; or ±0.0 °2θ; Cu Kα1 radiation).

In some embodiments, morphic Form G can be characterized by PXRD peaks at about 22.8 °2θ, about 7.1 °2θ, about 8.4 °2θ, about 11.3 °2θ, about 12.9 °2θ, about 14.3 °2θ, about 15.0 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 19.5 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 19.5 °2θ, about 19.7 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 19.5 °2θ, about 19.7 °2θ, about 20.5 °2θ, about 23.2 °2θ, and about 24.4 °2θ (±0.2 °2θ; ±0.1 °2θ; or ±0.0 °2θ; Cu Kα1 radiation). In some embodiments, morphic Form G can be characterized by PXRD peaks at about 22.8 °2θ, about 7.1 °2θ, about 8.4 °2θ, about 11.3 °2θ, about 12.9 °2θ, about 13.7 °2θ, about 14.3 °2θ, about 15.0 °2θ, about 17.4 °2θ, about 19.5 °2θ, about 19.7 °2θ, about 20.5 °2θ, about 23.2 °2θ, about 24.4 °2θ, and about 28.9 °2θ (±0.2 °2θ; ±0.1 °2θ; or ±0.0 °2θ; Cu Kα1 radiation).

Accordingly, in some embodiments, morphic Form G is characterized by one, two, three, four, five, six, seven, eight, nine, ten, eleven, twelve, thirteen, or fourteen PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by one PXRD peak selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by two PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by three PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by four PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by five PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by six PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by seven PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by eight PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by nine PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by ten PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by eleven PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by twelve PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by thirteen PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation). In some embodiments, morphic Form G is characterized by fourteen PXRD peaks selected from about 7.1, 8.4, 11.3, 12.9, 13.7, 14.3, 15.0, 17.4, 19.5, 19.7, 20.5, 22.8, and 23.2 °2θ (Cu Kα1 radiation).

TABLE 8

Representative PXRD Peaks for Morphic Form G (Cu Kα1 radiation)

| Angle (°2θ) | d value (Å) | Intensity |
| --- | --- | --- |
| 7.1 | 12.37 | s |
| 8.4 | 10.52 | m |
| 8.8 | 10.03 | vw |
| 9.8 | 9.03 | w |
| 10.4 | 8.48 | w |
| 11.3 | 7.81 | s |
| 12.1 | 7.28 | w |
| 12.4 | 7.12 | vw |
| 12.9 | 6.85 | s |
| 13.7 | 6.48 | m |
| 13.9 | 6.38 | vw |
| 14.3 | 6.19 | s |
| 15.0 | 5.89 | s |
| 15.8 | 5.59 | vw |
| 16.8 | 5.27 | vw |
| 17.4 | 5.08 | m |
| 17.9 | 4.94 | w |
| 18.2 | 4.88 | w |
| 18.4 | 4.81 | w |
| 18.7 | 4.75 | w |
| 19.0 | 4.68 | w |
| 19.2 | 4.62 | w |
| 19.5 | 4.54 | m |
| 19.7 | 4.50 | m |
| 20.5 | 4.33 | m |
| 20.9 | 4.24 | vw |
| 21.1 | 4.20 | w |
| 21.5 | 4.13 | w |
| 22.0 | 4.03 | w |
| 22.8 | 3.90 | vs |
| 23.2 | 3.83 | s |
| 23.6 | 3.76 | w |
| 24.4 | 3.64 | s |
| 24.8 | 3.58 | w |
| 25.3 | 3.52 | vw |
| 25.8 | 3.45 | vw |
| 26.1 | 3.41 | w |
| 26.4 | 3.37 | w |
| 26.8 | 3.32 | vw |
| 27.5 | 3.24 | vw |
| 27.9 | 3.20 | vw |
| 28.2 | 3.16 | w |
| 28.9 | 3.08 | m |
| 29.3 | 3.05 | w |
| 30.0 | 2.98 | vw |
| 30.3 | 2.95 | w |
| 31.0 | 2.88 | vw |
| 31.9 | 2.80 | w |
| 32.5 | 2.76 | w |
| 32.8 | 2.73 | w |
| 33.2 | 2.69 | vw |
| 34.1 | 2.63 | w |
| 34.4 | 2.60 | vw |
| 34.7 | 2.58 | vw |
| 35.9 | 2.50 | vw |
| 36.4 | 2.47 | w |
| 36.7 | 2.45 | w |
| 37.3 | 2.41 | vw |
| 38.8 | 2.32 | vw |

Figure 14:
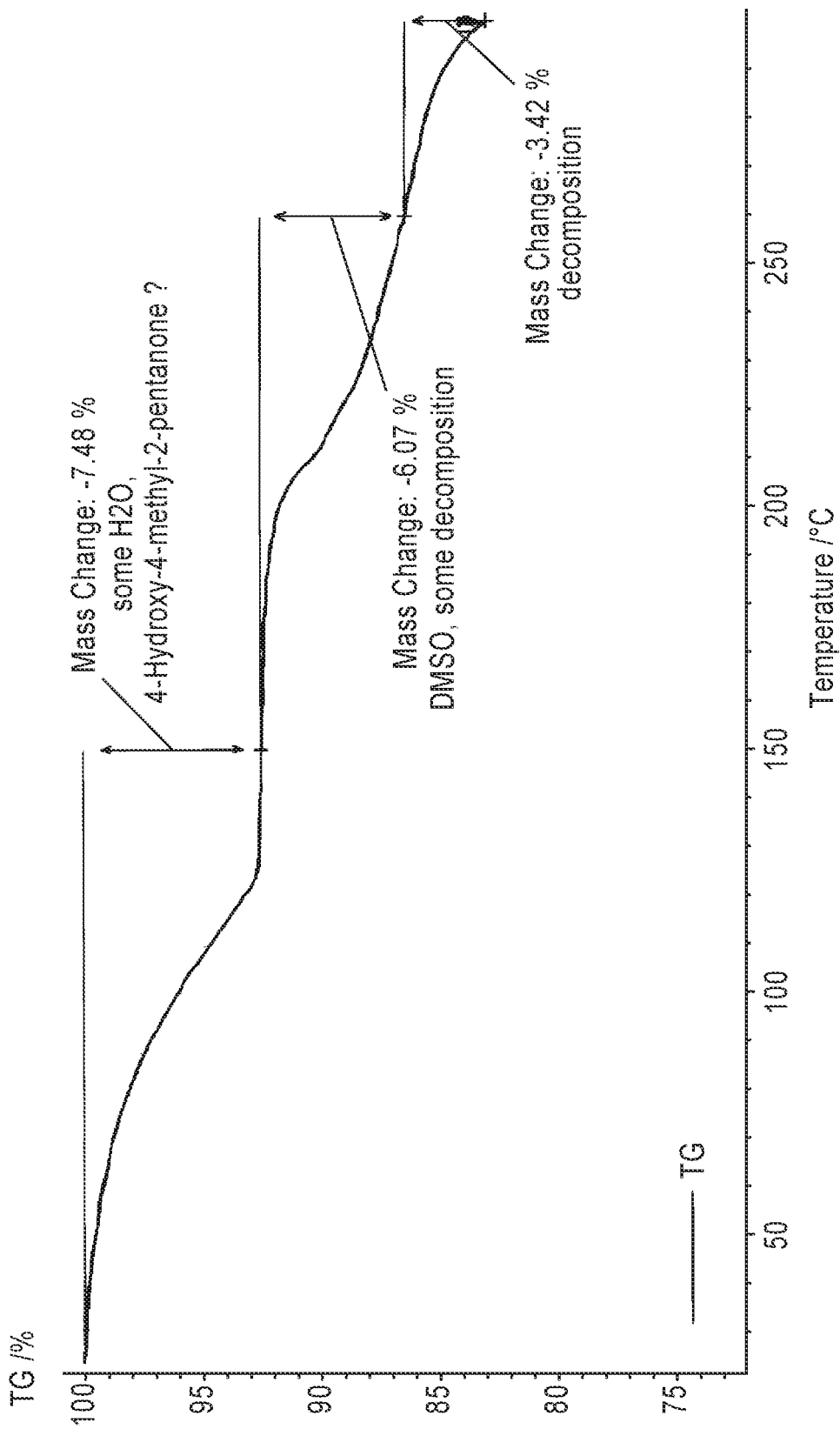
FIG. 14 is a TG-FTIR diagram of a sample of Compound 1, Form G.

FIG. 14 is a TG-FTIR diagram of a sample of Compound 1, Form G. FIG. 14 was obtained using a Netzsch TG 209, over the range of 25° C. to 300° C. The scanning speed was 10° C. per minute. As shown in FIG. 14, Form G exhibited a mass loss of about 7.5% (e.g., about 7.48%) between about 40° C. and about 150° C. Without wishing to be bound by theory, this mass loss is preliminarily proposed to be due to the loss of 4-hydroxy-4-methyl-2-pentanone. Form G also exhibited a mass loss of about 6.1% (e.g., about 6.07%) between about 150° C. and about 260° C. Without wishing to be bound by theory, this is proposed to be due to a loss of DMSO. Accordingly, in some embodiments, morphic Form G contains water and/or DMSO. Accordingly, in some embodiments, morphic Form G is characterized by a mass loss of about 7.5% between about 40° C. and about 150° C. (e.g., as measured by TG-FTIR). In some embodiments, morphic Form G is characterized by a mass loss of about 6.1% between about 150° C. and about 260° C. (e.g., as measured by TG-FTIR).

Methods of Use

Disease Indications

The present disclosure provides treatment of a viral infection with a compound and/or morphic form (e.g., Compound 1 Form A) disclosed herein and pharmaceutically acceptable salts thereof. The compounds and morphic forms encompassed by Formula I (e.g., Compound 1, Form A) can be used in treating, and/or in the manufacture of a medicament for treating at least one virus selected from but not limited to ssRNA viruses. In some embodiments, the virus can be a norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71), papilloma virus, West Nile virus, yellow fever virus, foot-and-mouth disease virus, Rift Valley fever virus, and other flavivirus, arenavirus, bunyavirus, alphavirus, and human immunodeficiency virus (HIV) infections, and any combination thereof. In some embodiments, the virus is a norovirus. In some embodiments, the method of treatment comprises administering to a subject in need thereof a therapeutically effective amount of a compound and/or morphic form (e.g., Compound 1 Form A) disclosed herein and pharmaceutically acceptable salts thereof.

In some embodiments, the present disclosure provides a method of treatment of Marburg virus infection or Marburg virus infection-associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments the present disclosure provides a method of treatment of Ebola virus infection or Ebola virus infection-associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments the present disclosure provides a method of treatment of influenza virus infection or influenza virus infection-associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments the present disclosure provides a method of treatment of norovirus virus infection or norovirus virus infection-associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments the present disclosure provides a method of treatment of picornaviridae virus infection or picornaviridae virus-infection associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments the present disclosure provides a method of treatment paramyxoviridae virus infection or paramyxoviridae virus infection-associated disease or disorder, by oral administration to a subject in need thereof a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In some embodiments of the present disclosure provides a method of treatment of enterovirus infection or enterovirus infection-associated disease or disorder, by oral administration to a subject in need thereof of a therapeutically effective dose of a compound of Formula I, (e.g., Compound 1, Form A) or a pharmaceutically acceptable salt thereof. In some embodiments, the therapeutically effective amount of a compound of Formula I (e.g., Compound 1, Form A) is administered as a pharmaceutical composition comprising a pharmaceutically acceptable carrier.

In one of the embodiments, a compound of Formula I, (e.g., Compound 1, Form A) can be used to treat norovirus. In another embodiments, a compound of Formula I, (e.g., Compound 1, Form A) can be used to treat norovirus associated with specific genotypes such as those in genogroups I, II and IV, VI and VII which are known to infect humans (Phan et al., J. Med. Virol. 2007 September; 79(9): 1388-1400).

In some embodiments the present disclosure provides a method of treatment of a viral infection, (e.g., norovirus virus infection or norovirus virus infection associated disease or disorder; influenza virus infection or influenza virus infection associated disease or disorder), by oral administration to a subject in need thereof a pharmaceutical composition of a therapeutically effective dose of a compound of Formula I, (e.g., Compound 1, Form A) or a pharmaceutically acceptable salt thereof.

The present disclosure provides prevention and/or prophylaxis of a viral infection with a compound and/or morphic form (e.g., Compound 1 Form A) disclosed herein and pharmaceutically acceptable salts thereof. The compounds and morphic forms encompassed by Formula I (e.g., Compound 1, Form A) can be used in prevention and/or prophylaxis; and/or in the manufacture of a medicament for prevention and/or prophylaxis at least one virus selected from but not limited to ssRNA viruses. In some embodiments, the virus can be a norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71, papilloma virus, West Nile virus, yellow fever virus, foot-and-mouth disease virus, Rift Valley fever virus, and other flavivirus, arenavirus, bunyavirus, alphavirus, and human immunodeficiency virus (HIV) infections, and any combination thereof. In some embodiments, the virus is a norovirus. In some embodiments, the method of prevention and/or prophylaxis comprises administering to a subject in need thereof a prophylactically effective amount of a compound and/or morphic form (e.g., Compound 1 Form A) disclosed herein and pharmaceutically acceptable salts thereof.

In some embodiments, the present disclosure provides a method of prevention and/or prophylaxis of Marburg virus infection or Marburg virus infection-associated disease or disorder, by oral administration to a subject in need thereof a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of Marburg virus infection or Marburg virus infection-associated disease or disorder can comprises delaying the onset of Marburg virus infection or Marburg virus infection-associated disease or disorder.

In some embodiments the present disclosure provides a method of prevention and/or prophylaxis of Ebola virus infection or Ebola virus infection-associated disease or disorder, by oral administration to a subject in need thereof a pharmaceutical composition of a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of Ebola virus infection or Ebola virus infection-associated disease or disorder can comprises delaying the onset of Ebola virus infection or Ebola virus infection-associated disease or disorder.

In some embodiments the present disclosure provides a method of prevention and/or prophylaxis of influenza virus infection or influenza virus infection-associated disease or disorder, by oral administration to a subject in need thereof a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of influenza virus infection or influenza virus infection-associated disease or disorder can comprises delaying the onset of influenza virus infection or influenza virus infection-associated disease or disorder.

In some embodiments the present disclosure provides a method of prevention and/or prophylaxis of norovirus virus infection or norovirus virus infection-associated disease or disorder, by oral administration to a subject in need thereof a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of norovirus virus infection or norovirus virus infection-associated disease or disorder can comprises delaying the onset of norovirus virus infection or norovirus virus infection-associated disease or disorder.

In some embodiments the present disclosure provides a method of prevention and/or prophylaxis of picornaviridae virus infection or picornaviridae virus-infection associated disease or disorder, by oral administration to a subject in need thereof a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of picornaviridae virus infection or picornaviridae virus infection-associated disease or disorder can comprises delaying the onset of picornaviridae virus infection or picornaviridae virus infection-associated disease or disorder.

In some embodiments the present disclosure provides a method of prevention and/or prophylaxis paramyxoviridae virus infection or paramyxoviridae virus infection-associated disease or disorder, by oral administration to a subject in need thereof a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of paramyxoviridae virus infection or paramyxoviridae virus infection-associated disease or disorder can comprises delaying the onset of paramyxoviridae virus infection or paramyxoviridae virus infection-associated disease or disorder.

In some embodiments of the present disclosure provides a method of prevention and/or prophylaxis of enterovirus infection or enterovirus infection-associated disease or disorder, by oral administration to a subject in need thereof of a prophylactically effective dose of a compound of Formula I, (e.g., Compound 1, Form A) or a pharmaceutically acceptable salt thereof. In some embodiments, the prophylactically effective amount of a compound of Formula I (e.g., Compound 1, Form A) is administered as a pharmaceutical composition comprising a pharmaceutically acceptable carrier. In some embodiments, prevention and/or prophylaxis of enterovirus virus infection or enterovirus virus infection-associated disease or disorder can comprises delaying the onset of enterovirus virus infection or enterovirus virus infection-associated disease or disorder.

In one of the embodiments, a compound of Formula I, (e.g., Compound 1, Form A) can be used to prevent transmission of norovirus. In another embodiments, a compound of Formula I, (e.g., Compound 1, Form A) can be used to prevent transmission of a norovirus associated with specific genotypes such as those in genogroups I, II and IV, VI and VII which are known to infect humans (Phan et al., J. Med. Virol. 2007 September; 79(9): 1388-1400).

In some embodiments the present disclosure provides a method of prevention and/or prophylaxis of a viral infection, (e.g., norovirus virus infection or norovirus virus infection associated disease or disorder; influenza virus infection or influenza virus infection associated disease or disorder), by oral administration to a subject in need thereof a pharmaceutical composition of a prophylactically effective dose of a compound of Formula I, (e.g., Compound 1, Form A) or a pharmaceutically acceptable salt thereof.

In some embodiments the present disclosure provides a method of prevention or delaying onset of a viral infection, (e.g., norovirus virus infection or norovirus virus infection associated disease or disorder; influenza virus infection or influenza virus infection associated disease or disorder), by oral administration to a subject in need thereof a pharmaceutical composition of a prophylactically effective dose of a compound of Formula I, (e.g., Compound 1, Form A) or a pharmaceutically acceptable salt thereof. In some embodiments, the administration of a compound of Formula I (e.g., Compound 1 Form A) can prevent transmission of an infection such as a viral infection. For example, Compound 1 can be administered to a subject who has not yet been infected with an infection (e.g., a viral infection such as norovirus) but who is at risk of developing an infection as a result of being in close proximity to others who are infected with the viral infection. As noted above, such situations can arise in, for instance, hospitals, cruise ships, college campuses, the Olympic Village, airplanes, airports and the like. As set forth herein, administration of a compound of Formula I to a subject prior to the subject being infected can prevent transmission of a viral infection to the subject despite the subject being in close proximity to others with the infection and thus being at higher risk for infection.

The present disclosure further provides a method of prevention and/or prophylaxis of norovirus infection or a norovirus infection associated disease or disorder, by orally administering to a subject a prophylactically effective dose of a compound of Formula I, (e.g., Compound 1, Form A) or a pharmaceutically acceptable salt thereof, in combination with one or more antiviral agent. In some embodiments, the prophylactically effective amount of a compound of Formula I (e.g., Compound 1, Form A) is administered as a pharmaceutical composition comprising a pharmaceutically acceptable carrier.

In some embodiments, the method of prevention and/or prophylaxis comprises administering a subject with a compound of the disclosure prior to infection with the norovirus. As noted above, a compound of Formula I can be administered to a subject that is at risk for developing a norovirus infection, for example a person who spends time in close proximity to someone infected with norovirus. For instance, one may be at risk of being infected with norovirus if one is a hospital worker or hospital patient in the presence of another patient that is infected with norovirus. Norovirus can also spread in other contexts such as college campuses, cruise ships, airplanes, the Olympic Village, and the like.

Dosage Regimens

The regimen of administration can affect what constitutes a therapeutically and/or prophylactically effective amount. A compound of Formula I, (e.g., Compound 1, Form A) or a pharmaceutically acceptable salt thereof can be administered to the subject either prior to or after the onset of a disease. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation. Further, the dosages can be co-administered in combination with other antiviral.

The dosage regimen utilizing a therapeutically and/or prophylactically amount of a compound of the present disclosure (e.g., Compound 1, Form A) can also be selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the therapeutically and/or prophylactically effective amount of the drug required to prevent, counter or arrest the progress of the condition.

In some embodiments, the subject treated for a viral infection (e.g., a norovirus infection or a norovirus infection associated disease or disorder) is administered once or twice a week with about 40 mg, 50 mg, 75 mg, 100 mg, 150 mg, 175 mg, 200 mg, or 250 mg of a compound of Formula I, (e.g., Compound 1, Form A) or a pharmaceutically acceptable salt thereof. The present disclosure provides treatment of a subject for norovirus infection or norovirus infection associated disease or disorder by administering to the subject once a week (QW) about 200 mg or twice a week (BIW) about 100 mg of a compound of Formula I, (e.g., Compound 1, Form A) or a pharmaceutically acceptable salt thereof. In one embodiment, the subject is treated twice a week (BIW) with about 100 mg of the compound. In another embodiment, the subject is treated once a week (QW) with about 200 mg, or twice a week (BIW) with about 100 mg of the compound.

In some embodiments a compound of Formula I, (e.g., Compound 1, Form A) or a pharmaceutically acceptable salt thereof is administered to the subject for prophylaxis and/or prevention of a viral infection (e.g., a norovirus infection or a norovirus infection associated disease or disorder) once or twice a week with about 40 mg, 50 mg, 75 mg, 100 mg, 150 mg, 175 mg, 200 mg, or 250 mg of a compound of Formula I, (e.g., Compound 1, Form A) or a pharmaceutically acceptable salt thereof. The present disclosure provides prophylaxis and/or prevention of a norovirus infection or norovirus infection associated disease or disorder in a subject by administering to the subject once a week (QW) about 200 mg or twice a week (BIW) about 100 mg of a compound of Formula I, (e.g., Compound 1, Form A) or a pharmaceutically acceptable salt thereof. In one embodiment, the subject is administered twice a week (BIW) with about 100 mg of the compound. In another embodiment, the subject is administered once a week (QW) with about 200 mg, or twice a week (BIW) with about 100 mg of the compound for the prevention of an infection.

In an embodiment, a compound of Formula I, (e.g., Compound 1, Form A) or pharmaceutically acceptable salt thereof having a purity of equal to or greater than about 91% (e.g., greater than 92%, greater than 93%, greater than 94%, greater than 95%, greater than 96%, greater than 97%, greater than 98%, or greater than 99%) is administered orally to a subject, for example, at a dosage of about 0.01 mg/kg to about 10 mg/kg or more, e.g., up to 100 mg/kg, or up to 400 mg/kg, or up to 1000 mg/kg for a therapeutic and/or prophylactic effect.

In another embodiment, a compound of Formula I, (e.g., Compound 1, Form A) or pharmaceutically acceptable salt thereof having a purity of equal to or greater than about 91% w/w (e.g., greater than about 99% w/w) is administered to a subject at a dosage of about 0.01 mg/kg, 0.05 mg/kg, 0.1 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg or more or any range therein for a therapeutic and/or prophylactic effect.

Dosage and administration are adjusted to provide sufficient levels of the active agent(s) or to maintain the desired (e.g., therapeutic and/or prophylactic) effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, once every two weeks, or monthly depending on half-life and clearance rate of the particular formulation.

In some embodiments, the administration of a compound of Formula I (e.g., Compound 1 Form A) for the treatment and/or prevention of a disease continues for ten total doses. For instance, a compound of Formula I, (e.g., Compound 1, Form A) can be administered at dosages of about 100 mg twice a week for five weeks (i.e., ten total doses). Alternatively, a compound of Formula I (e.g., Compound 1, Form A) can be administered with a loading dose of about 200 mg followed by about 100 mg doses continuing twice a week. In some embodiments, the administration continues for ten total doses. For instance, a compound of Formula I, (e.g., Compound 1, Form A) can be administered at a loading dose of about 200 mg followed by nine additional about 100 mg doses twice a week for a total of ten doses. In one of the embodiments, a compound of Formula I, (e.g., Compound 1, Form A) can be dosed daily in the range of about 20-200 mg/day or weekly in the range of about 200 mg-3000 mg.

In one or more embodiments a compound of the disclosure can be useful at treating and/or preventing a viral infection such as a norovirus infection or a norovirus-infection associated disease or disorder. In some embodiments, treatment of the infection, e.g., norovirus infection, can comprise daily dosing, or dosing multiple times per day. In some embodiments, the total treatment regimen only lasts as long as the norovirus infection is active (e.g., between 1-3 days). In some embodiments, a compound of the disclosure can be dosed multiple times per day for 1-3 days to treat a norovirus infection.

In another embodiment, tablets or suspensions comprising a compound of Formula I, (e.g., Compound 1, Form A) or a pharmaceutically acceptable salt thereof can be administered at, for instance, a dose of about 40-3000 mg daily. For instance, a compound of Formula I can be administered BID, TID, QID (i.e., 4 times a day), q6h, q8h, q12h, once a week (QW) or twice a week (BIW). In another embodiment, tablets or suspensions of a compound of Formula I, (e.g., Compound 1, Form A) or a pharmaceutically acceptable salt thereof can be administered at a dose of about 40-400 mg daily, BID, TID, QID (i.e., 4 times a day), q6h, q8h, q12h, once a week (QW) or twice a week (BIW) for a therapeutic and/or prophylactic effect.

In therapeutic and/or prophylactic applications, the dosages of the pharmaceutical compositions disclosed herein vary depending on the agent, the age, weight, and clinical condition of the recipient patient, and the experience and judgment of the clinician or practitioner administering the therapy, among other factors affecting the selected dosage. Dosages can range from about 0.01 mg/kg to about 100 mg/kg. In preferred aspects, dosages can range from about 0.1 mg/kg to about 10 mg/kg. In an aspect, the dose will be in the range of about 1 mg to about 1 g; about 10 mg to about 500 mg; about 20 mg to about 400 mg; about 40 mg to about 400 mg; or about 50 mg to about 400 mg, in single, divided, or continuous doses (which dose can be adjusted for the patient's weight in kg, body surface area in $m^2$, and age in years). In certain embodiments, the amount per dosage form can be about 0.1 mg to about 3000 mg, e.g., about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg, about 600 mg, about 700 mg, about 800 mg, about 900 mg, about 1000 mg, about 1250 mg, 1500 mg, about 1750 mg, about 2000 mg, about 2500 mg, or about 3000 mg. In one embodiment, the amount can be about 20 mg. In one embodiment, the amount can be about 50 mg. In another embodiment the dosage can be 100 mg. In another embodiment the dose can be 500 mg.

In another embodiment, a compound of Formula I, (e.g., Compound 1, Form A) or pharmaceutically acceptable salts thereof can be administered to a subject as a single dose for a therapeutic and/or prophylactic effect. In another embodiment, a compound of Formula I, (e.g., Compound 1, Form A) or pharmaceutically acceptable salts thereof can be administered to a subject in multiple doses. Multiple doses can be administered regularly, for example, once every 12 hours, once a day, every 2 days, every 3 days, every 4 days, every 5 days, every 6 days, every 7 days, every 8 days, every 9 days, every 10 days, every 11 days, every 12 days, every 13 days, every 14 days or every 15 days. For example, doses can be administered twice per week. Moreover, each individual dose can be administered with the same or a different dosage.

For example, a subject can be administered a compound of Formula I, (e.g., Compound 1, Form A) or a pharmaceutically acceptable salt thereof with a first dose of about 1-20 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, about 3.9-4.0 mg/kg, about 4.0-5.0 mg/kg, about 5.0-6.0 mg/kg, about 6.0-7.0 mg/kg, about 7.0-8.0 mg/kg, about 8.0-9.0 mg/kg, about 9.0-10.0 mg/kg, or about 10-20 mg/kg) of a compound of Formula I, (e.g., Compound 1, Form A) (or a pharmaceutically acceptable salt thereof) followed by one or more additional doses at 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of a compound of Formula I, (e.g., Compound 1, Form A) (or a pharmaceutically acceptable salt thereof) in the same week or in the following week for a therapeutic and/or prophylactic effect. For example, a subject can be administered with a first dose of about 3 mg/kg followed by one or more additional doses at about 1 mg/kg. For example, a subject can be administered with a first dose of about 2 mg/kg followed by one or more additional doses at about 3 mg/kg. For example, a subject can be administered with a first dose of 4 mg/kg followed by one or more additional doses at about 4 mg/kg.

Multiple doses can also be administered at variable time intervals for a therapeutic and/or prophylactic effect. For example, the first 2, 3, 4, 5, 6, 7, or 8 or more doses can be administered at an interval of 6 days followed by additional doses administered at an interval of 7 days. For example, the first 2, 3, 4, 5, 6, 7, or 8 or more doses can be administered at an interval of 7 days followed by additional doses administered at an interval of 3 days.

In one embodiment, a compound of Formula I, (e.g., Compound 1, Form A) or a pharmaceutically acceptable salt thereof can be administered to a subject once a week at a dose of about 40-3000 mg, or twice a week at a dose of about 40-3000 mg for a therapeutic and/or prophylactic effect.

In some embodiments, a compound of the present disclosure (e.g., Compound 1 Form A) is administered daily, BID, TID, once a week (QW), or twice a week (BIW) with about 40-3000 mg of a compound of Formula I, (e.g., Compound 1, Form A) or a pharmaceutically acceptable salt thereof for a therapeutic and/or prophylactic effect. A pharmaceutical compositions of the present disclosure can be administered daily, BID, TID, once a week (QW), or twice a week (BIW) with about 40 mg, 50 mg, 75 mg, 100 mg, 150 mg, 175 mg, 200 mg, 250 mg, 275 mg, 300 mg, 325 mg, 350 mg, 375 mg, 400 mg, 450 mg, 500 mg, 500-600 mg, 600-700 mg, 700-800 mg, 800-900 mg, or 900-1000 mg, or twice a week (BIW) with about 40 mg, 50 mg, 75 mg, 100 mg, 150 mg, 175 mg, 200 mg, 250 mg, 275 mg, 300 mg, 325 mg, 350 mg, 375 mg, or 400 mg, 450 mg, 500 mg, 500-600 mg, 600-700 mg, 700-800 mg, 800-900 mg, or 900-1000 mg of a compound of Formula I, (e.g., Compound 1, Form A) or a pharmaceutically acceptable salt thereof.

The present disclosure provides a compound of Formula I, (e.g., Compound 1, Form A) administered at a dose of about 1-100 mg/kg (e.g., 10-20 mg/kg, 20-50 mg/kg, 50-75 mg/kg, 75-100 mg/kg) for a therapeutic and/or prophylactic effect.

Routes of Administration

A compound (e.g., Compound 1 Form A) of the present disclosure, or a pharmaceutically acceptable salt, ester or derivative thereof, can be administered orally, nasally, intranasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

For administration by inhalation, a compound of the disclosure can be delivered in the form of an aerosol spray from pressured container or dispenser, which can contain a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of, e.g., nasal sprays, rectal foam, or suppositories. For transdermal administration, an active compound can be formulated into an ointment, salve, gel, or cream as generally known in the art.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Combination Therapy

The present disclosure provides methods of preventing or treating a viral infection in a subject (e.g., a norovirus infection). The methods comprise administering a subject a therapeutically and/or prophylactically effective amount of a compound (e.g., Compound 1, Form A) described herein. A compound can be used in a monotherapy or combination therapy regime.

As used herein, "monotherapy" means or refers to the administration of a single active or therapeutic compound (e.g., Compound 1, Form A) to a subject in need thereof. Preferably, monotherapy will involve administration of a therapeutically and/or prophylactically effective amount of an active compound. For example, norovirus monotherapy with one of the compound of the present disclosure, or a pharmaceutically acceptable salt, prodrug, metabolite, analog or derivative thereof, to a subject in need of treatment of norovirus. Monotherapy can be contrasted with combination therapy, in which a combination of multiple active compounds is administered, preferably with each component of the combination present in a therapeutically and/or prophylactically effective amount. In one aspect, monotherapy with a compound of the present disclosure, or a pharmaceutically acceptable salt, prodrug, metabolite, polymorph or solvate thereof, is more effective than combination therapy in inducing a desired biological effect.

As used herein, "combination therapy" or "co-therapy" includes the administration of a compound of the present disclosure, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" can be, but generally is not, intended to encompass the administration of two or more of these therapeutic agents as part of separate monotherapy regimens that incidentally and arbitrarily result in the combinations of the present disclosure.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected can be administered by intravenous injection while the other therapeutic agents of the combination can be administered orally. Alternatively, for example, all therapeutic agents can be administered orally or all therapeutic agents can be administered by intravenous injection. The sequence in which the therapeutic agents are administered is not narrowly critical.

In some embodiments, combination therapy embraces the administration of a compound and/or morphic form of the present disclosure (e.g., Compound 1, Form A) in temporal proximity with another therapeutic agent. As used herein, "temporal proximity" means that administration of one therapeutic agent (e.g., Compound 1 Form A) occurs within a time period before or after the administration of another therapeutic agent, such that the therapeutic effect of the one therapeutic agent overlaps with the therapeutic effect of the another therapeutic agent. In some embodiments, the therapeutic and/or prophylactic effect of the one therapeutic agent completely overlaps with the therapeutic and/or prophylactic effect of the another therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" can vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity can change during a treatment cycle or within a dosing regimen.

"Combination therapy" also embraces the administration of the therapeutic and/or prophylactic agents as described above in further combination with other biologically active ingredients and non-drug therapies. Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In some embodiments the present disclosure provides a method of treatment, prevention, or delaying on-set of a viral infection, (e.g., norovirus virus infection or norovirus virus infection associated disease or disorder; influenza virus infection or influenza virus infection associated disease or disorder), by oral administration to a subject in need thereof a compound of Formula I, for instance a pharmaceutical composition of a therapeutically effective dose of a compound of Formula I, (e.g., Compound 1, Form A) or a pharmaceutically acceptable salt thereof in combination with one or more antiviral agents.

In some embodiments the present disclosure provides a method of treatment, prevention, or delaying on-set of picornaviridae virus infection or picornaviridae virus infection associated disease or disorder, by oral administration to a subject in need thereof a pharmaceutical composition of a therapeutically effective dose of a compound of Formula I, (e.g., Compound 1, Form A) or a pharmaceutically acceptable salt thereof in combination with one or more antiviral agents.

In some embodiments the present disclosure provides a method of treatment, prevention, or delaying on-set of paramyxoviridae virus infection or paramyxoviridae virus infection associated disease or disorder, by oral administration to a subject in need thereof a pharmaceutical composition of a therapeutically effective dose of a compound of Formula I, (e.g., Compound 1, Form A) or a pharmaceutically acceptable salt thereof in combination with one or more antiviral agents.

In one embodiment, the method of treating, prevention and/or prophylaxis of a viral infection, e.g., influenza virus or norovirus infection or norovirus infection further comprises administering at least one additional antiviral agent. In one embodiment, the one additional antiviral agent is an adamantane. In a further embodiment, the one additional antiviral agent is amantadine or rimantadine. In another embodiment, the one additional antiviral agent is a neuraminidase inhibitor (e.g., oseltamivir, zanamivir, laninamivir, and peramivir). In a further embodiment, the one additional antiviral agent is oseltamivir or zanamivir.

In some embodiments, the pharmaceutical composition of the present disclosure (e.g., Compound 1, Form A) is administered in combination with one or more compounds or compositions selected from midazolam, cyclosporine A, tacrolimus, ganciclovir, valganciclovir, foscavir, cidofovir, second-line anti-CMV drugs, second-line anti-HCV drugs, foscarnet, filgrastim, pegfilgrastim, corticosteroids such as budesonide, beclomethasone, and broad-spectrum CYP inhibitor aminobenzotriazole or combinations thereof.

In additional embodiments, the compound is for administration in combination with at least one other immunosuppressant agent. In one embodiment, the immunosuppressant agent is concurrently or sequentially administered. The immunosuppressant agents include but are not limited to Daclizumab, Basiliximab, Tacrolimus, Sirolimus, Mycophenolate, Cyclosporine A, Glucocorticoids, Anti-CD3 monoclonal antibodies, Antithymocyte globulin, Anti-CD52 monoclonal antibodies, Azathioprine, Everolimus, Dactinomycin, Cyclophosphamide, Platinum, Nitrosurea, Methotrexate, Mercaptopurine, Muromonab, IFN gamma, Infliximab, Etanercept, Adalimumab, Natalizumab, Fingolimod, and combinations thereof.

A compound or composition provided herein can also be used in combination with an enhancer agent, with other active ingredients, or with an immunosuppressant agent. In certain embodiments, a compound can be administered in combination, or sequentially, with another therapeutic agent or an enhancer. Such other therapeutic agents include those known for treatment, prevention, or amelioration of one or more symptoms associated with viral infections. It should be understood that any suitable combination of a compound provided herein with one or more of the above-mentioned therapeutic agent or enhancer and optionally one or more further pharmacologically active substances are considered to be within the scope of the present disclosure. In another embodiment, a compound provided herein is administered prior to or subsequent to the one or more additional active ingredients. In one embodiment, two or more of the antiviral agents disclosed herein are administered serially or in combination. The amount of some enhancers can be selected using methods known in the art to enhance the bioavailability of the anti-viral agent. Any amount can be used that provides a desired response by some enhancers. The dosages can range, in a non-limiting example, from 0.001 mg to about 3000 mg of compound per kilogram of body weight per day, e.g., 0.01 to 500 mg/kg, or e.g., 0.1-20 mg/kg.

The pharmacokinetic behavior of a composition will vary somewhat from subject to subject within a population. The numbers described above for the compositions disclosed herein are based on the average behavior in a population. The present disclosure is intended to encompass compositions that on average fall within the disclosed ranges, even though it is understood that certain subjects can fall outside of the ranges.

The pharmaceutical compositions can be included in a container, pack, or dispenser together with instructions for administration. The present disclosure provides a kit including, in addition to a pharmaceutical composition of a compound of the disclosure, a container, pack, or dispenser together with instructions for administration.

A compound of the present disclosure (e.g., Compound 1, Form A), or a pharmaceutically acceptable salt, prodrug, metabolite, analog or derivative thereof, can be administered in combination with a second antiviral compound. For example, as noted above, a composition of the present disclosure can include a compound as described above in combination with one or more (e.g., 1, 2, 3) additional active agents such as described in this section in analogous manner as known in the art. Additional antiviral active agents that can be used with a compound of the present disclosure in carrying out the present methods include, but are not limited to, those that target the M2 ion channel in influenza A viruses (e.g., the adamantanes, such as amantadine and rimantadine); those that inhibit viral uncoating following entry into the cell, agents that block release of the newly formed virions from the surface of infected cells (e.g., the neuraminidase inhibitors, such as oseltamivir and zanamivir).

Methods for Preventing Disease or Disorder Due to Virus Reactivation

The current disclosure also provides a method of preventing a disease or disorder in a subject at risk of virus infection reactivation, by orally administering to the subject a pharmaceutical composition of a therapeutically effective dose of a compound of Formula I, (e.g., Compound 1, Form A) or a pharmaceutically acceptable salt thereof. As used herein, "viral reactivation" is understood as a process by which a latent virus switches to a lytic phase of replication.

In some embodiments, the virus at risk of reactivation can be herpes simplex virus, varicella zoster virus, human cytomegalovirus, human herpesvirus 6, human herpesvirus 7, Kaposi's sarcoma-associated herpesvirus, JC virus, BK virus, parvovirus, adenovirus, influenza, norovirus, EBV, ebola, picornaviridae, paramyxoviridae, and Marburg virus. In some embodiments, the virus at risk of reactivation can be influenza. In one embodiment, the subject at risk of virus infection reactivation may be a subject with a weakened immune system such as a stem cell transplant or renal transplant recipient. In an embodiment, the subject may be a post-hematopoietic stem cell transplant subject. In yet other embodiments, the subject may be an islet cell transplant recipient, bone marrow transplant recipient, endothelial cell transplant recipient, epidermal cell transplant recipient, myoblast transplant recipient, muscle derived stem cell recipient, and/or neural stem cell transplant recipient.

Accordingly, administration (e.g., oral administration) of a prophylactically effective amount of a compound of Formula I (e.g., Compound 1 Form A) to a subject with a latent viral infection can prevent or delay onset of viral reactivation in a subject that is at risk of viral reactivation.

Effect of Food

In some embodiments, the pharmaceutical composition of the current embodiments, e.g., tablet or suspension, can be provided to a subject when the subject is either fasted or in fed conditions. In one embodiment, the composition comprising a compound of Formula I, (e.g., Compound 1, Form A) (or a pharmaceutically acceptable salt thereof) can be provided to a subject having an empty stomach, e.g., after fasting for less than 24 hours but more than 12 hours, more than 11 hours, more than 10 hours, more than 8 hours, or more than 5 hours.

In other embodiments, the composition comprising a compound of Formula I, (e.g., Compound 1, Form A) (or a pharmaceutically acceptable salt thereof) can be provided to a subject in combination with food or subsequent to having food. In one embodiment, a compound of Formula I, (e.g., Compound 1, Form A) (or a pharmaceutically acceptable salt thereof) can be taken by a subject on an empty stomach.

Patient Population

In certain embodiments, a therapeutically and/or prophylactically effective amount of a compound of Formula I, (e.g., Compound 1, Form A) (or a pharmaceutically acceptable salt thereof), a composition comprising a compound of Formula I, (e.g., Compound 1, Form A), or a combination therapy comprising a composition of Formula I, (e.g., Compound 1, Form A) is administered to a mammal in need thereof (e.g., a human) which is about 1 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old, or 95 to 100 years old. In some embodiments, the mammal is suffering from a viral infection (e.g., an ssRNA infection such as a norovirus infection).

In certain embodiments, a prophylactically effective amount of a compound of Formula I, (e.g., Compound 1, Form A), a composition comprising a compound of Formula I, (e.g., Compound 1, Form A) or a combination therapy comprising a compound of Formula I, (e.g., Compound 1, Form A) is administered to a human at risk for developing a virus infection. In certain embodiments, a compound of Formula I, (e.g., Compound 1, Form A) a composition comprising a compound of Formula I, (e.g., Compound 1, Form A) or a combination therapy comprising a compound of Formula I, (e.g., Compound 1, Form A) is administered to a human with a virus infection. In certain embodiments, the patient is a human about 1 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In some embodiments, a therapeutically and/or prophylactically effective amount of a compound of Formula I, (e.g., Compound 1, Form A), a composition comprising a compound of Formula I, (e.g., Compound 1, Form A), or a combination therapy comprising a compound of Formula I, (e.g., Compound 1, Form A) is administered to a human infant. In other embodiments, a therapeutically and/or prophylactically effective amount of a compound of Formula I, (e.g., Compound 1, Form A), or a combination therapy comprising a compound of Formula I, (e.g., Compound 1, Form A) is administered to a human child. In other embodiments, a therapeutically and/or prophylactically effective amount of a compound of Formula I, (e.g., Compound 1, Form A), a composition comprising a compound of Formula I, (e.g., Compound 1, Form A), or a combination therapy comprising a compound of Formula I, (e.g., Compound 1, Form A) is administered to a human adult. In yet other embodiments, a therapeutically and/or prophylactically effective amount of a compound of Formula I, (e.g., Compound 1, Form A), a composition comprising a compound of Formula I, (e.g., Compound 1, Form A), or a combination therapy comprising a compound of Formula I, (e.g., Compound 1, Form A) is administered to an elderly human.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort can be had to various other embodiments, modifications, and equivalents thereof which can suggest themselves to those skilled in the art without departing from the spirit of the present disclosure and/or scope of the appended claims.

ABBREVIATIONS $a_{H2O}$ Water activity
aq. Aqueous
DMA N,N-Dimethylacetamide
DMF N,N-Dimethylformamide
DMSO Dimethylsulfoxide
DSC Differential scanning calorimetry
HPLC High pressure liquid chromatography
ICH International Conference on Harmonization
MeOH Methanol
MSZW Metastable zone width
NMR Nuclear magnetic resonance
1-PrOH 1-propanol
PXRD Powder X-ray diffraction
RH/r.h. Relative humidity
RT r.t. Room temperature (22-26° C.)
S Approximate solubility
SC-XRD Single crystal X-ray diffraction
SEQ Suspension equilibration experiment
Start. Mat. Starting material
$T_{clear}$ Temperature at which a clear solution is obtained during heating
$T_{cloud}$ Temperature at which a solution starts to crystallize during cooling
Temp. Temperature
THF Tetrahydrofuran
TG-FTIR Thermogravimetry coupled to Fourier transform infrared spectroscopy.
Experimental Procedures Unless otherwise specified, the procedures used herein are as set forth below.
Powder X-ray Diffraction (PXRD)

When characterizing peaks (e.g., in the peak tables above), intensities are given qualitatively: vw=very weak, w=weak, m=medium, s=strong, vs=very strong. Unless otherwise specified, all PXRD peaks and patterns are given in ° 2θ using Cu Kα radiation at a wavelength of 1.5406 Å.
Reflection Mode Measurements carried out with a Bruker D8 Advance powder X-ray diffractometer used Cu Kα radiation in the Bragg-Brentano reflection geometry. Generally, the 2θ values are accurate within 0.1-0.2°. The relative peak intensities can vary considerably for different samples of the same crystalline form because of different preferred orientations of the crystals. The samples were prepared without any special treatment other than the application of slight pressure to achieve a flat surface. Silicon single crystal sample holders of 0.1 mm, 0.5 mm or 1.0 mm depth were used. The tube voltage and current were 40 kV and 40 mA, respectively. The X-ray diffractometer is equipped with a LynxEye detector. A variable divergence slit was used with a 30 window. The samples were rotated at 0.5 rps during the measurement. PXRD standard measurements were carried out in the 2θ range 2° to 50° with a total measuring time of about 10 minutes. The step size was 0.02 °2θ with a step time of 37 seconds.

Transmission Mode

The Stoe Stadi P diffractometer was equipped with a Mythen1K Detector; Cu—$K_{\alpha 1}$ radiation; standard measurement conditions: transmission; 40 kV and 40 mA tube power; curved Ge monochromator; 0.02 °2θ step size, 48 s step time, 1.5-50.5 °2θ scanning range; detector mode: step scan; 1 °2θ detector step; standard sample preparation: 10 to 20 mg sample was placed between two acetate foils or Kapton foils; sample holder: Stoe transmission sample holder; the sample was rotated during the measurement.

Thermogravimetry Coupled to Infrared Spectroscopy (TG-FTIR)

TG-FTIR was performed on a Netzsch Thermo-Microbalance TG 209, which was coupled to a Bruker FT-IR Spectrometer Vector 22 or IFS 28. The measurements were carried out with aluminum crucibles with a micro pinhole under a nitrogen atmosphere and at a heating rate of 10° C./min over the range 25° C. to 250° C. or 300° C.

Differential Scanning Calorimetry (DSC)

Differential scanning calorimetry was carried out with a TA Instruments DSC Q2000 using hermetically sealed gold sample pans. The heating rate was 10° C. per minute.

Dynamic Vapor Sorption (DVS)

DVS measurements were performed with an SPS11-100n "Sorptions Prufsystem" of Projekt Messtechnik", D-89077 Ulm (Germany). About 20 to 100 mg of sample were put into an aluminum sample pan. Humidity change rates of 5% per hour were used. The applied measurement program is visualized in the figures.

Sonication

A laboratory ultrasound device 150 W was used.

Polarized Light Microscopy

Polarized light microscopic images were taken using a Leitz microscope.

$^1$HNMR $^1$HNMR spectra were recorded on a Bruker DPX 300 spectrometer. Solvent: deuterated DMSO or deuterated DMF.

pH Measurement

A Metrohm 780 pH meter equipped with an unitrode was used for determination of pH values.

Solvents

For all experiments, Merck, Fluka, Sigma—Aldrich or Lab Scan Analytical Services grade solvents were used.

HPLC

The HPLC method used in this study is described in the Cambrex document No AP1-0548 V3. Compound 1 purity and most of the impurities are given in area % at 280 nm and benzoic acid in area % at 223 nm. Benzoic acid content in % w/w was not determined.

Example 1—Crystallization Experiments in Water and Organic Solvent/Water Mixtures Crystallization experiments in water, methanol, and a number of organic solvent/water mixtures with different water activities were conducted. As set forth below, the experiments revealed that Form A was stable under water activity conditions between about 0.2 and 1.0. As shown below, Form A was formed from solvent systems with a water activity of about 0.2 or above (e.g., about 0.18 or above). Table 9 below gives a summary of crystallization experiments and the resulting morphic form. As shown in Table 9, the solvent:water ratios are given in terms of a volume:volume (v/v) ratio. If the solubility at elevated temperature was <20 mg/mL, the crystallization technique used was suspension equilibration. Precise experimental procedures are given below.

TABLE 9

Crystallization Experiments in Water, Methanol, and Organic Solvent/Water Mixtures

| Experiment No. | Solvent System | Estimated Water Activity | Crystallization Technique | Crystal Form |
|---|---|---|---|---|
| 1 | Water | 1 | Suspension equilibration 90° C. (2 days) Cooling RT (2 hours) Suspension equilibration RT (2 hours) Filter centrifugation | A |
| 2 | THF:Water 1:1 | 0.94 | Cooling solution 60° C. to RT Suspension equilibration RT (4 days) Filter centrifugation | A |
| 3 | Acetone:Water 4:1 | 0.82 | Suspension equilibration 54° C. (3 days) Hot filtration and air drying (22° C./36% RH) | A |
| 4 | DMA:Water 1:1 | 0.8 | Cooling Solution 90° C. to RT Suspension equilibration RT (1 day) Filter centrifugation | A |
| 5 | DMF:Water 1:1 | 0.79 | Cooling Solution 90° C. to RT Suspension equilibration RT (1 day) Filter centrifugation | A |
| 6 | DMSO:Water 1:1 | 0.68 | Cooling Solution 90° C. to RT Suspension equilibration RT (1 day) Filter centrifugation | A |
| 7 | MeOH:Water 9:1 | 0.29 | Suspension equilibration 54° C. (3 days) Hot filtration and air drying (22° C./35% RH) | A |

TABLE 9-continued

Crystallization Experiments in Water, Methanol, and Organic Solvent/Water Mixtures

| Experiment No. | Solvent System | Estimated Water Activity | Crystallization Technique | Crystal Form |
|---|---|---|---|---|
| 8 | MeOH:Water 95:5 | 0.18 | Suspension equilibration 54° C. (3 days) Hot filtration and air drying (22° C./35% RH) | A |
| 9, 10 | MeOH | <0.1 | Cooling solution 60° C. to RT | B |

Experiment No. 1

103 mg of a sample of Compound 1 was suspended at 90° C. in 5.0 mL of water (water activity 1.00). Weak suspension was stirred at 90° C. for 2 days. Weak suspension was cooled to 30° C. in about 2 hours. Suspension was stirred at r.t. for about 2 hours and centrifuged (filter centrifugation).

Experiment No. 2

106 mg of a sample of Compound 1 was dissolved at 60° C. in 2.5 mL of THF/water 1:1 v/v (water activity about 0.94). Solution was cooled to r.t. and stirred at r.t. for 4 days. Weak suspension was centrifuged (filter centrifugation).

Experiment No. 3

110 mg of a sample of Compound 1 was suspended at 60° C. in 5.0 mL of acetone/water 4:1 v/v (water activity about 0.82). Suspension was cooled to 54° C. and stirred at 54° C. for 3 days. Suspension was filtered (hot filtration) and air dried (22° C./36% r.h.).

Experiment No. 4

104 mg of a sample of Compound 1 was dissolved at 90° C. in 1.5 mL of DMA/water 1:1 v/v (water activity about 0.8). Solution was cooled to r.t. and stirred at r.t. for 1 day. Suspension was centrifuged (filter centrifugation).

Experiment No. 5

103 mg of a sample of Compound 1 was dissolved at 90° C. in 1.0 mL of DMF/water 1:1 v/v (water activity about 0.79). Solution was cooled to r.t. and stirred at r.t. for 1 day. Suspension was centrifuged (filter centrifugation).

Experiment No. 6

103 mg of a sample of Compound 1 was dissolved at 90° C. in 1.5 mL of DMSO/water 1:1 v/v (water activity about 0.68). Solution was cooled to r.t. and stirred at r.t. for 1 day. Suspension was centrifuged (filter centrifugation).

Experiment No. 7

110 mg of a sample of Compound 1 was suspended at 60° C. in 5.0 mL of methanol/water 9:1 v/v (water activity about 0.29). Suspension was cooled to 54° C. and stirred at 54° C. for 3 days. Suspension was filtered (hot filtration) and air dried (22° C./35% r.h.).

Experiment No. 8

110 mg of a sample of Compound 1 was suspended at 60° C. in 5.0 mL of methanol/water 95:5 v/v (water activity about 0.18). Suspension was cooled to 54° C. and stirred at 54° C. for 3 days. Suspension was filtered (hot filtration) and air dried (22° C./35% r.h.).

Experiment No 9: Dissolution of a sample of Compound 1 was in methanol at 60° C., followed by partial evaporation of the solvent and cooling the sample to room temperature.

Experiment No. 10

Dissolution of a sample of Compound 1 was in methanol at 60° C., followed by partial evaporation of the solvent and cooling the sample to room temperature.

Example 2—Crystallization from Solutions in Organic Solvents

Crystallization by cooling of solutions of Compound 1 in organic solvents as well as precipitation experiments by addition of organic antisolvents to solutions in DMSO resulted in the formation of solvates of Compound 1. Table 10 below gives a summary of the experimental protocols, and the protocols are given in more detail below.

TABLE 10

Crystallization from Solutions of Compound 1 in Organic Solvents

| Experiment No. | Solvent | Antisolvent | Crystal Form |
|---|---|---|---|
| 11, 12, 13 | Methanol | None | B (methanol hemisolvate) |
| 14 | Ethanol | None | C (ethanol hemisolvate) |
| 15 | DMSO | 2-propanol | F (2-propanol hemisolvate; preliminary) |
| 16 | DMSO | acetone | G (DMSO solvate; preliminary) |

Experiment No. 11

103 mg of a sample of Compound 1 was dissolved at 60° C. in 5.0 mL of methanol. Solution was cooled to r.t. and stirred at r.t. for 3 days. Weak suspension was filtered and air dried (22° C./36% r.h.).

Experiment No. 12

Dissolution of a sample of Compound 1 in methanol at 60° C., followed by partial evaporation of the solvent and cooling the sample to room temperature.

Experiment No. 13

Dissolution of a sample of Compound 1 in methanol at 60° C., followed by partial evaporation of the solvent and cooling the sample to room temperature.

Experiment No. 14

Dissolution of a sample of Compound 1 in ethanol at 80° C., followed by partial evaporation of the solvent and cooling the sample to room temperature.

Experiment No. 15

Dissolution of a sample of Compound 1 in DMSO and precipitation at room temperature using 2-propanol.

Experiment No. 16

Dissolution of a sample of Compound 1 in DMSO and precipitation at room temperature using acetone.

Example 3—Suspension Equilibration of Compound 1, Form A in Organic Solvents

Compound 1, Form A was stirred in methanol at room temperature for six days. After this period, the PXRD of a sample of the suspension showed the presence of the hemihydrate. At least 90% of Form A was still present.

Additionally, Compound 1, Form A was stirred in acetonitrile at a temperature ranging between 52° C. and 75° C. for five days. The resulting crystalline material showed a PXRD pattern similar to Compound 1, Form D. TG-FTIR of the sample showed a reduced water content (to ≤1.6%).

As set forth above, transformations of Compound 1, Form A by suspension equilibration was found to be slow.

Example 4—Additional Preparative Procedures

Additional synthetic protocols for various morphic Forms of Compound 1 are given below.

Form A

Form A was prepared by suspension at equilibrium in THF at 25° C. Form A was prepared by suspension equilibrium in acetone at 52° C. Form A was prepared by suspension equilibrium in 2-propanol at 75° C. and at 52° C. Form A was prepared by suspension at equilibrium in water at 25° C. Form A was prepared by suspension at equilibrium in THF:water (1:1, v/v) at 25° C. Form A was prepared by suspension at equilibrium in DMA:water (1:1, v/v) at 25° C. Form A was prepared by suspension at equilibrium in methanol:water (9:1, v/v) at 25° C.

Form A was also prepared by storing the mother liquor from Experiment 2 (Example 1; Form A) and partially evaporating the solvent. After 1 day, about 40% of the solvent had evaporated. The suspension was centrifuged and filtered to produce Form A.

Form A was prepared by suspending 100 mg Compound 1 (Form A) at 60° C. in 5.0 mL THF. The suspension was cooled to 54° C. and stirred at 54° C. for 3 days. The suspension was filtered and air dried at 22° C. and 35% relative humidity to give Form A.

Form A was prepared by treating the product of Experiment 9 (Example 1; Form B) under the conditions of dynamic vapor sorption (DVS) from 50% relative humidity to 0% relative humidity to 95% relative humidity to 50% relative humidity.

Form A was prepared by suspending 151.8 mg of Compound 1 (Form A) at room temperature (25° C.) in 15.00 mL of 1M aqueous HCl followed by addition of 15.00 mL of 1M aqueous NaOH. The resulting solution was about pH 6. The sample was sonicated and stirred at room temperature for about 2 hours. A suspension was formed, resulting in Form A.

Forms A and C

A mixture of Form A and Form C was prepared by cooling a solution of Compound 1 (Form A) in about 8 mL ethanol from 75° C. to about 25° C. (i.e., to room temperature).

Form B

Form B was prepared by heating the product of Experiment 10 (Example 1; Form B) under dry nitrogen flow up to about 80° C.

Form D

Form D was prepared by heating a sample of Compound 1 (Form A) under dry nitrogen flow up to about 200° C. or about 207° C. The same sample remained as Form D after the conditions of dynamic vapor sorption from 50% relative humidity to 0% relative humidity to 95% relative humidity to 50% relative humidity.

Form E

Form E was prepared by heating the product of Experiment 9 (Example 1; Form B) under a dry nitrogen flow up to about 200° C. The product was converted to Form A under the conditions of dynamic vapor sorption at 50% relative humidity to 0% relative humidity to 95% relative humidity to 50% relative humidity.

Form E was prepared by heating the product of Experiment 14 (Example 2; Form C) under dry nitrogen flow up to about 200° C.

Form E was prepared by heating the product of Experiment 10 (Example 1; Form B) under dry nitrogen flow up to about 200° C.

Example 5—Thermodynamic Stability

A mixture of Compound 1, Forms A, B, C, D, E, F and G was stirred in DMF/water 1:1 v/v (water activity about 0.79). After stirring the suspension for four days at room temperature PXRD showed only the peaks of crystal form A.

A mixture of Compound 1, Forms A, B, C, D, E, F and G was stirred in methanol/water 95:5 v/v (water activity about 0.18). After stirring the suspension for four days at room temperature PXRD showed only the peaks of crystal form A.

Accordingly, the above-results suggest that morphic Form A is the most thermodynamically stable of the seven morphic forms identified.

Example 6—Development of Large-Scale Crystallization Conditions for Form A

This example explored suitable crystallization processes to produce Compound 1, Form A on a multi-gram scale. Process development investigated purity, yield, crystal form, residual solvent content, and particle size distribution.

With the exception of the approximate solubility investigations, all experiments set forth in this example began with the same two hundred-gram sample of crude Compound 1. The sample comprised Form A of Compound 1, and 1.4% total impurity. Specifically, the sample comprised 0.57% benzoic acid (w/w); 0.44% of Impurity No. 1 (by HPLC; RRT about 0.54); and 0.41% of Impurity No. 2, (by HPLC; RRT about 1.13). The structure of Impurity Nos. 1 and 2 are shown below:

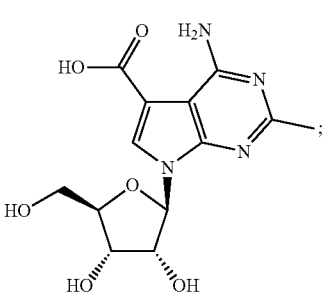

Impurity No. 1 (RRT about 0.54)

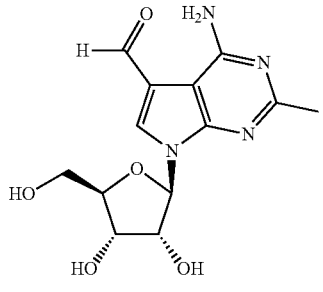

Impurity No. 2 (RRT about 1.13)

Preliminary Investigations: Approximate Solubility Compound 1

To determine approximate solubility of Compound 1, solvent was added in steps to the solid material (about 20 to 100 mg). The solubility values were rough approximations. Therefore, these values were used solely for the preliminary design of subsequent crystallization experiments. The results of the approximate solubility determinations are given in Table 11.

TABLE 11

Approximate solubility of Compound 1 in Various Solvents

| Solvent/Mixture | Solubility [S, mg/mL] | |
|---|---|---|
| | RT | 60° C. |
| Water | <1.3 | ~3 |
| NaOH aq 1M | ~60 | ~95 |
| NaOH aq 0.5M | ~16 | ~38 |
| NaOH aq 0.1M | ~3 | ~9 |
| DMSO | ~500 | — |
| DMSO/water 1:1 v/v | ~8 | (~45 at 80° C.) |
| DMSO/NaOH aq 0.1M 1:1 v/v | ~20 | — |
| DMSO/water 1:2 v/v | ~3 | — |
| 2-Propanol/water 2:1 v/v | ~6 | — |
| 2-Propanol/water 1:1 v/v | ~7 | — |
| 2-Propanol/NaOH aq 0.1M 1:1 v/v | ~16 | — |
| 2-Propanol/water 1:2 v/v | ~5 | (~31 at 70° C.) |
| 1-Propanol/water 2:1 v/v | ~7 | — |
| 1-Propanol/water 1:2 v/v | ~6 | (~51 at 80° C.) |
| Ethanol | 1.7 | — |
| THF | <1 | — |
| THF/water 4:1 v/v | ~15 | — |
| THF/water 1:1 v/v | ~22 | — |
| THF/water 1:4 v/v | ~6 | — |

Based on the preliminary investigations set forth above in Table 11, the following potentially useful solvent systems for crystallization of Form A were identified: (1) Aqueous 1M NaOH (initial concentration of NaOH at 60° C.) and aqueous 0.1 M or 0.01M NaOH (final concentration of NaOH at room temperature); (2) DMSO/aqueous NaOH 0.01 M 1:2 v/v (final concentration of NaOH at room temperature); (3) 2-Propanol/aqueous NaOH 0.01 M 1:3 v/v (final concentration of NaOH at room temperature); (4) 1-Propanol/aqueous NaOH 0.01 M 1:3 v/v (final concentration of NaOH at room temperature); (5) Ethanol/aqueous NaOH 0.01 M 1:3 v/v (final concentration of NaOH at room temperature); (6) DMSO/water 1:1 v/v; (7) 2-Propanol/water 1:2 v/v; (8) 1-Propanol/water 1:2 v/v; and (9) Water (or <0.01M NaOH).

Exact Solubility of Compound 1

The exact solubilities of Compound 1 Form A in selected solvent systems were determined at 24° C. and 60° C. About 100 mg of Compound 1 Form A were suspended in 2.0 mL of solvent and stirred using a magnetic stirrer bar for 1 day at 24° C. or 60° C., followed by filter centrifugation at the corresponding temperature. The concentration of Compound 1 was then determined by HPLC.

Exact Solubility of Compound 1 at 24° C. and 60° C.

The exact solubilities of Form A in selected solvent systems were determined at 24° C. and 60° C. About 100 mg of Compound 1 were suspended in 2.0 mL of solvent and stirred using a magnetic stirrer bar for 1 day at 24° C. or 60° C., followed by filter centrifugation at the corresponding temperature. The concentration of Compound 1 was then determined by HPLC. The results of the exact solubility determinations are given in Table 12.

TABLE 12

Exact solubility of Compound 1 in Various Solvents

| Solvent/Mixture | Solubility [mg/mL] | |
|---|---|---|
| | 24° C. | 60° C. |
| NaOH aq 0.1M | 2.8 | 8.0 |
| NaOH aq 0.01M | 0.81 | — |
| DMSO/NaOH aq 0.1M 1:2 v/v | 12.5 | — |
| DMSO/NaOH aq 0.01M 1:2 v/v | 4.8 | 19.6 |
| 2-Propanol/NaOH aq 0.1M 1:3 v/v | 14.1 | — |
| 2-Propanol/NaOH aq 0.01M 1:3 v/v | 5.2 | 16.9 |
| 1-Propanol/NaOH aq 0.1M 1:3 v/v | 16.6 | — |
| 1-Propanol/NaOH aq 0.01M 1:3 v/v | 6.8 | 25.9 |
| Ethanol/NaOH aq 0.1M 1:3 v/v | 9.0 | — |
| Ethanol/NaOH aq 0.01M 1:3 v/v | 3.3 | 15.3 |
| 2-Propanol/water 1:2 v/v | — | 26.6 |
| 1-Propanol/water 1:2 v/v | — | 30.9 |
| DMSO/water 1:1 v/v | — | 18.7 |

HPLC Analysis for the Solutions of the Solubility Experiments

Most of the HPLC chromatograms of the solutions of the exact solubility determinations shown above in Table 12 exhibited higher levels of the impurities benzoic acid, Impurity No. 1 and Impurity No. 2 as shown below in Table 13. Without wising to be bound by theory, this enrichment of the impurities in the solutions indicates purification of crude Compound 1 during suspension equilibration, especially at 60° C. Without wising to be bound by theory, it is likely that the enrichment of Impurity No. 1 is due to degradation only when using 0.1M NaOH over a period of 24 hours.

TABLE 13

HPLC Analysis for the Solutions of the Exact Solubility Determinations

| Solvent/Mixture | 24° C. (area %; 280 nm) | 60° C. (area %; 280 nm) |
|---|---|---|
| Crude Compound 1 prior to solubility measurements | Compound 1: 99.08<br>benzoic acid (223 nm): 1.14<br>Impurity No. 1: 0.45<br>RRT 0.67: 0.02<br>Impurity No. 2: 0.41 | — |
| NaOH aq 0.1M | Compound 1: 92.62<br>benzoic acid (223 nm): 14.38<br>Impurity No. 1: 5.12<br>RRT 0.67: 0.19<br>Impurity No. 2: 1.52 | Compound 1: 70.21<br>benzoic acid (223 nm): 4.29<br>Impurity No. 1: 28.79<br>RRT 0.67: 0.08<br>Impurity No. 2: 0.72 |
| NaOH aq 0.01M | Compound 1: 86.56<br>benzoic acid (223 nm): 36.65<br>Impurity No. 1: 7.43<br>RRT 0.67: 0.54<br>Impurity No. 2: 3.59 | — |
| DMSO/NaOH aq 0.1M 1:2 v/v | Compound 1: 97.96<br>benzoic acid (223 nm): 3.78<br>Impurity No. 1: 1.15<br>RRT 0.67: 0.05<br>Impurity No. 2: 0.67 | — |
| DMSO/NaOH aq 0.01M 1:2 v/v | Compound 1: 96.87<br>benzoic acid (223 nm): 9.28<br>Impurity No. 1: 1.60<br>RRT 0.67: 0.10<br>Impurity No. 2: 1.05 | Compound 1: 97.71<br>benzoic acid (223 nm): 2.43<br>Impurity No. 1: 1.38<br>RRT 0.67: 0.06<br>Impurity No. 2: 0.76 |
| 2-Propanol/NaOH aq 0.1M 1:3 v/v | Compound 1: 98.04<br>benzoic acid (223 nm): 3.77<br>Impurity No. 1: 1.17<br>RRT 0.67: 0.06<br>Impurity No. 2: 0.62 | — |
| 2-Propanol/NaOH aq 0.01M 1:3 v/v | Compound 1: 96.38<br>benzoic acid (223 nm): 9.79<br>Impurity No. 1: 1.93<br>RRT 0.67: 0.13<br>Impurity No. 2: 1.24 | Compound 1: 97.48<br>benzoic acid (223 nm): 2.90<br>Impurity No. 1: 1.64<br>RRT 0.67: 0.06<br>Impurity No. 2: 0.72 |
| 1-Propanol/NaOH aq 0.1M 1:3 v/v | Compound 1: 98.00<br>benzoic acid (223 nm): 3.35<br>Impurity No. 1: 1.16<br>RRT 0.67: 0.05<br>Impurity No. 2: 0.68 | — |
| 1-Propanol/NaOH aq 0.01M 1:3 v/v | Compound 1: 98.00<br>benzoic acid (223 nm): 6.57<br>Impurity No. 1: 0.99<br>RRT 0.67: 0.07<br>Impurity No. 2: 0.73 | Compound 1: 97.83<br>benzoic acid (223 nm): 2.25<br>Impurity No. 1: 1.40<br>RRT 0.67: 0.05<br>Impurity No. 2: 0.65 |
| Ethanol/NaOH aq 0.1M 1:3 v/v | Compound 1: 97.93<br>benzoic acid (223 nm): 5.45<br>Impurity No. 1: 1.22<br>RRT 0.67: 0.05<br>Impurity No. 2: 0.62 | — |
| Ethanol/NaOH aq 0.01M 1:3 v/v | Compound 1: 95.00<br>benzoic acid (223 nm): 10.74<br>Impurity No. 1: 2.70<br>RRT 0.67: 0.21<br>Impurity No. 2: 1.72 | Compound 1: 96.53<br>benzoic acid (223 nm): 3.97<br>Impurity No. 1: 2.37<br>RRT 0.67: 0.10<br>Impurity No. 2: 0.85 |
| 2-Propanol/water 1:2 v/v | — | Compound 1: 98.60<br>benzoic acid (223 nm): 1.97<br>Impurity No. 1: 0.71<br>RRT 0.67: 0.05<br>Impurity No. 2: 0.58 |
| 1-Propanol/water 1:2 v/v | — | Compound 1: 98.76<br>benzoic acid (223 nm): 2.08<br>Impurity No. 1: 0.61<br>RRT 0.67: 0.05<br>Impurity No. 2: 0.51 |
| DMSO/water 1:1 v/v | — | Compound 1: 98.21<br>benzoic acid (223 nm): 3.23<br>Impurity No. 1: 0.91<br>RRT 0.67: 0.06<br>Impurity No. 2: 0.71 |

PXRD of Solid Residues and HPLC Analysis for Selected Solid Residues

The solid residues of the solubility determinations were characterized by PXRD. All solid residues showed the pattern of Compound 1 hemihydrate (Form A).

Selected solid residues after the solubility determinations were also tested by HPLC (see Table 14). These characterizations were performed in order to get a preliminary insight into purification or degradation during suspension equilibration. All the samples tested showed somewhat higher HPLC purities compared to the crude Compound 1, including the solid residue of the solubility determination in 0.1M NaOH at 60° C. These results indicate that suspension equilibration is not effective enough for elimination of the main impurities.

Small Scale Crystallization Experiments

Small scale crystallization experiments were carried out using a Mettler Toledo MultiMax system with 50 mL glass vessels equipped with magnetic stirrer bars and turbidity probes. For vacuum filtration sintered glass funnels were used (porosity P4; diameter 20 mm or 73 mm).

First Iteration

The initially selected solvent systems for crystallization experiments at the 10 mL to 20 mL scale are given in Table 15. Without wishing to be bound by theory, these solvent systems were chosen in view of the solubility measurements set forth above in view of the following observations: (i) 1-Propanol/water 1:2 v/v showed a workable solubility profile and allows using a broad temperature range; (ii) Starting with 1-propanol/NaOH aq 0.1M 1:3 v/v could be

TABLE 14

HPLC Analysis for Selected Solid Residues of the Exact Solubility Determinations

| Solvent/Mixture | 24° C. (area %; 280 nm) | 60° C. (area %; 280 nm) |
| --- | --- | --- |
| Crude Compound 1 prior to solubility measurements | Compound 1: 99.08<br>benzoic acid (223 nm): 1.14<br>Impurity No. 1: 0.45<br>RRT 0.67: 0.02<br>Impurity No. 2: 0.41 | — |
| NaOH aq 0.1M | Compound 1: 99.27<br>benzoic acid (223 nm): 0.11<br>Impurity No. 1: 0.35<br>RRT 0.67: 0.02<br>Impurity No. 2: 0.35 | Compound 1: 99.32<br>benzoic acid (223 nm): 0.09<br>Impurity No. 1: 0.39<br>RRT 0.67: 0.02<br>Impurity No. 2: 0.28 |
| NaOH aq 0.01M | Compound 1: 99.28<br>benzoic acid (223 nm): 0.15<br>Impurity No. 1: 0.34<br>RRT 0.67: 0.02<br>Impurity No. 2: 0.36 | — |
| DMSO/NaOH aq 0.1M 1:2 v/v | — | — |
| DMSO/NaOH aq 0.01M 1:2 v/v | Compound 1: 99.38<br>benzoic acid (223 nm): 0.14<br>Impurity No. 1: 0.30<br>RRT 0.67: <0.01<br>Impurity No. 2: 0.32 | Compound 1: 99.59<br>benzoic acid (223 nm): 0.07<br>Impurity No. 1: 0.18<br>RRT 0.67: <0.01<br>Impurity No. 2: 0.23 |
| 2-Propanol/NaOH aq 0.1M 1:3 v/v | — | — |
| 2-Propanol/NaOH aq 0.01M 1:3 v/v | Compound 1: 99.34<br>benzoic acid (223 nm): 0.12<br>Impurity No. 1: 0.31<br>RRT 0.67: 0.02<br>Impurity No. 2: 0.33 | Compound 1: 99.58<br>benzoic acid (223 nm): 0.07<br>Impurity No. 1: 0.17<br>RRT 0.67: 0.01<br>Impurity No. 2: 0.24 |
| 1-Propanol/NaOH aq 0.1M 1:3 v/v | — | — |
| 1-Propanol/NaOH aq 0.01M 1:3 v/v | Compound 1: 99.31<br>benzoic acid (223 nm): 0.12<br>Impurity No. 1: 0.33<br>RRT 0.67: 0.02<br>Impurity No. 2: 0.34 | — |
| Ethanol/NaOH aq 0.1M 1:3 v/v | — | — |
| Ethanol/NaOH aq 0.01M 1:3 v/v | Compound 1: 99.42<br>benzoic acid (223 nm): 0.10<br>Impurity No. 1: 0.27<br>RRT 0.67: <0.01<br>Impurity No. 2: 0.30 | Compound 1: 99.57<br>benzoic acid (223 nm): 0.08<br>Impurity No. 1: 0.17<br>RRT 0.67: <0.01<br>Impurity No. 2: 0.26 |
| 2-Propanol/water 1:2 v/v | — | Compound 1: 99.49<br>benzoic acid (223 nm): 0.09<br>Impurity No. 1: 0.24<br>RRT 0.67: 0.01<br>Impurity No. 2: 0.26 |
| 1-Propanol/water 1:2 v/v | — | — |
| DMSO/water 1:1 v/v | — | Compound 1: 99.45<br>benzoic acid (223 nm): 0.11<br>Impurity No. 1: 0.25<br>RRT 0.67: 0.02<br>Impurity No. 2: 0.28 | useful if the solubility at 60° C. can be significantly increased; (iii) Starting with DMSO/NaOH aq 0.1M 1:2 v/v might be useful if the solubility at 60° C. can be significantly increased; (iv) Starting with NaOH aq 1M at 60° C. is close to the conditions used in the THF/aqueous NaOH process for hydrolysis after evaporation of THF. Detailed experimental procedures are given below.

TABLE 15

Selected Solvent Systems for Crystallization Experiments at to 10-mL to 20-mL Scale

| | Solvent system | | Temperature | | | |
|---|---|---|---|---|---|---|
| Process/Exp. No. | Initial | Final | Initial | Final | Seeding | Cooling rate |
| 17 | 1-PrOH/H2O 1:2 v/v | 1-PrOH/H2O 1:2 v/v | 80° C. | 10° C. | 60° C. | 80° C. to 60° C.: 20 K/hour 60° C. to 10° C.: 5 K/hour |
| 18 | 1-PrOH/NaOH aq 0.1M 1:3 v/v | 1-PrOH/NaOH aq 0.01M about 1:3 v/v (addition of aqueous 1M acetic acid solution at 60° C.). | 60° C. | 10° C. | 60° C. | 5 K/hour |
| 19 | DMSO/NaOH aq 0.1M 1:2 v/v | DMSO/NaOH aq 0.01M about 1:2 v/v (addition of aqueous 1M acetic acid solution at 60° C.). | 60° C. | 10° C. | 60° C. | 5 K/hour |
| 20 | NaOH aq 1M | NaOH aq 0.01M (addition of aqueous 1M acetic acid solution at 60° C.). | 60° C. | 10° C. | 60° C. | 5 K/hour |

Experiment No. 17

971 mg of crude Compound 1 were suspended in 20 mL of 1-propanol/water 1:2 v/v, stirred using a magnetic stirrer and heated to 80° C. in 30 minutes. After stirring at 80° C. for about 2 minutes the solution formed was then cooled to 60° C. with a cooling rate of 20K/hour. At 60° C. the solution was seeded with a suspension of 25 mg of crude Compound 1 in 1 mL of water. The weak suspension formed was stirred at 60° C. for 5 minutes, cooled to 10° C. with a cooling rate of 5K/hour and then stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was again washed with 5 mL of water and air dried for 15 minutes by drawing ambient air through the glass funnel. The off-white solid was then vacuum dried at about 45° C./about 20 mbar overnight. Yield (corrected for seeding material): 797 mg (82.1%) and 99.59% pure by HPLC.

Experiment No. 18

1258 mg of crude Compound 1 were suspended in 20 mL of 1-propanol/0.1 M aq NaOH 1:3 v/v, stirred using a magnetic stirrer and heated to 60° C. in 30 minutes. Additional 1-propanol/0.1 M aq NaOH 1:3 v/v was added at 60° C. in 2 mL steps in about 20 minutes until a solution was formed (total volume of 1-propanol/0.1 M aq NaOH 1:3 v/v: 36 mL). At 60° C. a total of 2.43 mL of 1M aq acetic acid solution was then added in 0.243 mL steps in about 20 minutes. After addition of 0.729 mL the solution was seeded with a suspension of 26 mg sample of crude Compound 1 in 1 mL of water resulting in a very weak suspension. After complete addition of 1M aq acetic acid the weak suspension formed was cooled to 10° C. with a cooling rate of 5K/hour and stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was washed with 5 mL of water and air dried for 15 minutes by drawing ambient air through the glass funnel. The off-white solid was then vacuum dried at about 45° C./about 20 mbar overnight. Yield (corrected for seeding material): 1050 mg (83.5%) and 99.73% pure by HPLC.

Experiment No. 19

1020 mg sample of crude Compound 1 was suspended in 20 mL of DMSO/0.1 M aq NaOH 1:2 v/v, stirred using a magnetic stirrer and heated to 60° C. in 30 minutes. Additional DMSO/0.1 M aq NaOH 1:2 v/v was added at 60° C. in 2 mL steps in about 20 minutes until a solution was formed (total volume of DMSO/0.1 M aq NaOH 1:2 v/v: 31 mL). At 60° C. a total of 1.86 mL of 1M aq acetic acid solution was then added in 0.186 mL steps in about 20 minutes. After addition of 0.558 mL the solution was seeded with a suspension of 25 mg crude Compound 1 in 1 mL of water resulting in a very weak suspension. After complete addition of 1M aq acetic acid the weak suspension formed was cooled to 10° C. with a cooling rate of 5K/hour and stirred overnight at 10° C.

The easy-to-stir suspension was then filtered using a sintered glass funnel (porosity P4). The suspension was easy to filter. The glass reactor was flushed with 5 mL of water and the washing suspension was also filtered. The filter cake was washed with 5 mL of water and air dried for 15 minutes by drawing ambient air through the glass funnel. The off-white solid was then vacuum dried at about 45° C./about 20 mbar overnight. Yield (corrected for seeding material): 864 mg (84.7%) and 99.70% pure by HPLC.

Experiment No. 20

914 mg sample of crude Compound 1 was suspended in 10 mL of 1M aq NaOH, stirred using a magnetic stirrer and heated to 60° C. in 15 minutes. After stirring at 60° C. for about 2 minutes a clear solution was present. At 60° C. a total of 9.90 mL of 1M aq acetic acid solution was added in 0.99 mL steps in about 20 minutes. After addition of 2.97 mL the solution was seeded with a suspension of 25 mg of crude Compound 1 in 1 mL of water resulting in a suspension. After complete addition of 1M aq acetic acid the suspension formed was cooled to 10° C. with a cooling rate of 5K/hour and stirred overnight at 10° C.

The easy-to-stir suspension was then filtered using a sintered glass funnel (porosity P4). The suspension was easy to filter. The glass reactor was flushed with 5 mL of water and the washing suspension was also filtered. The filter cake was washed with 5 mL of water and air dried for 15 minutes by drawing ambient air through the glass funnel. The off-white solid was then vacuum dried at about 45° C./about 20 mbar overnight. Yield (corrected for seeding material): 813 mg (88.9%) and 99.52% pure by HPLC.

The HPLC of samples from Exp. Nos. 17-20 showed that all four processes significantly removed benzoic acid (<0.01 area %). Impurity No. 1 was significantly reduced by Exp. Nos. 18 and 19 (<0.01 area %). The volume of solvent necessary to dissolve one gram of Compound 1 was relatively high. For Exp. Nos. 17 and 20 the volume of solvent was lower but Impurity No. 1 was only reduced to a certain degree. The content of Impurity No. 2 was only partially decreased by all four Experiments 17-20.

Without wishing to be bound by theory, a better method for the reduction of the content of Impurity No. 1 seemed to be to use a mixture of 1-propanol/0.01 M aqueous NaOH instead of 1-propanol/water, or to start with 1-propanol/0.1 M aq NaOH at 80° C. instead of 60° C. in order to reduce the volume of solvent. Accordingly, two additional experiments were carried out in the second iteration.

Second Iteration

Experiment No. 21

1007 mg of crude Compound 1 was suspended in 10 mL of 1-propanol/0.01 M aq NaOH 1:2 v/v, stirred using a magnetic stirrer and heated to 80° C. in 30 minutes. The suspension was then stirred at 80° C. for 10 minutes and additional 1-propanol/0.01 M aq NaOH 1:2 v/v was added at 80° C. in 2-mL steps in about 10 minutes until a solution was formed (total volume of 1-propanol/0.01 M aq NaOH 1:2 v/v: 20.0 mL). The solution was then cooled to 60° C. with a cooling rate of 20K/hour.

At 60° C. the solution was seeded with a suspension of 25 mg of crude Compound 1 in 1 mL of water. The very weak suspension formed was stirred at 60° C. for 20 minutes, cooled to 10° C. with a cooling rate of 5K/hour and then stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was again washed with 5 mL of water and air dried for 15 minutes by drawing ambient air through the glass funnel. The off-white solid was then vacuum dried at about 45° C./about 10 mbar overnight. Yield (corrected for seeding material): 819 mg (81.3%) and 99.73% pure by HPLC.

Experiment No. 22

1260 mg of crude Compound 1 was suspended in 20 mL of 1-propanol/0.1 M aq NaOH 1:3 v/v, stirred using a magnetic stirrer and heated to 80° C. in 30 minutes. After stirring at 80° C. for about 20 minutes the solution was cooled to 60° C. with a cooling rate of 20K/hour. At 60° C. a total of 1.35 mL of 1M aq acetic acid solution was added in 0.135 mL steps in about 20 minutes. After addition of 0.405 mL the solution was seeded with a suspension of 25 mg of crude Compound 1 in 1 mL of water resulting in a very weak suspension. After complete addition of 1M aq acetic acid the weak suspension formed was cooled to 10° C. with a cooling rate of 5K/hour and stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was washed with 5 mL of water and air dried for 15 minutes by drawing ambient air through the glass funnel. The off-white solid was then vacuum dried at about 45° C./about 10 mbar overnight. Yield (corrected for seeding material): 1081 mg (85.8%) and 99.72% pure by HPLC.

Experiment No. 21 using 1-propanol/0.01 M aqueous NaOH 1:2 v/v instead of 1-propanol/water 1:2 v/v effectively reduced the content of Impurity No. 1 to <0.01 area %. The volume of solvent necessary to dissolve one gram of Compound 1 was 19.8 mL.

Experiment No. 22, starting at 80° C. instead of 60° C., allowed the volume of solvent to be decreased and also effectively reduced the content of the Impurity No. 1 to <0.01 area %. The volume of solvent necessary to dissolve one gram of Compound 1 was 16.9 mL.

The two additional experiments 21 and 22 resulted in significant reduction of Impurity No. 1. Without wishing to be bound by theory, possible ways of attempting to further reduce the volume of solvent seemed to be: (i) starting the 1-PrOH/0.01 M aq NaOH 1:2 v/v process at temperatures around 95° C.; (ii) starting the 1-PrOH/0.01 M aq NaOH process at 80° C. or 95° C. using a ratio of 1:1 instead of 1:2; (iii) starting the 1-PrOH/0.01 M aq NaOH 1:2 v/v process at 80° C. and adding DMSO to try to increase the solubility; (iv) starting the 1-PrOH/0.1 M aq NaOH process at 80° C. using a ratio of 1:1 or 1:2 instead of 1:3. Accordingly, further experimentation was carried out to evaluate ways to reduce the necessary volume of solvent.

Third Iteration

Three additional experiments were carried out in attempt to further reduce the necessary volume of solvent:

Experiment No. 23, Starting the 1-PrOH/0.01 M Aq NaOH 1:2 v/v Process at 90° C., Cooling to 60° C., Seeding and Cooling to 10° C.

1010 mg of crude Compound 1 was suspended in 10 mL of 1-propanol/0.01 M aq NaOH 1:2 v/v, stirred using a magnetic stirrer and heated to 90° C. in 30 minutes. The suspension was then stirred at 90° C. for 3 minutes and additional 1-propanol/0.01 M aq NaOH 1:2 v/v was added at 90° C. in about 4 minutes until a solution was formed (total volume of 1-propanol/0.01 M aq NaOH 1:2 v/v: 12.5 mL). The solution was then cooled to 60° C. with a cooling rate of 20K/hour.

At 60° C. the solution was seeded with a suspension of 26 mg of crude Compound 1 in 1 mL of water. The very weak suspension formed was stirred at 60° C. for 5 minutes, cooled to 10° C. with a cooling rate of 5K/hour and then stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was again washed with 5 mL of water and air dried for 15 minutes by drawing ambient air through the glass funnel. The off-white solid was then vacuum dried at about 45° C./about 10 mbar overnight. Yield (corrected for seeding material): 902 mg (89.3%) and 99.76% pure by HPLC.

Experiment No. 24, Starting the 1-PrOH/0.01 M Aq NaOH Process at 90° C. Using a Ratio of 1:1 Instead of 1:2, Cooling to 60° C., Seeding and Cooling to 10° C.

1006 mg of crude Compound 1 was suspended in 10 mL of 1-propanol/0.01 M aq NaOH 1:1 v/v, stirred using a magnetic stirrer and heated to 90° C. in 30 minutes. The suspension was then stirred at 90° C. for 3 minutes and additional 1-propanol/0.01 M aq NaOH 1:1 v/v was added at 90° C. in about 2 minutes until a solution was formed (total volume of 1-propanol/0.01 M aq NaOH 1:1 v/v: 12.0 mL). The solution was then cooled to 60° C. with a cooling rate of 20K/hour.

At 60° C. the solution was seeded with a suspension of 25 mg of crude Compound 1 in 1 mL of water. The very weak suspension formed was stirred at 60° C. for 6 minutes, cooled to 10° C. with a cooling rate of 5K/hour and then stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was again washed with 5 mL of water and air dried for 15 minutes by drawing ambient air through the glass funnel. The off-white solid was then vacuum dried at about 45° C./about 10 mbar overnight. Yield (corrected for seeding material): 888 mg (88.3%) and 99.73% pure by HPLC.

Experiment No. 25, Starting the 1-PrOH/0.1 M Aq NaOH Process at 90° C. Using a Ratio of 1:1 Instead of 1:3, Cooling to 60° C. Followed by Addition of 1M Aq Acetic Acid at 60° C., Seeding and Cooling to 10° C.

999 mg of crude Compound 1 was suspended in 10 mL of 1-propanol/0.1 M aq NaOH 1:1 v/v, stirred using a magnetic stirrer and heated to 90° C. in 30 minutes. At 90° C. a solution was formed. The solution was then cooled to 60° C. with a cooling rate of 20K/hour. At 60° C. a total of 0.09 mL of 1M aq acetic acid solution was then added in 0.018 mL steps in about 9 minutes. After addition of 0.036 mL the solution was seeded with a suspension of 25 mg of crude Compound 1 in 1 mL of water resulting in a very weak suspension. After complete addition of 1M aq acetic acid the weak suspension formed was cooled to 10° C. with a cooling rate of 5K/hour and stirred overnight at 10° C.

The easy-to-stir suspension was filtered using a sintered glass funnel (porosity P4). The suspension was easy to filter. The glass reactor was flushed with 5 mL of water and the washing suspension was also filtered. The filter cake was washed with 5 mL of water and air dried for 15 minutes by drawing ambient air through the glass funnel. The off-white solid was then vacuum dried at about 45° C./about 20 mbar overnight. Yield (corrected for seeding material): 870 mg (87.1%) and 99.71% pure by HPLC.

All three additional experiments (Experiment Nos. 23-25) resulted in significant reduction of the volume of solvent and significant reduction of Impurity No. 1. The volume of solvent necessary to dissolve one gram of Compound 1 was significantly decreased in all three experiments. In all three experiments the suspensions were easy to stir and easy to filter. The yield for all three experiments was high (Exp. No. 23: 89%/Exp. No. 24: 88%/Exp. No. 25: 87%). PXRD showed the pattern of Compound 1 Form A. Benzoic acid was significantly reduced by all three processes (<0.01 area %). Impurity No. 1 was significantly reduced by all three processes (Exp. No. 23: 0.01 area %, Exp. No. 24: 0.01 area % and Exp. No. 25: 0.03 area %). The content of Impurity No. 2 was partially decreased (Exp. No. 23: 0.22 area %/Exp. No. 24: 0.26 area %/Exp. No. 25: 0.26 area %). Accordingly, it was decided to use 1-propanol/0.01 M aq NaOH 1:2 v/v for additional medium scale crystallization experiments.

Metastable Zone Width (MSZW)

Metastable zone width experiments were carried out using a Mettler Toledo MultiMax system with 50 mL glass vessels equipped with magnetic stirrer bars and turbidity probes. The MSZW experiments investigated an appropriate temperature for seeding of the crystallization experiments.

Figure 25:
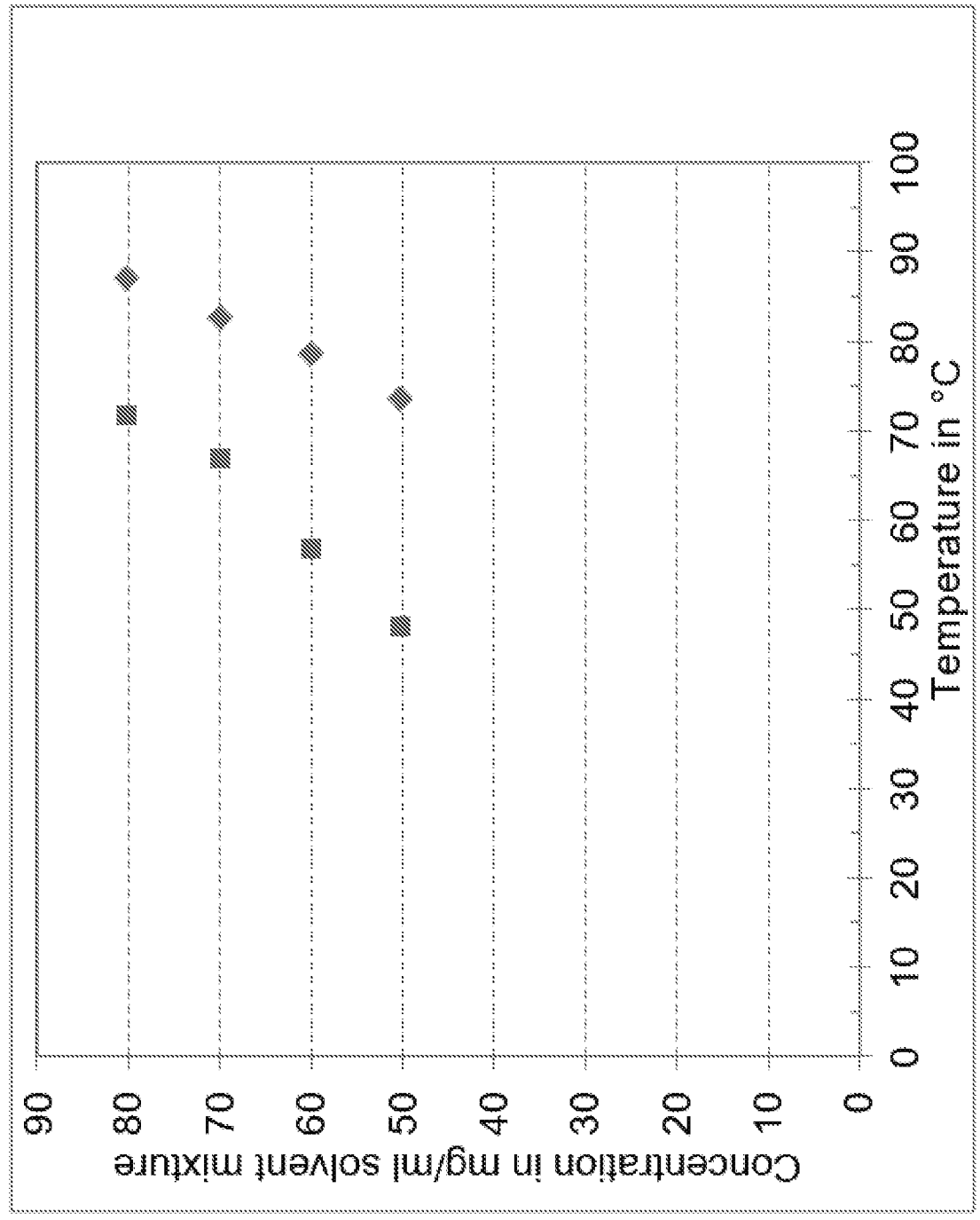
FIG. 25 is a plot showing the results of the metastable zone width (MSZW) experiments using a solvent of 1-PrOH/0.01M NaOH 1:2 (v/v) at a heating and cooling rate of 3K/hour.

In order to further optimize the crystallization process at medium scale, the metastable zone width was determined in the selected solvent system 1-PrOH/0.01 M aq NaOH 1:2 v/v using four different concentrations and two heating/cooling rates. The most important conditions are given in Table 16 together with the temperatures at which clear solutions were obtained during heating ($T_{clear}$), and the temperatures at which solutions started to crystallize during cooling ($T_{cloud}$). The results of the experiments using a heating and cooling rate of 3K/hour are depicted in FIG. 25. As shown in FIG. 25, $T_{cloud}$ is indicated by squares, and $T_{clear}$ is indicated by diamonds.

TABLE 16

| MSZW Experiments in 1-PrOH/0.01M aq NaOH (1:2 v/v) | | | | |
|---|---|---|---|---|
| Concentration (mg Compound 1/mL solvent mixture) | $T_{clear}$ (° C.) | | $T_{cloud}$ (° C.) | |
| | 10 K/h | 3 K/h | 10 K/h | 3 K/h |
| 50 | 73 | 73.6 | 22 | 48.2 |
| 60 | 79 | 78.6 | 51 | 56.9 |
| 70 | 83 | 82.6 | 60 | 67 |
| 80 | 86 | 87.1 | 66 | 71.8 |

50 mg/mL, 10 K/h:

499 mg of crude Compound 1 was suspended in 10 mL of 1-propanol/0.01 M aq NaOH 1:2 v/v, stirred using a magnetic stirrer and heated to 90° C. with a heating rate of 10 K/hour. The solution formed was stirred at 90° C. for 10 minutes and then cooled to 10° C. with a cooling rate of 10K/hour.

60 mg/mL, 10 K/h:

599 mg of crude Compound 1 was suspended in 10 mL of 1-propanol/0.01 M aq NaOH 1:2 v/v, stirred using a magnetic stirrer and heated to 90° C. with a heating rate of 10 K/hour. The solution formed was stirred at 90° C. for 10 minutes and then cooled to 10° C. with a cooling rate of 10K/hour.

70 mg/mL, 10 K/h:

706 mg of crude Compound 1 was suspended in 10 mL of 1-propanol/0.01 M aq NaOH 1:2 v/v, stirred using a magnetic stirrer and heated to 90° C. with a heating rate of 10 K/hour. The solution formed was stirred at 90° C. for 10 minutes and then cooled to 10° C. with a cooling rate of 10K/hour.

80 mg/mL, 10 K/h:

804 mg of crude Compound 1 was suspended in 10 mL of 1-propanol/0.01 M aq NaOH 1:2 v/v, stirred using a magnetic stirrer and heated to 90° C. with a heating rate of 10 K/hour. The solution formed was stirred at 90° C. for 10 minutes and then cooled to 10° C. with a cooling rate of 10K/hour.

50 mg/mL, 3 K/h:

502 mg of crude Compound 1 was suspended in 10 mL of 1-propanol/0.01 M aq NaOH 1:2 v/v, stirred using a magnetic stirrer and heated to 90° C. with a heating rate of 3 K/hour. The solution formed was stirred at 90° C. for 10 minutes and then cooled to 10° C. with a cooling rate of 3 K/hour.

60 mg/mL, 3 K/h:

600 mg of crude Compound 1 was suspended in 10 mL of 1-propanol/0.01 M aq NaOH 1:2 v/v, stirred using a magnetic stirrer and heated to 90° C. with a heating rate of 3 K/hour. The solution formed was stirred at 90° C. for 10 minutes and then cooled to 10° C. with a cooling rate of 3 K/hour.

70 mg/mL, 3 K/h:

699 mg of crude Compound 1 was suspended in 10 mL of 1-propanol/0.01 M aq NaOH 1:2 v/v, stirred using a magnetic stirrer and heated to 90° C. with a heating rate of 3 K/hour. The solution formed was stirred at 90° C. for 10 minutes and then cooled to 10° C. with a cooling rate of 3 K/hour.

80 mg/mL, 3 K/h:

802 mg of crude Compound 1 was suspended in 10 mL of 1-propanol/0.01 M aq NaOH 1:2 v/v, stirred using a magnetic stirrer and heated to 90° C. with a heating rate of 3 K/hour. The solution formed was stirred at 90° C. for 10 minutes and then cooled to 10° C. with a cooling rate of 3K/hour.

Without wising to be bound by theory, these experiments show that for the most concentrated system (800 mg Compound 1 in 10 mL solvent mixture) an appropriate temperature for seeding is between 75° C. and 80° C.

Medium Scale Crystallization Experiments

Experiments involving medium scale reaction volumes (about 100 mL to 270 mL) were carried out using the Mettler-Toledo MultiMax system equipped with a MultiMax six-necked glass reactor (volume=300 mL, diameter 70 mm) inserted in a jacketed enclosure along with a two-bladed metal impeller (diameter 40 mm), a thermocouple for temperature control, and a turbidity probe. The reactor contents temperature, $T_r$, was used as the control variable in the applied temperature programs. For vacuum filtration sintered glass funnels were used (porosity P4; diameter 65 mm).

Five medium scale crystallization experiments were carried out using the MultiMax system in order to further optimize the crystallization process at a 20 g scale (Exp. Nos. 26-30). Without wishing to be bound by theory, these experiments in general confirmed the findings of the small scale crystallization experiments regarding solvent selection, concentration, temperature program and seeding. At the 20 g scale it was possible to improve the stirring conditions in order to maintain the suspension over the whole experiment, preventing lower purity deposits of solid material on the glass wall of the reactor above the suspension. Seeding conditions and final temperature were also investigated.

The crystallization procedure of Exp. No. 29 was found to be suitable for large scale crystallization. The key parameters for the crystallization process for Compound 1 Form A at the 20-g scale are given in below:

HPLC purity crude Compound 1: Compound 1: 99.08 area % (280 nm); Benzoic acid: 1.14 area % (223 nm); Impurity No. 1: 0.45 area % (280 nm); Impurity No. 2: 0.41 area % (280 nm).

Solvent system: 1-PrOH/0.01 M aq NaOH 1:2 v/v pH: 12.0 to 12.2.

Concentration: 80 mg/mL.

Solvent volume: 12.5 mL/g Compound 1.

Start temperature: Room temperature (RT).

Heating rate (RT to 90° C.) 30 K/hour.

Stirring time at 90° C.; 15 minutes.

Cooling rate (90° C. to 80° C.): 15K/hour.

Stirring time at 80° C. before seeding 10 minutes.

Seeding at 80° C.; 0.01 g seeding material/g dissolved Compound 1 (1% m/m) Plate-like particles average diameter about 20 m to 90 µm.

Stirring at 80° C. after seeding; 60 minutes

Cooling rate (80° C. to 5° C.): 5K/hour

Stirring time at 5° C. before filtration: 4 hours

Filtration: Sintered glass funnel (porosity P4)

pH mother liquor: About 11.7

Washing: 2×20 mL water/20 g Compound 1

Air drying: 15 minutes at room temperature

Vacuum drying: 45° C./10 mbar to 20 mbar/overnight

Yield: About 88%

HPLC benzoic acid: About 0.03 area % (223 nm)

HPLC Impurity No. 1: About 0.01 area % (280 nm)

HPLC Impurity No. 2: About 0.3 area % (280 nm)

PXRD: Compound 1 Form A

Residual 1-propanol ($^1$H-NMR): <0.1% m/m

Microscopy: Plate-like particles about 50 µm to 250 µm.

Experiment No. 26

Experiment No. 26 tested seeding behavior at 75° C. at the 16 g scale as well as chemical stability when stirring suspensions at 75° C. for extended times.

16.02 g of Compound 1 were placed in a 300 mL glass reactor (diameter 70 mm) and 200 mL of 1-propanol/0.01 M NaOH aq 1:2 v/v were added at room temperature. The suspension was stirred using a two-bladed impeller (diameter 40 mm; 500 rpm) and heated to 90° C. in 30 minutes. After stirring at 90° C. for about 15 minutes (500 rpm) the solution formed was cooled to 75° C. with a cooling rate of 15K/hour and stirred at 75° C. for 10 minutes.

At 75° C. the solution was seeded with a suspension of 158 mg of crude Compound 1 in 5 mL of water. The weak suspension formed was stirred at 75° C. overnight followed by hot filtration (sintered glass funnel, porosity P4, diameter 65 mm; the suspension was easy to filter). The glass reactor was flushed with 20 mL of water and the washing suspension was also filtered. The filter cake was again washed with 20 mL of water and air dried for 20 minutes by drawing ambient air through the glass funnel.

The solid was then vacuum dried at about 45° C./about 20 mbar. After drying for 3 days the solid product was 8.07 g of a yellowish powder. Yield: 49.4% (corrected for seeding material).

PXRD showed the pattern of Compound 1 Form A. Microscopy revealed that very well-formed plate-like particles were produced. HPLC of the resulting material showed a high purity of Compound 1 as shown in Table 17. Benzoic acid and Impurity No. 1 were significantly reduced. The content of Impurity No. 2 was decreased.

About 49% of dissolved Compound 1 crystallized at 75° C. after seeding. Compound 1 was found to be chemically stable even after stirring of the suspension at 75° C. overnight.

TABLE 17

HPLC Purity of Product of Experiment No. 26

|  | Percent Area |
|---|---|
| Compound 1 (280 nm) | 99.84 |
| Benzoic Acid (223 nm) | <0.01 |
| Impurity No. 1 (280 nm) | 0.01 |
| Impurity No. 2 (280 nm) | 0.15 |

Experiment No. 27

Experiment No. 27 tested seeding at 75° C. and cooling to 10° C. as well as stirring speed 200 rpm. The experiment also tested filtration behavior when cooling to 10° C., and the HPLC purity of material suspended over the whole experiment as well as deposits of solid material above the suspension.

16.00 g of crude Compound 1 were placed in a 300 mL glass reactor (diameter 70 mm) and 200 mL of 1-propanol/ 0.01 M NaOH aq 1:2 v/v were added at room temperature. The suspension was stirred using a two-bladed impeller (diameter 40 mm; 500 rpm) and heated to 90° C. in 30 minutes. After stirring at 90° C. for about 15 minutes (200 rpm) the solution formed was cooled to 75° C. with a cooling rate of 15K/hour and stirred at 75° C. for 10 minutes.

At 75° C. the solution was seeded with a suspension of 156 mg of crude Compound 1 in 5 mL of water. The weak suspension formed was stirred at 75° C. for 10 minutes and cooled to 10° C. with a cooling rate of 5K/hour, and then stirred at 10° C. for 5 hours.

Because of the low stirring speed of 200 rpm it was hard to maintain the suspension over the whole experiment. In addition, a deposit of solid material above the suspension was observed (about 0.37 g) and separately characterized by HPLC. The suspension was filtered using a sintered glass funnel (porosity P4; diameter 65 mm; the suspension was easy to filter). The filter cake was air dried for 20 minutes by drawing ambient air through the glass funnel.

The solid was then vacuum dried at about 45° C./about 20 mbar. After drying for 3 days the solid product was 13.78 g of a yellowish powder. Yield: 85.1% (corrected for seeding material).

PXRD showed the pattern of Compound 1 Form A. Microscopy revealed that very well-formed plate-like particles were produced. The residual 1-propanol content estimated by $^1$H-NMR was <0.1% m/m. HPLC of the resulting material showed a high purity of Compound 1. Benzoic acid and Impurity No. 1 were significantly reduced. The content of Impurity No. 2 was decreased. However, the solid deposit above the suspension showed a lower purity as shown in Table 18.

Seeding at 75° C. and cooling to 10° C. resulted in high yield. Stirring speed of 200 rpm was found to be too low to maintain the suspension over the whole experiment. The suspension was easy to filter at 10° C. Benzoic acid and Impurity No. 1 were significantly reduced; content of Impurity No. 2 decreased. Deposits of solid material above the suspension exhibited lower purity.

TABLE 18

HPLC Purity of Product of Experiment No. 27

|  | Recrystallized material (area %) | Deposit of solid material above the suspension (area %) |
|---|---|---|
| Compound 1 (280 nm) | 99.69 | 99.42 |
| Benzoic acid (223 nm) | 0.02 | 0.20 |
| Impurity No. 1 (280 nm) | 0.03 | 0.17 |
| Impurity No. 2 (280 nm) | 0.28 | 0.40 |

Experiment No. 28 (Carried Out in Parallel with Experiment No. 27)

Experiment No. 28 tested seeding at 75° C. and cooling to 5° C. at a stirring speed of 200 rpm. It also tested filtration behavior when cooling to 5° C., and HPLC purity of material suspended over the whole experiment as well as deposits of solid material above the suspension.

16.01 g of crude Compound 1 were placed in a 300 mL glass reactor (diameter 70 mm) and 200 mL of 1-propanol/ 0.01 M NaOH aq 1:2 v/v were added at room temperature. The suspension was stirred using a two-bladed impeller (diameter 40 mm; 500 rpm) and heated to 90° C. in 30 minutes. After stirring at 90° C. for about 15 minutes (200 rpm) the solution formed was cooled to 75° C. with a cooling rate of 15K/hour and stirred at 75° C. for 10 minutes.

At 75° C. the solution was seeded with a suspension of 158 mg of crude Compound 1 in 5 mL of water. The weak suspension formed was stirred at 75° C. for 10 minutes and cooled to 5° C. with a cooling rate of 5K/hour, and then stirred at 5° C. for 4 hours.

Because of the low stirring speed of 200 rpm it was hard to maintain the suspension over the whole experiment. In addition, a deposit of solid material above the suspension was observed (about 0.41 g) and separately characterized by HPLC. The suspension was filtered using a sintered glass funnel (porosity P4; diameter 65 mm; the suspension was easy to filter). The filter cake was air dried for 20 minutes by drawing ambient air through the glass funnel.

The solid was then vacuum dried at about 45° C./about 20 mbar. After drying for 3 days the solid product was 13.54 g of a yellowish powder. Yield: 83.6% (corrected for seeding material).

PXRD showed the pattern of Compound 1 Form A. Microscopy revealed that very well-formed plate-like particles were produced. The residual 1-propanol content estimated by $^1$H-NMR was <0.1% m/m.

HPLC of the resulting material showed a high Compound 1 purity. Benzoic acid and Impurity No. 1 were significantly reduced. The content of Impurity No. 2 was decreased. However, the solid deposit above the suspension showed a lower purity as shown in Table 19.

Seeding at 75° C. and cooling to 5° C. resulted in high yield. Stirring speed of 200 rpm was found to be too low to maintain the suspension over the whole experiment. The suspension was easy to filter at 5° C. Benzoic acid and Impurity No. 1 were significantly reduced; the content of Impurity No. 2 decreased. Deposits of solid material above the suspension exhibited lower purity.

TABLE 19

HPLC Purity of the Product of Experiment No. 28

|  | Recrystallized Material (area %) | Deposit of solid material above the suspension (area %) |
| --- | --- | --- |
| Compound 1 (280 nm) | 99.70 | 99.50 |
| Benzoic acid (223 nm) | 0.01 | 0.03 |
| Impurity No. 1 (280 nm) | 0.01 | 0.08 |
| Impurity No. 2 (280 nm) | 0.29 | 0.42 |

Experiment No. 29

Experiment No. 29 tested seeding at 80° C. and cooling to 5° C. at a stirring speed of 500 rpm. It also tested whether deposits of solid material above the suspension could be prevented. The solid material was characterized by PXRD, microscopy, $^1$HNMR (residual 1-propanol) and TG-FTIR.

20.98 g of crude Compound 1 were placed in a 300 mL glass reactor (diameter 70 mm) and 262 mL of 1-propanol/0.01 M NaOH aq 1:2 v/v were added at room temperature. The suspension was stirred using a two-bladed impeller (diameter 40 mm; 500 rpm) and heated to 90° C. in 30 minutes. After stirring at 90° C. for about 15 minutes (500 rpm) the solution formed was cooled to 80° C. with a cooling rate of 15K/hour and stirred at 80° C. for 10 minutes.

At 80° C. the solution was seeded with a suspension of 209 mg of crude Compound 1 in 5 mL of water. The weak suspension formed was stirred at 80° C. for one hour and cooled to 5° C. with a cooling rate of 5K/hour, and then stirred at 5° C. for 4 hours.

The easy-to-stir suspension was filtered using a sintered glass funnel (porosity P4; diameter 65 mm). The suspension was easy to filter (mother liquor pH: 11.7). The glass reactor was flushed with 20 mL of water and the washing suspension was also filtered. The filter cake was again washed with 20 mL of water and air dried for 20 minutes by drawing ambient air through the glass funnel.

The solid was then vacuum dried at about 45° C./about 20 mbar. After drying overnight the solid product was 18.59 g and after 4 days 18.58 g of a yellowish powder. Yield: 87.6% (corrected for seeding material).

Figure 26:
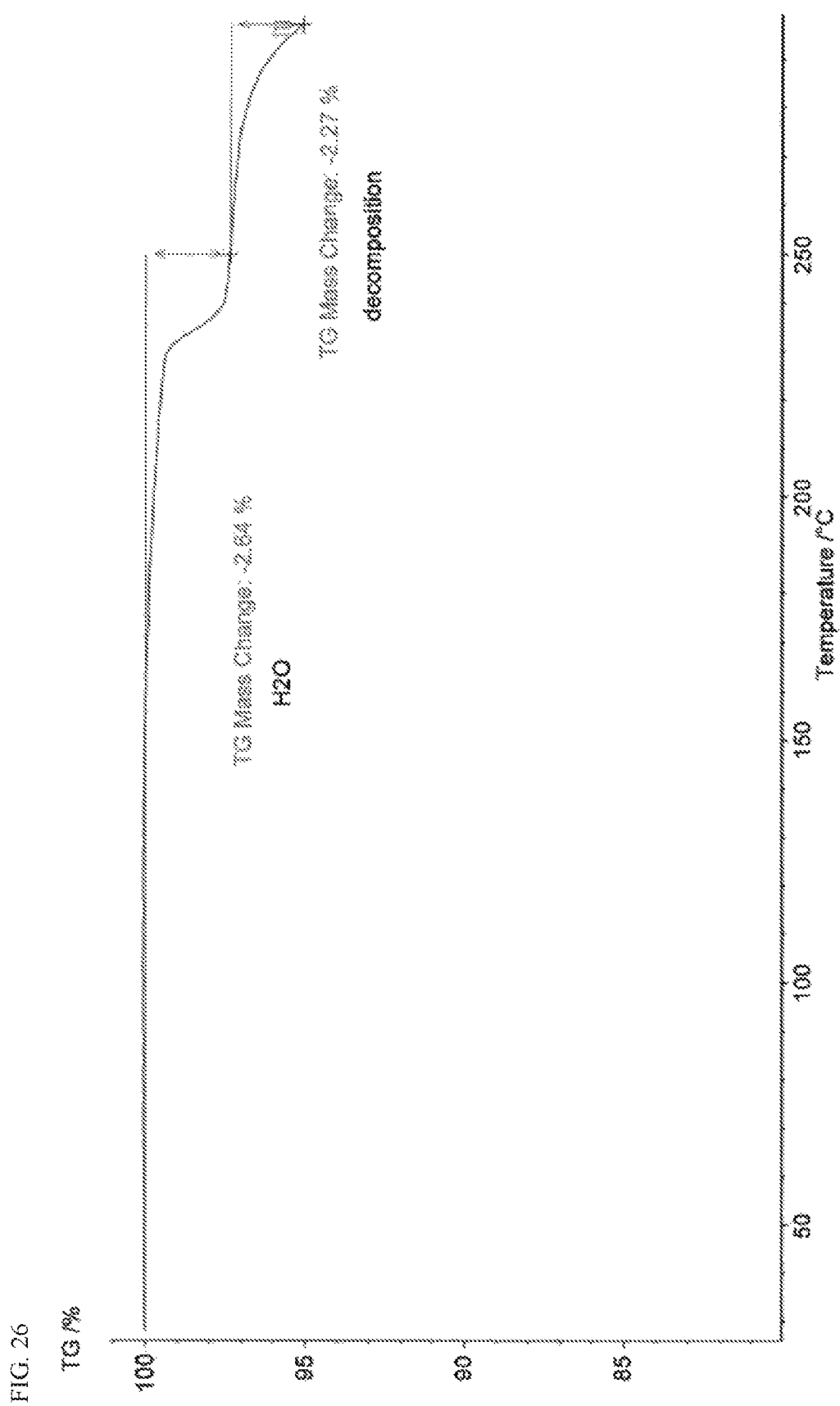
FIG. 26 is a TG-FTIR plot of the solid recovered from Experiment No. 29 in Example 6.

PXRD showed the pattern of Compound 1, Form A. Microscopy revealed that very well-formed plate-like particles were produced. The residual 1-propanol content estimated by $^1$H-NMR was <0.1% m/m. TG-FTIR showed a mass loss step in the temperature range about 170° C. to about 250° C. of 2.6% which was attributable to water, as shown in FIG. 26. HPLC showed a high purity of Compound 1. Benzoic acid and Impurity No. 1 were significantly reduced. The content of Impurity No. 2 was decreased as shown in Table 20.

A stirring speed of 500 rpm maintained the suspension over the whole experiment. An effective cooler was necessary in order to prevent partial evaporation of the solvent at 90° C. Seeding at 80° C. and cooling to 5° C. resulted in high yield. Seeding at 80° C. is more appropriate because of the lower supersaturation. Almost no deposits of solid material above the suspension were observed. Benzoic acid and Impurity No. 1 were significantly reduced; the content of Impurity No. 2 decreased.

The precise amount of sodium hydroxide at the beginning of the crystallization experiment can affect the recrystallization. To ensure consistency, the diluted sodium hydroxide solution can be freshly prepared shortly before beginning the crystallization experiment. The pH of the mother liquor of after filtration was 11.7, which is somewhat lower than the expected pH of a 1-propanol/0.01 M NaOH aq 1:2 v/v solution (pH about 12). This could be due to the presence of 1-propanol and sodium salt formation by acidic impurities. Another explanation could be $CO_2$ uptake from air and partial formation of $NaHCO_3$. It could also be because of the significantly lower $pK_a$ values of benzoic acid and Impurity No. 1 compared to the $pK_a$ of carbonic acid. Benzoic acid and Impurity No. 1 will can be transformed into the sodium salts with $NaHCO_3$. This crystallization procedure was found to be suitable for large scale experiments.

TABLE 20

HPLC Purity of Product of Experiment No. 29

|  | Percent Area |
| --- | --- |
| Compound 1 (280 nm) | 99.71 |
| Benzoic Acid (223 nm) | 0.03 |
| Impurity No. 1 (280 nm) | <0.01 |
| Impurity No. 2 (280 nm) | 0.29 |

Experiment No. 30

Experiment No. 30 tested seeding at 75° C. and cooling to 5° C. at a stirring speed of 500 rpm. It also tested whether deposits of solid material above the suspension could be prevented. The solid material was characterized by PXRD, microscopy, $^1$HNMR (residual 1-propanol) and TG-FTIR.

21.62 g of crude Compound 1 were placed in a 300 mL glass reactor (diameter 70 mm) and 270 mL of 1-propanol/0.01 M NaOH aq 1:2 v/v were added at room temperature. The suspension was stirred using a two-bladed impeller (diameter 40 mm; 500 rpm) and heated to 90° C. in 30 minutes. After stirring at 90° C. for about 15 minutes (500 rpm) the solution formed was cooled to 75° C. with a cooling rate of 15K/hour and stirred at 75° C. for 10 minutes.

At 75° C. the solution was seeded with a suspension of 213 mg of crude Compound 1 in 5 mL of water. The weak suspension formed was stirred at 75° C. for one hour and cooled to 5° C. with a cooling rate of 5K/hour, and then stirred at 5° C. for 6 hours.

The easy-to-stir suspension was filtered using a sintered glass funnel (porosity P4; diameter 65 mm). The suspension was easy to filter (mother liquor pH: 11.7) The glass reactor was flushed with 20 mL of water and the washing suspension was also filtered. The filter cake was again washed with 20 mL of water and air dried for 20 minutes by drawing ambient air through the glass funnel.

The solid was then vacuum dried at about 45° C./about 20 mbar. After drying for 3 days the solid product was 19.06 g of a yellowish powder. Yield: 87.2% (corrected for seeding material).

Figure 27:
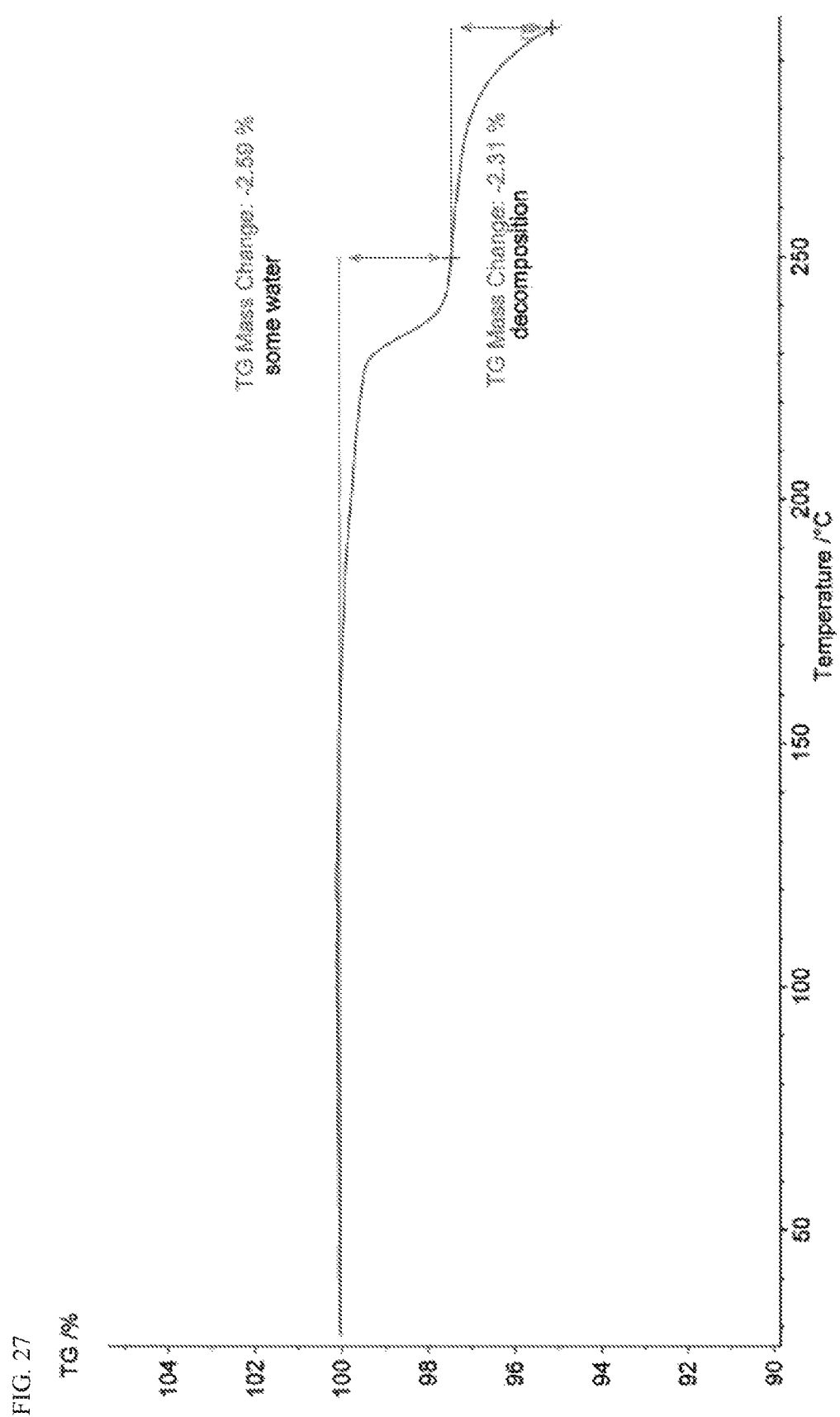
FIG. 27 is a TG-FTIR plot of the solid recovered from Experiment No. 30 in Example 6.

PXRD showed the pattern of Compound 1, Form A. Microscopy revealed that very well-formed plate-like particles were produced. The residual 1-propanol content estimated by $^1$H-NMR was <0.1% m/m. TG-FTIR showed a mass loss step in the temperature range about 160° C. to about 250° C. of 2.6% which was attributable to water (FIG. 27). HPLC showed a high Compound 1 purity (Table 21). Benzoic acid and Impurity No. 1 were significantly reduced. The content of Impurity No. 2 was decreased.

Seeding at 75° C. and cooling to 5° C. resulted in high yield. A stirring speed of 500 rpm maintained the suspension over the whole experiment. Benzoic acid and Impurity No.

1 were significantly reduced; the content of Impurity No. 2 decreased. Almost no deposits of solid material above the suspension were observed. The results were the same as for experiment No. 29. However, seeding at 80° C. (as carried out in experiment No. 29) reduced the probability of spontaneous crystallization before seeding. Accordingly, seeing at 80° C. as set forth in Experiment No. 29 was found to be the most robust method for the preparation of Form A on an industrial scale.

TABLE 21

HPLC Purity of Product of Experiment No. 30

|  | Percent Area |
| --- | --- |
| Compound 1 (280 nm) | 99.72 |
| Benzoic Acid (223 nm) | 0.02 |
| Impurity No. 1 (280 nm) | <0.01 |
| Impurity No. 2 (280 nm) | 0.28 |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. Crystalline 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide hemihydrate.

2. A crystalline hemihydrate form ("Form A") of 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide, wherein said Form has a powder X-ray diffraction pattern comprising a peak at a diffraction angle (2θ) of about 26.2°, wherein said powder X-ray diffraction pattern is obtained using Cu Kα1 X-rays at a wavelength of 1.5406 Å.

3. The crystalline hemihydrate of claim 2, wherein the morphic form is further characterized by an endothermic peak at about 231° C. as measured by differential scanning calorimetry.

4. The crystalline hemihydrate form of claim 2, further characterized by a mass loss of about 2.4% between a temperature of about 110° C. and 220° C. as measured by thermogravimetric analysis.

5. The crystalline hemihydrate form of claim 2, further characterized by a PXRD pattern substantially similar to that set forth in FIG. 1A.

6. The crystalline hemihydrate form of claim 2, further characterized by a PXRD pattern substantially similar to that set forth in FIG. 1B.

7. The crystalline hemihydrate form of claim 2, further characterized by a TG-FTIR profile substantially similar to that set forth in FIG. 8.

8. The crystalline hemihydrate form of claim 2, further characterized by a DSC profile substantially similar to that set forth in FIG. 15.

9. The crystalline hemihydrate form of claim 2, further characterized by a DVS profile substantially similar to that set forth in FIG. 20A.

10. The crystalline hemihydrate form of claim 2, further characterized by a DVS profile substantially similar to that set forth in FIG. 20B.

11. The crystalline hemihydrate form of claim 2, wherein the morphic form is substantially non-hygroscopic.

12. A method of preparing a crystalline hemihydrate form of 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide comprising:
recrystallizing the 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide from a solvent having a water activity of at least about 0.18.

13. A pharmaceutical composition comprising the crystalline 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide hemihydrate of claim 1, and a pharmaceutically acceptable carrier.

14. A method of treating a viral infection in a subject in need thereof, comprising administering to the subject a therapeutically effective amount of the crystalline 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide hemihydrate of claim 1.

15. A pharmaceutical composition comprising the crystalline hemihydrate form of claim 2, and a pharmaceutically acceptable carrier.

16. A method of treating a viral infection in a subject in need thereof, comprising administering to the subject a therapeutically effective amount of the crystalline hemihydrate form of claim 2.

* * * * *